US010344289B2

(12) United States Patent
Gupta et al.

(10) Patent No.: US 10,344,289 B2
(45) Date of Patent: Jul. 9, 2019

(54) ENGINEERED ZINC FINGER PROTEINS TARGETING 5-ENOLPYRUVYL SHIKIMATE-3-PHOSPHATE SYNTHASE GENES

(71) Applicants: Dow AgroSciences LLC, Indianapolis, IN (US); Sangamo BioSciences, Inc., Richmond, CA (US)

(72) Inventors: Manju Gupta, Indianapolis, IN (US); Asha M. Palta, Indianapolis, IN (US); Stephen Novak, Indianapolis, IN (US); Fyodor Urnov, Richmond, CA (US); Sunita Gopalan, Richmond, CA (US)

(73) Assignees: Dow AgroSciences LLC, Indianapolis, IN (US); Sangamo Therapeutics, Inc., Richmond, CA (US)

( * ) Notice: Subject to any disclaimer, the term of this patent is extended or adjusted under 35 U.S.C. 154(b) by 735 days.

(21) Appl. No.: 14/538,609

(22) Filed: Nov. 11, 2014

(65) Prior Publication Data

US 2015/0064790 A1   Mar. 5, 2015

Related U.S. Application Data

(60) Continuation of application No. 13/766,380, filed on Feb. 13, 2013, now Pat. No. 8,889,390, which is a division of application No. 12/284,888, filed on Sep. 25, 2008, now Pat. No. 8,399,218.

(60) Provisional application No. 60/995,557, filed on Sep. 27, 2007.

(51) Int. Cl.
| C12N 15/66 | (2006.01) |
|---|---|
| C12N 15/62 | (2006.01) |
| C12N 15/82 | (2006.01) |
| C12N 9/10 | (2006.01) |

(52) U.S. Cl.
CPC ....... *C12N 15/8213* (2013.01); *C12N 9/1092* (2013.01); *C12N 15/8243* (2013.01); *C12N 15/8274* (2013.01); *C07K 2319/00* (2013.01); *C07K 2319/81* (2013.01)

(58) Field of Classification Search
None
See application file for complete search history.

(56) References Cited

U.S. PATENT DOCUMENTS

| 4,940,835 A | 7/1990 | Shah et al. |
|---|---|---|
| 4,971,908 A | 11/1990 | Kishore et al. |
| 5,145,783 A | 9/1992 | Kishore et al. |
| 5,188,642 A | 2/1993 | Shah et al. |
| 5,310,667 A | 5/1994 | Eichholtz et al. |
| 5,312,910 A | 5/1994 | Kishore et al. |
| 5,356,802 A | 10/1994 | Chandrasegaran |
| 5,436,150 A | 7/1995 | Chandrasegaran |
| 5,463,175 A | 10/1995 | Barry et al. |
| 5,487,994 A | 1/1996 | Chandrasegaran |
| 5,554,798 A | 9/1996 | Lundquist et al. |
| 5,627,061 A | 5/1997 | Barry et al. |
| 5,633,435 A | 5/1997 | Barry et al. |
| 5,776,760 A | 7/1998 | Barry et al. |
| 5,789,538 A | 8/1998 | Rebar et al. |
| 5,804,425 A | 9/1998 | Barry et al. |
| 5,866,775 A | 2/1999 | Eichholtz et al. |
| 5,925,523 A | 7/1999 | Dove et al. |
| 6,007,988 A | 12/1999 | Choo et al. |
| 6,013,453 A | 1/2000 | Choo et al. |
| 6,040,497 A | 3/2000 | Spencer et al. |
| 6,140,081 A | 10/2000 | Barbas |
| 6,140,466 A | 10/2000 | Barbas et al. |
| 6,200,759 B1 | 3/2001 | Dove et al. |
| 6,225,114 B1 | 5/2001 | Eichholtz et al. |
| 6,242,568 B1 | 6/2001 | Barbas et al. |
| 6,248,876 B1 | 6/2001 | Barry et al. |
| 6,410,248 B1 | 6/2002 | Greisman et al. |
| 6,453,242 B1 | 9/2002 | Eisenberg et al. |
| 6,479,626 B1 | 11/2002 | Kim et al. |
| 6,534,261 B1 | 3/2003 | Cox et al. |
| 6,733,970 B2 | 5/2004 | Choo et al. |
| 6,746,838 B1 | 6/2004 | Choo et al. |
| 6,750,377 B1 | 6/2004 | Kastor, Jr. |
| 6,785,613 B2 | 8/2004 | Eisenburg et al. |
| 6,794,136 B1 | 9/2004 | Eisenberg et al. |
| 6,803,501 B2 | 10/2004 | Baerson et al. |
| 6,866,997 B1 | 3/2005 | Choo et al. |
| 6,977,154 B1 | 12/2005 | Choo et al. |
| 7,001,768 B2 | 2/2006 | Wolfe |

(Continued)

FOREIGN PATENT DOCUMENTS

| GB | 2338237 A | 12/1999 |
|---|---|---|
| WO | WO 95/19431 A1 | 7/1995 |

(Continued)

OTHER PUBLICATIONS

Wright et al, Nature Protocols (2006) 1:1637-1652.*
Wright et al, Plant J. (2005) 44:693-705.*
Dreier et al, J. Biol. Chem. Papers in Press, Published Online May 4, 2001.*
Takatsuji, et al.,"Target-Sequence Recognition by Separate-Type CYS2/HIS2 Zinc Finger Proteins in Plants," J. Biol. Chem. 271(38):23368-23373 (1996).
Wright, et al., "High-Frequency Homologous Recombination in Plants Mediated by Zinc-Finger Nucleases," Plant J. 44:693-705 (2005).

(Continued)

*Primary Examiner* — Mykola V. Kovalenko
(74) *Attorney, Agent, or Firm* — Pasternak Patent Law

(57) ABSTRACT

The present disclosure relates to engineered zinc finger proteins that target 5-enolpyruvyl shikimate-3-phosphate synthase (EPSPS) genes in plants and methods of using such zinc finger proteins in modulating gene expression, gene inactivation, and targeted gene modification. In particular, the disclosure pertains to zinc finger nucleases for targeted cleavage and alteration of EPSPS genes.

8 Claims, 30 Drawing Sheets

Specification includes a Sequence Listing.

(56) References Cited

U.S. PATENT DOCUMENTS

| | | | |
|---|---|---|---|
| 7,030,215 B2 | 4/2006 | Liu et al. | |
| 7,045,684 B1 | 5/2006 | Held et al. | |
| 7,141,722 B2 | 11/2006 | Fincher et al. | |
| 7,169,970 B2 | 1/2007 | Warner et al. | |
| 7,214,535 B2 | 5/2007 | Sun et al. | |
| 7,220,719 B2 | 5/2007 | Case et al. | |
| 7,235,354 B2 | 6/2007 | Case et al. | |
| 7,238,508 B2 | 7/2007 | Lin et al. | |
| 7,262,054 B2 | 8/2007 | Jamieson et al. | |
| 7,723,575 B2* | 5/2010 | Alibhai | C12N 9/1092 536/23.2 |
| 7,833,784 B2* | 11/2010 | Barbas, III | C12N 9/50 435/252.3 |
| 7,888,121 B2* | 2/2011 | Urnov | C07K 14/43595 435/320.1 |
| 2002/0046419 A1 | 4/2002 | Choo et al. | |
| 2003/0068675 A1* | 4/2003 | Liu | C07K 1/00 435/69.1 |
| 2003/0232410 A1 | 12/2003 | Liljedahl et al. | |
| 2004/0128717 A1* | 7/2004 | Jamieson | C12N 15/8216 800/280 |
| 2004/0224385 A1* | 11/2004 | Barbas | C07K 14/4703 435/69.1 |
| 2005/0026157 A1 | 2/2005 | Baltimore | |
| 2005/0064474 A1 | 3/2005 | Urnov et al. | |
| 2005/0208489 A1 | 9/2005 | Carroll | |
| 2005/0267061 A1 | 12/2005 | Martin | |
| 2006/0063231 A1 | 3/2006 | Li et al. | |
| 2007/0134796 A1 | 6/2007 | Holmes et al. | |
| 2008/0182332 A1 | 7/2008 | Cai et al. | |

FOREIGN PATENT DOCUMENTS

| | | |
|---|---|---|
| WO | WO 96/06166 A1 | 2/1996 |
| WO | WO 98/37186 A1 | 8/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 00/66748 A1 | 11/2000 |
| WO | WO 01/53480 A1 | 7/2001 |
| WO | WO 01/60970 A2 | 8/2001 |
| WO | WO 01/88197 A2 | 11/2001 |
| WO | WO 02/08286 A2 | 1/2002 |
| WO | WO 02/016536 A1 | 2/2002 |
| WO | 2002/057294 A2 | 7/2002 |
| WO | WO 02/057293 A2 | 7/2002 |
| WO | WO 02/077227 A2 | 10/2002 |
| WO | WO 02/099084 A2 | 12/2002 |
| WO | WO 03/016496 A2 | 2/2003 |
| WO | WO 03/080809 A2 | 10/2003 |
| WO | WO 03/087341 A2 | 10/2003 |
| WO | WO 05/014791 A2 | 2/2005 |
| WO | WO 05/084190 A2 | 9/2005 |
| WO | 2008/076290 A2 | 6/2008 |

OTHER PUBLICATIONS

Zhou, et al., "Identification of a Glyphosate-Resistant Mutant of Rice 5-Enolpyruvylshikimate 3-Phosphate Synthase Using a Directed Evolution Strategy," Plant Physiol. 140:184-195 (2006).
Akopian, et al., "Chimeric Recombinases With Designed DNA Sequence Recognition" PNAS USA 100:8688-8691 (2003).
Arnold, et al., "Application of Designed Zinc-Finger Protein Technology in Plants" Plant Biology/Joint Annual Meeting of the American Society of Plant Biologist, pp. 248-249, Abstract #P44015 (2007).
Baker, et al., "Zinc Finger Nuclease-Mediated Homologous Recombination in Tobacco Cell Cultures," In Vitro Cellular & Developmental Biology 43: S59, Abstract #P-2053 (2007).
Barahmand-Pour, et al., "A Role for Stat Family Transcription Factors in Myeloid Differentiation," Curr. Top. Microbiol. Immunol. 211: 121-128 (1996).
Beerli, et al., "Engineering Polydactyl Zinc-Finger Transcription Factors," Nature Biotechnology 20:135-141 (2002).
Bentley, et al., "The Shikimate Pathway. A Metabolic Tree With Many Branches," Crit. Rev. Biochem Mol Biol 25:307-384 (1990).
Bibikova, et al., "Stimulation of Homologous Recombination Through Targeted Cleavage by Chimeric Nucleases," Mol Cell Biol 21:289-297 (2001).
Cai, et al., "Gene Targeting in Plants Via Engineered Zinc Finger Proteins," Plant Biology/Joint Annual Meeting of the American Society of Plant Biologist, p. 247, Abstract #P44006 (2007).
Choo, et al., "Advances in Zinc Finger Engineering," Curr. Opin. Struct. Biol. 10:411-416 (2000).
Desjarlais, et al., "Use of a Zinc-Finger Consensus Sequences Framework and Specificity Rules to Design Specific DNA Binding, Proteins" PNAS 90:2256-2260 (1993).
Desjarlais, et al., "Length-Encoded Multiplex Binding Site Determination: Application to Zinc Finger Proteins," PNAS USA 91:11099-11103 (1994).
Dreier, et al., "Development of Zinc Finger Domains for Recognition of the 5'-Ann-3' Family of DNA Sequences and Their Use in the Construction of Artificial Transcription Factors," J. of Biol. Chem. 276:29466-29478 (2001).
Durai, et al., "Zinc Finger Nucleases: Custom-Designed Molecular Scissors for Genome Engineering of Plant and Mammalian Cells,"Nucleic Acids Research 33:5978-5990 (2005).
Ho, et al., "Dimeric Ligands Define a Role for Transcriptional Activation Domains in Reinitiation," Nature 382:822-826 (1996).
Isalan, et al., "A Rapid, Generally Applicable Method to Engineer Zinc Fingers Illustrated by Targeting the HIV-1 Promoter," Nat Biotechnol 19:656-660 (2001).
Kim, et al., "Hybrid Restriction Enzymes: Zinc Finger Fusions FOK 1 Cleavage Domain," PNAS 93:1156-1160 (1996).
Klemm, et al., "Dimerization as a Regulatory Mechanism in Signal Transduction," Annu. Rev. Immunol. 16:569-592 (1998).
Klug, "Zinc Finger Peptides for the Regulation of Gene Expression," J. Mol. Biol. 293:215-218 (1999).
Liu, et al., "Design of Polydactyl Zinc-Finger Proteins for Unique Addressing Within Complex Genomes," PNAS 94:5525-5530 (1997).
Miller, et al., "Repetitive Zinc-Binding Domains in the Protein Transcription Factor IIIA From Xenopus Oocytes," Embo J. 4:1609-1614 (1985).
O'Shea, "X-Ray Structure of the GCN4 Leucine Zipper, A Two-Stranded, Parallel Coiled Coil," Science 254:539-544 (1991)
Pabo, et al., "Design and Selection of Novel CYS2-HIS2 Zinc Finger Proteins," Ann. Rev. Biochem. 70:313-340 (2001).
Pomerantz, et al., "Analysis of Homeodomain Function by Structure-Based Design of a Transcription Factor," PNAS 92:9752-9756 (1995).
Pomerantz, et al., "Structure-Based Design of a Dimeric Zinc Finger Protein," Biochemistry37(4): 965-970 (1998).
Rhodes, et al., "Zinc Fingers," Sci. Amer. 268:56-65 (1993).
Segal, et al., "Custom DNA-Binding Proteins Come of Age: Polydactyl Zinc-Finger Proteins," Curr. Opin. Biotechnol. 12:632-637 (2001).
Smith, et al., "Requirements for Double-Strand Cleavage by Chimeric Restriction Enzymes With Zinc Finger DNA-Recognition Domains," Nucleic Acids Res. 28:3361-3369 (2000).
Takatsuji, et al., "A New Family of Zinc Finger Proteins in Petunia: Structure, DNA Sequence Recognition, and Floral Organ-Specific Expression," Plant Cell 6:947-958 (2004).
Takatsuji, et al., "Target-Sequence Recognition by Separate-Type CYS2/HIS2 Zinc Finger Proteins in Plants," J. Biol. Chem. 271:23368-23373 (2006).
Urnov, et al., "Highly Efficient Endogenous Human Gene Correction Using Designed Zinc-Finger Nucleases," Nature 435:646-651 (2005).
U.S. Appl. No. 61/130,099 entitled "Compositions for Linking DNA-Binding Domains and Cleavage Domains," filed May 28, 2008.
U.S. Appl. No. 12/284,887 entitled "Rapid In Vivo Identification of Biologically Active Nucleases," filed Sep. 25, 2008.

(56) References Cited

OTHER PUBLICATIONS

Wright, et al., "High-Frequency Homologous Recombination in Plants Mediated by Zinc-Finger Nucleases," *The Plant Journal* 44:693-705 (2005).

Wright, et al., "Standardized Reagents and Protocols for Engineering Zinc Finger Nucleases by Modular Assembly," *Nature Protocols* 1:1637-1652 (2006).

Seibert, et al., "Efficient Repair of Genomic Double-Strand Breaks by Homolohous Recombination Between Directly Repeated Sequences in the Plant Genome," The Plant Cell 14(1):1121-1131 (2002).

Takatsuji, et al., "Characterization of a Zinc Finger DNA-Binding Protein Expressed Specifically in Petunia Petals and Seedlings," EMBO J. 11(1):241-249 (1992).

Dreier, et al., "Development of Zinc Finger Domains for Recognition of the 5_-CNN-3_ Family DNA Sequences and Their Use in the Construction of Artificial Transcription Factors," Journal of Biological Chemistry 280(42):35588-35597 (2005).

Miki, et al., "Selectable Marker Genes in Transgenic Plants: Applications, Alternatives and Biosafety," J. Biotech 107: 193-232 (2004).

* cited by examiner

← 452 bp

← 556 bp

← 609 bp

← 398 bp

Sequence comparison of the ZFN 10654/10657 binding sites among the EPSPS paralogs. Bases in small letters were skipped in the ZFN design.

Paralog A: GTCCACTTACAGCTGCAGTTACTGCTGCTGGTGGCA
Paralog B: GTCCACTTACCGCTGCAGTTACTGCTgCAGGTGGCA
Paralog C: GTCCACTCACCGCTGCAGTTACTGCTgCAGGTGGCA
Paralog D: GTCCACTCACCGCTGCAGTTACAGCTgCAGGTGGCA
Paralog E: GTCCACTCACCGCTGCAGTTACAGCTgCAGGTGGCA

Sequence comparison of the ZFN 10740/10741 binding sites among the EPSPS paralogs

Paralog A: TTCAACCCATTAGAGAAATCTCGGGTCTG
Paralog B: TTCAGCCCATTAGAGAAATCTCGGGTCTG
Paralog C: TTCAGCCCATTAGAGAAATCTCGGGTCTG
Paralog D: TTCAACCAATCAGAGAAATCTCGGGTCTC
Paralog E: TTCAACCAATCAGAGAAATCTCGGGTCTC

Fig. 4

```
AACAGCCATGCGTCCACTCACCGCTGCAGTTACAGCTGCAGGTGGCAACGCGAGGTAAGGTTAACGAGTTTTTGTTA    wild-type AACAGCCATGCGTCCACTCACCGCTGCAGT::::::::TGGCAACGCGAGGTAAGGTTAACGAGTTTTTGTTA        sample 2

AACAGCCATGCGTCCACTCACCGCTGC:::::::::TGCAGGTGGCAACGCGAGGTAAGGTTAACGAGTTTTTGTTA    sample 4

AACAGCCATGCGTCCACTCACCGCTGC::::::::TGCAGGTGGCAACGCGAGGTAAGGTTAACGAGTTTTTGTTA     sample 5 (35)
AACAGCCATGCGTCCACTCACCGCTGC:::::::TGCAGGTGGCAACGCGAGGTAAGGTTAACGAGTTTTT:GTTA     sample 5
AACAGCCATGCGTCCACTCACCGCTGC:::::::TGCAGGTGGCAACGCGAGGTAAGGTTAAGGTTAACGTAGTTTTTGTTA  sample 5
AACAGCCATGCGTCCAC:::::::::TTACAGCTGCAGGTGGCAACGCGAGGTAAGGTTAACGAGTTTTTGTTA       sample 5 (8)
AACAGCCATGCGTCCAC::::::::TTACAGCTGCAGGTGGCAACGCGAGGTAAGGTTAACGAGTTTTT:GTTA       sample 5
```

Fig. 6

Paralog C – wild-type reverse sequence
AAAGCTCCTTAACCTTTGCGTTGCCACCTGCAGCAGTAACGGCAGCGGTGAGTGGACGCATGGCTGTTCCTGCATTCCCAAGTA Paralog C – sample16 NHEJ
AAAGCTCCTTAACCTTTACCTTGCG::::::::::::::::::::::::::::TGGACGCATGGCTGTTCCTGCATTCCCAAGTA Paralog C wild-type forward sequence
AGAGTGATATTGAGTTGTACCTTGGGAATGCAGGAACAGCCATGCGTCCACTCACCGCTGCCGTTACTGCTGCAGGTGGCAACGCAAGGT Paralog C – sample 17 NHEJs
AGAGTGATATTGAGTTGTACCTT:GGAATGCAGGAACAGCCATGCGTTCCACTCACCGCTG:::::ACTGCTGCAGGTGGCAACGCAAGGT
AGAGTGATATTGAGTTGTACCTTGGGAATGCAGGAACAGCCATGCGTCCACTCACCGCTG:::::ACTGCTGCAGGTGGCAACGCAAGGT
AGAGTGATATTGAGTTGTACCTTGGGAATGCAGGAACAGCCATGCGTCCACTCACCGCTG:::::ACTGCTGCAGGTGGCAACGCAAGGT Paralog D – wild-type sequence
AGTTGTACCTTGGGAATGCAGGAACAGCCATGCGTCCACTCACCGCTGCAGTTACAGCTGCAGGTGGCAACGCGAGGTAAGGTTAACGAG Paralog D – sample forward sequence
AGTTGTACCTTGGGAATGCAGGAACAGCCATGC::::::::::::::::::::AGGTGGCAACGCGAGGTAAGGTTAACGAG
AGTTGTACCTTGGGAATGCAGGAACAGCCATGC::::::::::::::::::::AGGTGGCAACGCGAGGTAAGGTTAACGAG
AGTTGTACCTTGGGAATGCAGGAACAGCCATGC::::::::::::::::::::AGGTGGCAACGCGAGGTAAGGTTAACGAG
AGTTGTACCTTGGGAATGCAGGAACAGCCATGC::::::::::::::::::::AGGTGGTAACGCGAGGTAAGGTTAACGAG
AGTTGTACCTTGGGAATGCAGGAACAGCCATGCGTCCACTCACCGCTG::::::CTGCAGGTGGCAACGCGAGGTAAGGTTAACGAG
AGTTGTACCTTGGGAATGCAGGAACAGCCATGCGTCCACTCACCGCTG::::::CTGCAGGTGGCAACGCGAGGTAAGGTTAACGAG

Fig. 7A

Paralog D – wild-type reverse sequence

ATCAATTTCTTGACAATAACAAAAAAACTCGTTAACCTTACCTCGCGTTGCCACCTGCAGCTGTAACTGCAGCGGTGAGTGGACGCATGGC

Paralog D – sample 24 NHEJs

ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGACTGGACGCATGGC
ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGAGTGGACGCATGGC
ATCAATTTCTTGACAATAACAAAAAAACTACGTTAACCTTACCTCGCGTTGCCACCTGCAG::::::CAGCGGTGAGTGGACGCATGGC

Fig. 7B

Paralog A – wild-type forward sequence
AGCTTCGGAGATTGTGCTTCAACCCATTAGAGAAATCTCGGGTCTGATCAAGCTACCCGGATCCAAATCTCTGTCCAACCG Paralog A- sample 3 NHEJs
AGCTTCGGAGATTGTGCTTCAACCC::::::::::::::::::::::::::GGATCCAAATCTCTGTCCAACCG
AGCTTCGGAGATTGTGCTTCAACCCA:::::::::::::::::GGTCTGATCAAGCTACCCGGATCCAAATCTCTGTCCAACCG
AGCTTCGGAGATTGTGCTTCAACCCA::::::::::::::::GGTCTGATCAAGCTACCCGGATCCAAATCTCTGTCCAACCG
AGCTTCGGAGATTGTGCTTCAACCCA::::::::::::::TCGGGTCTGATCAAGCTACCCGGATCCAAATCTCTGTCCAACCG
AGCTTCGGAGATTGTGCTTCAACCCA::::::::::::TCGGGTCTGATCAAGCTACCCGGATCCAAATCTCTGTCCAACCG
AGCTTCGGAGATTGTGCTTCAACCCA::::::::::::TCGGGTCTGATCAAGCTACCCGGATCCAAATCTCTGTCCAACCG
AGCTTCGGAGATTGTGCTTCAACCCATT::::::::::::AGCTACCCGGATCCAAATCTCTGTCCAACCG
AGCTTCGGAGATTGTGCTTCAACCCATTA:::::::::GGGTCTGATCAAGCTACCCGGATCCAAATCTCTGTCCAACCG
AGCTTCGGAGATTGTGCTTCAACCCATT:::AAATCTCGGGTCTGATCAAGCTACCCGGATCCAAATCTCTGTCCAACCG
AGCTTCGGAGATTGTGCTTCAACCCATTAG::::::GGGTCTGATCAAGCTACCCGGATCCAAATCTCTGTCCAACCG Paralog B – wild-type forward sequence
CGGCTGAGAAATCTTCGGAGATTGTGCTTCAGCCCATTAGAGAAATCTCGGTCTGATCAAGCTACCCGGACCCAAATC

Fig. 8A

Paralog B – sample 9 NHEJs

```
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT::::::::::::::::::::::::::::::::::::::::::::::::::::::::::::::::::::::::::::::::::::::::GCTCAAGCTACCCGGACCCAAATC
CGGCTGAGAAATCTTCGGAGATTGT:::::::::::::::::::::::::::::::::::::::::::::::::::::::::::::::::::::::::::::::::::::::::CTGATCAAGCTACCCGGACCCAAATC
```

Fig. 8B

```
CGGCTGAGAAATCTTCGGAGATTGT:::::::::::::::::::::::::::::::CTGATCAAGCTACCCGGACCCAAATC
CGGCTGAGAAATCTTCGGAGATTGT:::::::::::::::::::::::::::::::CTGATCAAGCTACCCGGACCCAAATC
CGGCTGAGAAATCTTCGGAGATTGTGCTTCAGCCCA::::::::::::::::::::CTGATCAAGCTACCCGGACCCAAATC
CGGCTGAGAAATCTTCGGAGATTGTGCTTCAGCCCA::::::::::::GGGTCTGATCAAGCTACCCGGACCCAAATC
CGGCTGAGAAATCTTCGGAGATTGTGCTTCAGCCCA::::::::::::GGGTCTGATCAAGCTACCCGGACCCAAATC
CGGCTGAGAAATCTTCGGAGATTGTGCTTCAGCCC:::::::AATCTCGGGTCTGATCAAGCTACCCGGACCCAAATC
CGGCTGAGAAATCTTCGGAGATTGTGCTTCAGCCC:::::::AATCTCGGGTCTGATCAAGCTACCCGGACCCAAATC
CGGCTGAGAAATCTTCGGAGATTGTGCTTCAGCCCATT::::::::GTCTGATCAAGCTACCCGGACCCAAATC
CGGCTGAGAAATCTTCGGAGATTGTGCTTCAGCCCATT:::::CGGGTCTGATCAAGCTACCCGGACCCAAATC
CGGCTGAGAAATCTTCGGAGATTGTGCTTCAGCCCATT:::::CGGGTCTGATCAAGCTACCCGGACCCAAATC
CGGCTGAGAAATCTTCGGAGATTGTGCTTCAGCCCATT:::::CGGGTCTGATCAAGCTACCCGGACCCAAATC
CGGCTGAGAAATCTTCGGAGATTGTGCTTCAGCCCATTA::::AGAAATCTCGGGTCTGATCAAGCTACCCGGACCCAAATC
```

Fig. 8C

Note: These proteins were not tested with EPSPS paralog B reporter cell line (SEQ ID NO:11)

```
   1  ATGGCGCAAG CTAGCAGAAT CTGCCAGAAC CCATGTGTTA TCTCCAATCT
  51  CTCCAAATCA AACCAACGCA AATCGCCCTT GTCTGTCTCG ATGAAGACGC
 101  ACCAGATATC TTCGTGGGGG TTGAAGAAGA GTAACAACGG CTCTGTGATT
 151  CGTCCGGTTC GGGTAACGGC GTCTGTTTCC ACGGCTGAGA AATCTTCGGA
 201  GATTGTGCTT CAGCCCATTA GAGAAATCTC GGGTCTGATC AAGCTACCCG
 251  GACCCAAATC TCTGTCCAAT CGAATCCTTC TTCTAGCCGC TCTATCCGAG
 301  GTCGGTTTGC TTCTTTCTTT CTTTGTTAGC TTAGTGTTGC GTTTTTAACG
 351  GCGTGAGATT GAAGAAAGGT TCACACTTTG TTGTGGTGTT ATAGGGAACC
 401  ACTGTAGTTG ACAACTTGTT GAACAGTGAT GACATCAATT ACATGCTTGA
 451  TGCGTTGAAG AAATTGGGGC TTAATGTGGA ACGTGACAGT GAGAATAACC
 501  GTGCGGTTGT TGAAGGATGT GGCGGGATAT TCCCAGCTTC TTTAGATTCC
 551  AAGAGTGATA TCGAGTTGTA CCTTGGGAAT GCTGGAACAG CCATGCGTCC
 601  ACTTACCGCT GCAGTTACTG CTGCAGGTGG CAACGCAAGG TAAGGTTAAG
 651  GAGTGTGATT TTGTTAGTTA GTTTTGTGTT ATGTCAAGAA CCGATCTTGT
 701  CCTCATGCTT TTAGTTCGGT TTATTTTCCA GTTATATTCT TGGTGGGGTG
 751  CCTAGAATGA GGGAAAGGCC TATTGGAGAT TTGGTTGTTG GTCTTAAGCA
 801  GCTTGGTGCT GATGTTAAT GTACTCTTGG AACTAACTGC CCTCCTGTTC
 851  GCGTCAATGC TAATGGTGGC CTTCCGGTG GAAAGGTGAG TTTGTAATCT
 901  CAGCATCTAC TATGTGGAAA GTTGCAGGAA TTTTTGTTCA TCACACTGCG
 951  TTTGCTCGAT ATGATGGCCT TTGTATGGTT TCTTGATTGA CATATTAGAT
1001  ATGATTTGCA TTTTTCAGGT GAAGCTATCT GGTTNAATCA GTAGTCAATA
1051  CTTGACTGCT CTGCTCATGG CAGCTCCTTT AGCTCTTGGA GACGTTGAGA
1101  TTGAGATCGT TGATAAACTG ATCTCTGTTC CGTATGTTGA AATGACATTG
1151  AAGTTGATGG AACGTTTGG TGTTAGTGCC GAGCATAGTG ACAGTTGGGA
1201  TCGTTTCTTT GTCAAGGGCG GTCAGAAATA CAAGTAAGCG TTGTTTCTGA
1251  AATCACTGAA CTTATAGTTA GATTGACAGA AGAGTGACTA ACCAAATGGT
1301  AAAATTTGAT TCAGGTCGCC TGGTAATGCT TACGTAGAAG GTGATGCTTC
1351  TAGTGCTAGT TATTTCTTGG CTGGTGCCGC CATTACTGGT GAGACTGTTA
1401  CTGTTGAAGG TTGTGGAACA ACCAGCCTGC AGGTAACACT AAGTTTATAA
1451  TGAAATTTGC TTAGTTCAAT TTGTTTTTTT GTCTTTCTAA GGCTTTGGCT
1501  AGTTATGTGT AACATATGTT AGAATCTAAG CTCATTTTTG TTGTTGTGAT
1551  GAATCTCAAA GGGAGATGTG AAGTTCGCTG AGGTTCTTGA GAAAATGGGA
1601  TGTAAAGTGT CATGGACAGA GAACAGTGTG ACTGTGACTG GACCATCTAG
1651  AGATGCTTTT GGAATGAGAC ACTTGCGCGC TGTTGATGTC AACATGAACA
1701  AAATGCCTGA TGTAGCCATG ACTCTTGCCG TTGTTGCTCT CTTTGCAGAT
1751  GGTCCAACCA CCATTAGAGA TGGTAAGTAC TCCCTCTAAC CATCTAATTG
1801  AGGTTTTTAA GATTCATAGT CACTTAGTTC TCCTCTCATC CAATCGTTTT
1851  ATCATATATA GTGGCTAGCT GGAGAGTAAA GGAGACAGAA AGGATGATTG
1901  CCATTTGCAC AGAGCTTAGG AAGGTAAAAC AATTTTCTTT CTGTCCCGCT
1951  CTCACTCTCT TGGTTTTATG TGCTCAGTCT AGGTTAAGTT CTGCATAACT
2001  TTTGCGTGCA GCTTGGAGCT ACAGTGGAAG AGGGTTCAGA TTATTGTGTG
2051  ATAACTCCAC CAGCAAAGCT GAAACCGGCG GAGATTGACA CATATGATGA
2101  TCATAGAATG GCAATGGCAT TCTCCCTTGC AGCTTGTGCT GATGTTCCAG
2151  TAACCATCAA AGATCCTGGT TGCACCAGGA AAACTTTCCC TGACTACTTC
2201  CAGGTCCTTG AAAGTATCAC AAAGCACTAA ACAGACCTTA AAGCCCATTT
2251  GTCTTTTCTT TTTGATCCAA TTGGGATCAG TTTCCTCTGT TATCACTGTA
2301  AGATTACGAA AAACAAAGAG TATTAAGATT GTTGCTTGT ACCTTAAACT
2351  GTTTGATGCA ATCGTTGAAT CAGTTTTGGG CCAAGGGC
```

Fig. 10

(SEQ ID NO:12)

```
   1  ATGGCGCAAG CTAGCAGAAT CTGCCATGGC GTGCAGAACC CATGTGTTAT
  51  CATCTCCAAT CTCTCCAAAT CAAACCAAAA CAAATCACCT TTCTCCGTCT
 101  CGCTGAAGAC GCAGCAGTCT CGAGCTTCTT CGTGGGGACT AAAGAAGAGT
 151  GGAACGATGC TAAACGGTTC TGTAATTCGC CCGGTTAAGG TAACAGCTTC
 201  CGTTTCCACG GCCGAGAAAG CTTCAGAGAT TGTGCTTCAA CCAATTAGAG
 251  AAATCTCGGG TCTCATTAAG CTACCCGGAT CCAAATCTCT CTCCAATCGG
 301  ATCCTCCTTC TTGCTGCTCT ATCTGAGGTA CATATACTTG ATTAGTGTTA
 351  GGCCTTTGCT GTGAGATTTT GGGAACTATA GACAATTTAG TAAGAATTTA
 401  TATATTATTT TTAAAAAATT AAAAGCCTAT ATATATATAT ATTTAAAATT
 451  TTCAAAAAAT TATGGAGGTT TGAGACTGAA GAAAGTTTTT TTTTAATTAT
 501  TATTATAGGG AACTACTGTA GTGGACAACT TGTTGAACAG TGATGACATC
 551  AACTACATGC TTGATGCGTT GAAGAAGCTG GGCTTAACG TGGAACGTGA
 601  CAGGGTAAAC AACCGTGCTG TAGTTGAAGG ATGTGGTGGA ATATTCCCAG
 651  CTTCCTTAGA TTCCAAGAGT GATATTGAGT TGTACCTTGG GAATGCAGGA
 701  ACAGCCATGC GTCCACTCAC CGCTGCCGTT ACTGCTGCAG GTGGCAACGC
 751  AAGGTAAAGG TTAAGGAGCT TTTTGTTATT GTCAAGAAAT TGATTTTGTG
 801  TTTGATGCTT TTAGTTTGGT TTGTTTTCTA GTTATGTGCT TGATGGGGTG
 851  CCTAGAATGA GGGAGAGACC TATAGGAGAT TTGGTTGTTG GTCTTAAGCA
 901  GCTTGGTGCT GATGTTGAAT GTACTCTCGG CACTAACTGT CCTCCTGTTC
 951  GTGTCAATGC TAATGGTGGC CTTCCGGTG GAAAGGTGAT CTTGTTTGCA
1001  GCAGTCTTTG TTCATCACAG CCTTTGCTTC ACATTATTAC ATCTTTTAGT
1051  TTGTTGTTGT GACTTGATGG ATCTTAAAAA AAGGAATTGG GAACTGGTGT
1101  GAAAGTGATT AGCAATCTTT CTCGATTCCT TGCAGGGCCG TGGGCATTAC
1151  TAAGTGAAAC ATTAGCCTAT TAACCCCCAA ATATTTTGAA AAAAATTTAG
1201  TATATGGCCC CAAAATAGTT TTTAAGAAAT TAGAAAAACT TTTAATAAAT
1251  CGTCTACGGT CCCCATTTTA GAGCCGACCC TGCTTGTATG GTTTCTTGAG
1301  TGAGATATTT TACATGTTTT GCATTTTCAG GTGAAGCTTT CTGGATCAAT
1351  CAGTAGTCAA TACTTGACTG CCTTGCTCAT GGCAGCTCCT TTAGCTCTTG
1401  GAGACGTGGA GATTGAGATC ATTGATAAAC TGATTTCTGT TCCATATGTT
1451  GAAATGACAT TGAAGTTGAT GGAACGTTTT GGTGTTAGTG CCGAGCATAG
1501  TGATAGCTGG GATCGTTTCT TGTCAAGGG CGGTCAGAAG TACAAGTAAG
```

Fig. 11A

```
1551  AATTCTTTAA ATTAAAGAAT TAGATTGAAG AAAATGACTG ATTAACCAAA
1601  TGGCAAAACT GATTCAGGTC GCCTGGTAAT GCTTATGTAG AAGGTGATGC
1651  TTCTAGTGCT AGCTACTTCT TGGCTGGTGC TGCTATTACC GGTGAAACCG
1701  TCACTGTTGA AGGTTGTGGA ACAACTAGCC TCCAGGTAGT TTCTCCACTC
1751  TGAATCATCA AATATTATAC TCCCTCCGTT TTGTATTAAG TGTCATTTTA
1801  GCTTTTAAAT TTTGTCTCAT TAAAAGTGTC ATTTTACATT TTCAATGTAT
1851  ATATTAAATA AATTTTCCAG TTTTTACTAA TTCATTATAT TAAATAATAT
1901  AAAACAGAAA ATTTAACAAT TATCGTAATT CGTGTGCAAA GTTGATTAGT
1951  TCAAAGTTGT GTGTAACATG TTTTGAAGAA TCTAAGCTCA TTCTCTTTTT
2001  ATTTTTTTTG TGATGAATCC CAAAGGGAGA TGTGAAATTC GCAGAGGTAC
2051  TTGAGAAAAT GGGATGTAAA GTGTCATGGA CAGAGAACAG TGTGACTGTG
2101  ACTGGACCAT CTAGAGATGC TTTTGGAATG AGACACTTGC GTGCTGTTGA
2151  TGTCAACATG AATAAAATGC CCGATGTAGC CATGACTCTT GCCGTTGTTG
2201  CTCTCTTTGC CGATGGTCCA ACCACCATCA GAGATGGTAA AGCAAAACCC
2251  TCTCTTTGAA TCAGCGTCTT TTAAAAGATT CATGGTTGCT TTAACTCTAT
2301  TTGGTCAATG TAGTGGCTAG CTGGAGAGTT AAGGAGACAG AAAGGATGAT
2351  AGCCATCTGC ACAGAGCTTC GAAAGGTAAG TTTCCTTTTC TCTCATGCTC
2401  TCATTCTAAG TTAATCGTTG CATAACTTTT TGGGGTTTTT TTTTGCGTT
2451  CAGCTTGGAG CTACAGTGGA AGAAGGTTCA GATTATTGTG TGATAACTCC
2501  ACCAGCGAAG GTGAAACCGG CGGAGATTGA TACGTATGAT GATCATAGAA
2551  TGGCGATGGC GTTCTCGCTT GCAGCATGTG CTGATGTTCC AGTCACCATC
2601  AAGGATCCTG GCTGCACCAG AAAGACTTTC CCTGACTACT TTCAAGTCCT
2651  TGAAAGTATC ACAAAGCACT AAAAAGATCA TTTCCTTTGA ATCCAAATGT
2701  GAGAATGTGT TCTTCCTCT CTCTGTTGCC ACTGTAACAT TTATTAGAAG
2751  AACAAAGTGT GTGTGTTTAA GAGTGTGTTT GCTTGTAATG AACTGAGTGA
2801  GATGCAATCG TTGAATCAGT TTTGGGCCAA GGGC
```

Fig. 11B

(SEQ ID NO:13)

```
   1  ATGGCGCAAG CTAGCAGAAT CTGCCATGGC GTGCAGAACC CATGTGTTAT
  51  CATCTCCAAT CTCTCCAAAT CCAACCAAAA CAAATCACCT CTCTCCGTCT
 101  CCTTGAAGAC GCATCAGCCT CGAGCTTCTT CGTGGGGATT GAAGAAGAGT
 151  GGAACGACGC TAAACGGTTC TGTAATTCGC CCGGTTAAGG TAACAGCTTC
 201  TGTTTCCACG TCCGAGAAAG CTTCAGAGAT TGTGCTTCAA CCAATCAGAG
 251  AAATCTCGGG TCTCATTAAG CTACCCGGAT CCAAATCTCT CTCCAATCGG
 301  ATCCTCCTTC TTGCCGCTCT ATCTGAGGTA CATATACTTG CTTAGTGTTA
 351  GGCCTTTGCT GTGAGATTTT GGGAACTATA GACAATTTAG TAAGAATTTA
 401  TATATAATTT TTTTAAAAAA AATCAGAAGC CTATATATAT TTAAATTTTT
 451  CCAAAATTTT TGGAGGTTAT AGGCTTGTGT TACACCATTC TAGTCTGCAT
 501  CTTTCGGTTT GAGACTGAAG AATTTTATTT TTTAAAAAAT TATTATAGGG
 551  AACTACTGTA GTGGACAACT TGTTGAACAG TGATGACATC AACTACATGC
 601  TTGATGCGTT GAAGAAGCTG GGGCTTAACG TGGAACGTGA CAGTGTAAAC
 651  AACCGTGCGG TTGTTGAAGG ATGCGGTGGA ATATTCCCAG CTTCCTTAGA
 701  TTCCAAGAGT GATATTGAGT TGTACCTTGG GAATGCAGGA ACAGCCATGC
 751  GTCCACTCAC CGCTGCAGTT ACAGCTGCAG GTGGCAACGC GAGGTAAGGT
 801  TAACGAGTTT TTTGTTATTG TCAAGAAATT GATCTTGTGT TTGATGCTTT
 851  TAGTTTGGTT TGTTTTCTAG TTATGTACTT GATGGGGTGC CTAGAATGAG
 901  GGAAAGACCT ATAGGAGATT TGGTTGTTGG TCTTAAGCAG CTTGGTGCTG
 951  ATGTTGAGTG TACTCTTGGC ACTAACTGTC CTCCTGTTCG TGTCAATGCT
1001  AATGGTGGCC TTCCCGGTGG AAAGGTGATC TTCACATTTA CTCTATGAAT
1051  TGTTTGCAGC AGTCTTTGTT CATCACAGCC TTTGCTTCAC ATTATTTCAT
1101  CTTTTAGTTT GTTGTTATAT TACTTGATGG ATCTTTAAAA AGGAATTGGG
1151  TCTGGTGTGA AAGTGATTAG CAATCTTTCT CGATTCCTTG CAGGGCCGTG
1201  GGCATTACTA AGTGAAACAT TAGCCTATTA ACCCCAAAA TTTTTGAAAA
1251  AAATTTAGTA TATGGCCCCA AAATAGTTTT TAAAAAATTA GAAAACTTT
1301  TAATAAATCG TCTACAGTCC CAAAAATCTT AGAGCCGGCC CTGCTTGTAT
1351  GGTTTCTCGA TTGATATATT AGACTATGTT TTGAATTTTC AGGTGAAGCT
1401  TTCTGGATCG ATCAGTAGTC AGTACTTGAC TGCCCTCCTC ATGGCAGCTC
1451  CTTTAGCTCT TGGAGACGTG GAGATTGAGA TCATTGATAA ACTGATATCT
1501  GTTCCATATG TTGAAATGAC ATTGAAGTTG ATGGAACGTC TTGGTGTTAG
1551  TGCCGAGCAT AGTGATAGCT GGGATCGTTT CTTTGTCAAG GGCGGTCAGA
1601  AGTACAAGTA AGAATTCTTT AAATTAAAGA ATTAGATTGA AGAAAATGAC
1651  TGATTAACCA AATGGCAAAA CTGATTCAGG TCGCCTGGTA ATGCTTATGT
1701  AGAAGGTGAT GCTTCTAGTG CTAGCTACTT CTTGGCTGGT GCTGCTATTA
1751  CCGGTGAAAC CGTCACTGTT GAAGGTTGTG GAACAACTAG CCTCCAGGTA
```

Fig. 12A

```
1801  GTTTCTCCAC TCTGAATCAT CAAATATTAT ACTCCCTCCG TTTTGTATTA
1851  AGTGTCATTT TAGCTTTTAA ATTTTGTCTC ATTAAAAGTG TCATTTTACA
1901  TTTTCAATGT ATATATTAAA TAAATTTTCC AGTTTTTACT AATTCATTAT
1951  ATTAAATAAT ATAAAACAGA AAATTTAACA ATTATCGTAA TTCGTGTGCA
2001  AAGTTGATTA GTTCAAAGTT GTGTGTAACA TGTTTTGAAG AATCTAAGCT
2051  CATTCTCTTC TTATTTTTTT TGTGATGAAT CCCAAAGGGA GATGTGAAAT
2101  TCGCAGAGGT ACTTGAGAAA ATGGGATGTA AAGTGTCATG GACAGAGAAC
2151  AGTGTGACTG TGACTGGACC ATCTAGAGAT GCTTTTGGAA TGAGACACTT
2201  GCGTGCTGTT GATGTCAACA TGAATAAAAT GCCCGATGTA GCCATGACTC
2251  TTGCCGTTGT TGCTCTCTTT GCCGATGGTC AACCACCAT CAGAGATGGT
2301  AAAGCAAAAC CCTCTCTTTG AATCAGCGTC TTTTAAAGA TTCATGGTTG
2351  CTTTAACTCT ATTTGGTCAA TGTAGTGGCT AGCTGGAGAG TTAAGGAGAC
2401  AGAAAGGATG ATAGCCATCT GCACAGAGCT TCGAAAGGTA AGTTTCCTTT
2451  TCTCTCATGC TCTCATTCTA AGTTAATCGT TGCATAACTT TTTGGGGTTT
2501  TTTTTTGCGT TCAGCTTGGA GCTACAGTGG AAGAAGGTTC AGATTATTGT
2551  GTGATAACTC CACCAGCGAA GGTGAAACCG GCGGAGATTG ATACGTATGA
2601  TGATCATAGA ATGGCGATGG CGTTCTCGCT TGCAGCATGT GCTGATGTTC
2651  CAGTCACCAT CAAGGATCCT GGCTGCACCA GAAAGACTTT CCCTGACTAC
2701  TTTCAAGTCC TTGAAAGTAT CACAAAGCAC TAAAAGATC ATTTCCTTTG
2751  AATCCAAATG TGAGAATGTG TTTCTTCCTC TCTCTGTTGC CACTGTAACA
2801  TTTATTAGAA GAACAAAGTG TGTGTGTTTA AGAGTGTGTT TGCTTGTAAT
2851  GAACTGAGTG AGATGCAATC GTTGAATCAG TTTTGGGCC
```

Fig. 12B

(SEQ ID NO:14)

```
   1  ATGGCGCAAG CTAGCAGAAT CTGCCATGGC GTGCAGAACC CATGTGTTAT
  51  CATCTCCAAT CTCTCCAAAT CCAACCAAAA CAAATCACCT TTCTCCGTCT
 101  CCTTGAAGAC GCATCAGCCT CGAGCTTCTT CGTGGGGATT GAAGAAGAGT
 151  GGAACGATGC TAAACGGTTC TGTAATTCGC CCGGTTAAGG TAACAGCTTC
 201  TGTTTCCACG TCCGAGAAAG CTTCAGAGAT TGTGCTTCAA CCAATCAGAG
 251  AAATCTCGGG TCTCATTAAG CTACCCGGAT CCAAATCTCT CTCCAATCGG
 301  ATCCTCCTTC TTGCCGCTCT ATCTGAGGTA CATATACTTG CTTAGTGTTA
 351  GGCCTTTGCT GTGAGATTTT GGGAACTATA GACAATTTAG TAAGAATTTA
 401  TATATAATTT TTTTAAAAAA AATCAGAAGC CTATATATAT TTAAATTTTT
 451  CCAAAATTTT TGGAGGTTAT AGGCTTATGT TACACCATTC TAGTCTGCAT
 501  CTTTCGGTTT GAGACTGAAG AATTTTATTT TTTAAAAAAT TATTATAGGG
 551  AACTACTGTA GTGGACAACT TGTTGAACAG TGATGACATC AACTACATGC
 601  TTGATGCGTT GAAGAAGCTG GGGCTTAACG TGGAACGTGA CAGTGTAAAC
 651  AACCGTGCGG TTGTTGAAGG ATGCGGTGGA ATATTCCCAG CTTCCTTAGA
 701  TTCCAAGAGT GATATTGAGT TGTACCTTGG GAATGCAGGA ACAGCCATGC
 751  GTCCACTCAC CGCTGCAGTT ACAGCTGCAG GTGGCAACGC GAGGTAAGGT
 801  TAACGAGTTT TTTGTTATTG TCAAGAAATT GATCTTGTGT TTGATGCTTT
 851  TAGTTTGGTT TGTTTTCTAG TGATGTACTT GATGGGGTGC CTAGAATGAG
 901  GGAAAGACCT ATAGGAGATT TGGTTGTTGG TCTTAAGCAG CTTGGTGCTG
 951  ATGTTGAGTG TACTCTTGGC ACTAACTGTC CTCCTGTTCG TGTCAATGCT
1001  AATGGTGGCC TTCCCGGTGG GAAGGTGATC TTCACATTTA CTCTATGAAT
1051  TGTTTGCAGC AGTCTTTGTT CATCACAGCC TTTGCTTCAC ATTATTTCAT
1101  CTTTTAGTTT GTTGTTATAT TACTTGATGG ATCTTTAAAA AGGAATTGGG
1151  TCTGGTGTGA AAGTGATTAG CAATCTTTCT CGATTCCTTG CAGGGCCGTG
1201  GGCATTACTA AGTGAAACAT TAGCCTATTA ACCCCAAAA TTTTGAAAA
1251  AAATTTAGTA TATGGCCCCA AATAGTTTT TAAAAATTA GAAAAACTTT
1301  TAATAAATCG TCTACAGTCC CAAAAATCTT AGAGCCGGCC CTGCTTGTAT
1351  GGTTTCTCGA TTGATATATT AGACTATGTT TTGAATTTTC AGGTGAAGCT
1401  TCCTGGATCG ATCAGTAGTC AGTACTTGAC TGCCCTCCTC ATGGCAGCTC
1451  CTTTAGCTCT GGAGACGTG GAGATTGAGA TCATTGATAA ACTGATATCT
1501  GTTCCATATG TTGAAATGAC ATTGAAGTTG ATGGAGCGTT TTGGTGTTAG
1551  TGCCGAGCAT AGTGATAGCT GGGATCGTTT CTTTGTCAAG GGCGGTCAGA
1601  AATACAAGTA ATGAGTTCTT TTAAGTTGAG AGTTAGATTG AAGAATGAAT
```

Fig. 13A

```
1651  GACTGATTAA CCAAATGGCA AAACTGATTC AGGTCGCCTG GTAATGCTTA
1701  TGTAGAAGGT GATGCTTCTA GTGCTAGCTA CTTCTTGGCT GGTGCTGCCA
1751  TTACTGGTGA AACTGTTACT GTCGAAGGTT GTGGAACAAC TAGCCTCCAG
1801  GTAGTTTATC CACTCTGAAT CATCAAATAT TATACTCCCT CCGTTTTATG
1851  TTAAGTGTCA TTAGCTTTTA AATTTGTTT CATTAAAAGT GTCATTTTAC
1901  ATTTTCAATG CATATATTAA ATAAATTTTC CAGTTTTTAC TAATTCATTA
1951  ATTAGCAAAA TCAAACAAAA ATTATATTAA ATAATGTAAA ATTCGTAATT
2001  TGTGTGCAAA TACCTTAAAC CTTATGAAAC GGAAACCTTA TGAAACAGAG
2051  GGAGTACTAA TTTTATAATA AATTTGATT AGTTCAAAGT TGTGTATAAC
2101  ATGTTCTGTA AGAATCTAAG CTCATTCTCT TTTTATTTTT TGTGATGAAT
2151  CCCAAAGGGA GATGTGAAAT TCGCAGAGGT TCTTGAGAAA ATGGGATGTA
2201  AGGTGTCATG GACAGAGAAC AGTGTGACTG TGACTGGACC ATCAAGAGAT
2251  GCTTTTGGAA TGAGGCACTT GCGTGCTGTT GATGTCAACA TGAACAAAAT
2301  GCCTGATGTA GCCATGACTC TAGCCGTTGT TGCTCTCTTT GCCGATGGTC
2351  CAACCACCAT CAGAGATGGT AAAGCAAAAC CCTCTCTTTG AATCAGCGTG
2401  TTTTAAAGA TTCATGGTTG CTTAAACTCT ATTTGGTCAA TGTAGTGGCT
2451  AGCTGGAGAG TTAAGGAGAC AGAGAGGATG ATTGCCATTT GCACAGAGCT
2501  TAGAAAGGTA AGTTTCCTTT TCTCTCATGC TCTCTCATTC GAAGTTAATC
2551  GTTGCATAAC TTTTTGCGGT TTTTTTTTT GCGTTCAGCT TGGAGCTACA
2601  GTGGAAGAAG GTTCAGATTA TTGTGTGATA ACTCCACCAG CAAAGGTGAA
2651  ACCGGCGGAG ATTGATACGT ATGATGATCA TAGAATGGCG ATGGCGTTCT
2701  CGCTTGCAGC TTGTGCTGAT GTTCCAGTCA CCATCAAGGA TCCTGGCTGC
2751  ACCAGGAAGA CTTTCCCTGA CTACTTCCAA GTCCTTGAAA GTATCACAAA
2801  GCATTAAAAG ACCCTTTCCT CTGATCCAAA TGTGAGAATC TGTTGCTTTC
2851  TCTTTGTTGC CACCGTAACA TTTATTAGAA GAACAAAGTG TGTGTGTTAA
2901  GAGTGTGTTT GCTTGTAATG AACTGAGTGA GATGCAATCG TTGAATCAGT
2951  TTTGGGCC
```

Fig. 13B

Note: These proteins were not tested with EPSPS paralog B reporter cell line

SEQUENCE LISTING

<160> NUMBER OF SEQ ID NOS: 190

<210> SEQ ID NO 1
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 1
ttggagctac agtggaagaa ggtt                    24

```
<210> SEQ ID NO 2
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 2
cgattgcatc tcactcagtt catta                                          25

<210> SEQ ID NO 3
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 3
gtccacttac agctgcagtt actgctgctg gtggca                              36

<210> SEQ ID NO 4
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 4
atggcgcaag ctagcagaat ctgcc                                          25

<210> SEQ ID NO 5
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 5
atggcgcaag ctagcagaat c                                              21

<210> SEQ ID NO 6
<211> LENGTH: 28
<212> TYPE: DNA
<213> ORGANISM: Artificial Sequence
<220> FEATURE:
<223> OTHER INFORMATION: Synthetic oligonucleotide

<400> SEQUENCE: 6
ccagcagcag cgtggagctt atcagata                                       28

<210> SEQ ID NO 7
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 7
ggcccaaaac tgattcaacg attgc                                          25

<210> SEQ ID NO 8
<211> LENGTH: 20
<212> TYPE: DNA
<213> ORGANISM: Artificial Sequence
<220> FEATURE:
<223> OTHER INFORMATION: Synthetic oligonucleotide
```

<400> SEQUENCE: 8
cgttgccacc agcagcagta          20

<210> SEQ ID NO 9
<211> LENGTH: 32
<212> TYPE: DNA
<213> ORGANISM: Artificial Sequence
<220> FEATURE:
<223> OTHER INFORMATION: Synthetic oligonucleotide

<400> SEQUENCE: 9
gatggtccag tcacagtcac actgttctct gt          32

<210> SEQ ID NO 10
<211> LENGTH: 1571
<212> TYPE: DNA
<213> ORGANISM: B. napus

<400> SEQUENCE: 10

```
gcagcagcgt ggagcttatc agatatcttc gcggggttg aagaagagcg cgatggtgct    60
aaaccgttct gtaactcgtc cggttaaggt tatggcctct gtttccacgg cggagaaagc   120
ttcggagatt gtgcttcaac ccattagaga atctcgggt ctgatcaagc tacccggatc   180
caaatctctg tccaaccgga ttcttcttct tgccgcttta tccgaggttt gcttctttct   240
ttgtttgctt agtgttgcgt ttttaacggc gtgaggatga agaaaggttc tgactttgtt   300
gtggttttat agggaactac tgtagttgac aacttgttga acagtgatga cattaactac   360
atgcttgatg cgttgaacaa gttggggctt aatgtgaaac gtgacagtga gaacaaccgt   420
gcggttgttg aaggatgtgg cgggatattc ccagcttctt tagattctaa gggtgatatc   480
gagttgtacc ttgggaatgc aggaacagcc atgcgtccac ttacagctgc agttactgct   540
gctggtggca acgcaaggta aggttaagga cttattctgt tagttagttt tgattatttt   600
aagaatcggt cttgtactga tgctttttag ttgggtttgt ttaccagtta tgtgcttgat   660
ggggtgccta gaatgaggga aagacctata ggagatttgg ttgttggtct taagcagctt   720
ggtgctgatg ttgaatgtac tcttggtact aactgtcctc ctgttcgtgt caatgctaat   780
ggtggcctgc ccggtggaaa ggtgagtttg taatttcagc atttgctatg tgaaaagttg   840
cagcaatctt tgttcatcac actgcgttag cttgacatga ttttagcttt tgtatggttt   900
cttgattgac acattagaca tgttttttgca tttttcaggt gaagctttct ggatcaatca   960
gtagtcaata cttgactgca ctgctcatgg cagctcccctt agctcttgga gacgttgaga  1020
ttgagatcat tgataaattg atttctgttc catatgttga aatgacattg aagttgatgg  1080
aacgttttgg tgttagtgcc gagcatagtg acagttggga tcgtttcttt gtcaagggcg  1140
gtcagaaata caagtaagag ttgtttctaa aatcactgaa cttataatta gattgacaga  1200
agagtgacta accaaatggt aaaatttgat tcaggtcgcc tggtaatgct tacgtagaag  1260
gtgatgcttc tagtgctagt tatttcttgg ctggtgctgc cattactggt gaaaccgtta  1320
ctgttgaagg ttgtggaaca accagcctgc aggtaacact aagtttataa taaaatttgc  1380
ttagttcaat ttttttttgt ctttctaagg cttggctagt tgtgtcactt gtgtgtaaca  1440
tatgaagaat ctaagtttag tttttttggg tgatgaatct caagggaga gtgaagttc   1500
gctgaggttc ttgagaaaat gggatgtaaa gtgtcatgga cagagaacag tgtgactgtg  1560
actggaccat c                                                      1571
```

<210> SEQ ID NO 11
<211> LENGTH: 2388
<212> TYPE: DNA
<213> ORGANISM: B. napus
<220> FEATURE:
<221> NAME/KEY: misc_feature
<222> LOCATION: (1035)..(1035)
<223> OTHER INFORMATION: n is a, c, g, or t

<400> SEQUENCE: 11

```
atggcgcaag ctagcagaat ctgccagaac ccatgtgtta tctccaatct ctccaaatca      60
aaccaacgca aatcgccctt gtctgtctcg atgaagacgc accagatatc ttcgtggggg     120
ttgaagaaga gtaacaacgg ctctgtgatt cgtccggttc gggtaacggc gtctgtttcc     180
acggctgaga atcttcgga gattgtgctt cagcccatta gagaaatctc gggtctgatc     240
aagctacccg gacccaaatc tctgtccaat cgaatccttc ttctagccgc tctatccgag     300
gtcggtttgc ttctttcttt ctttgttagc ttagtgttgc gttttttaacg gcgtgagatt     360
gaagaaaggt tcacactttg ttgtggtgtt atagggaacc actgtagttg acaacttgtt     420
gaacagtgat gacatcaatt acatgcttga tgcgttgaag aaattggggc ttaatgtgga     480
acgtgacagt gagaataacc gtgcggttgt tgaaggatgt ggcgggatat tcccagcttc     540
tttagattcc aagagtgata tcgagttgta ccttgggaat gctggaacag ccatgcgtcc     600
acttaccgct gcagttactg ctgcaggtgg caacgcaagg taaggttaag gagtgtgatt     660
tgttagtta gttttgtgtt atgtcaagaa ccgatcttgt cctcatgctt ttagttcggt     720
ttattttcca gttatattct tggtggggtg cctagaatga gggaaaggcc tattggagat     780
tggttgttg gtcttaagca gcttggtgct gatgttgaat gtactcttgg aactaactgc     840
cctcctgttc gcgtcaatgc taatggtggc cttcccggtg gaaggtgag tttgtaatct     900
cagcatctac tatgtggaaa gttgcaggaa ttttgttca tcacactgcg tttgctcgat     960
atgatggcct ttgtatggtt tcttgattga catattgat atgatttgca ttttcaggt     1020
gaagctatct ggttnaatca gtagtcaata cttgactgct ctgctcatgg cagctccttt    1080
agctcttgga gacgttgaga ttgagatcgt tgataaactg atctctgttc cgtatgttga    1140
aatgacattg aagttgatgg aacgttttgg tgttagtgcc gagcatagtg acagttggga    1200
tcgtttcttt gtcaagggcg gtcagaaata caagtaagcg ttgttttctga atcactgaa    1260
cttatagtta gattgacaga agagtgacta accaaatggt aaaatttgat tcaggtcgcc    1320
tggtaatgct tacgtagaag gtgatgcttc tagtgctagt tatttcttgg ctggtgccgc    1380
cattactggt gagactgtta ctgttgaagg ttgtggaaca accagcctgc aggtaacact    1440
aagtttataa tgaaatttgc ttagttcaat ttgtttttt gtctttctaa ggctttggct    1500
agttatgtgt aacatatgtt agaatctaag ctcattttg ttgttgtgat gaatctcaaa    1560
gggagatgtg aagttcgctg aggttcttga gaaaatggga tgtaaagtgt catggacaga    1620
gaacagtgtg actgtgactg gaccatctag agatgctttt ggaatgagac acttgcgcgc    1680
tgttgatgtc aacatgaaca aaatgcctga tgtagccatg actcttgccg ttgttgctct    1740
ctttgcagat ggtccaacca ccattagaga tggtaagtac tccctctaac catctaattg    1800
aggtttttaa gattcatagt cacttagttc tcctctcatc caatcgtttt atcatatata    1860
gtggctagct ggagagtaaa ggagacagaa aggatgattg ccatttgcac agagcttagg    1920
aaggtaaaac aatttttctttt ctgtcccgct ctcactctct tggttttatg tgctcagtct    1980
aggttaagtt ctgcataact tttgcgtgca gcttggagct acagtggaag agggttcaga    2040
```

| | |
|---|---|
| ttattgtgtg ataactccac cagcaaagct gaaaccggcg gagattgaca catatgatga | 2100 |
| tcatagaatg gcaatggcat tctcccttgc agcttgtgct gatgttccag taaccatcaa | 2160 |
| agatcctggt tgcaccagga aaactttccc tgactacttc caggtccttg aaagtatcac | 2220 |
| aaagcactaa acagaccttta aagcccattt gtcttttctt tttgatccaa ttgggatcag | 2280 |
| tttcctctgt tatcactgta agattacgaa aaacaaagag tattaagatt gtttgcttgt | 2340 |
| accttaaact gtttgatgca atcgttgaat cagttttggg ccaagggc | 2388 |

<210> SEQ ID NO 12
<211> LENGTH: 2834
<212> TYPE: DNA
<213> ORGANISM: B. napus

<400> SEQUENCE: 12

| | |
|---|---|
| atggcgcaag ctagcagaat ctgccatggc gtgcagaacc catgtgttat catctccaat | 60 |
| ctctccaaat caaccaaaa caaatcacct ttctccgtct cgctgaagac gcagcagtct | 120 |
| cgagcttctt cgtggggact aaagaagagt ggaacgatgc taaacggttc tgtaattcgc | 180 |
| ccggttaagg taacagcttc cgtttccacg gccgagaaag cttcagagat gtgcttcaa | 240 |
| ccaattagag aaatctcggg tctcattaag ctacccggta ccaaatctct ctccaatcgg | 300 |
| atcctccttc ttgctgctct atctgaggta catatacttg attagtgtta ggcctttgct | 360 |
| gtgagatttt gggaactata gacaatttag taagaattta tatattattt ttaaaaaatt | 420 |
| aaaagcctat atatatatat atttaaaatt ttcaaaaaat tatggaggtt tgagactgaa | 480 |
| gaaagttttt ttttaattat tattataggg aactactgta gtggacaact tgttgaacag | 540 |
| tgatgacatc aactacatgc ttgatgcgtt gaagaagctg gggcttaacg tggaacgtga | 600 |
| cagggtaaac aaccgtgctg tagttgaagg atgtggtgga atattcccag cttccttaga | 660 |
| ttccaagagt gatattgagt tgtaccttgg gaatgcagga acagccatgc gtccactcac | 720 |
| cgctgccgtt actgctgcag gtggcaacgc aaggtaaagg ttaaggagct ttttgttatt | 780 |
| gtcaagaaat tgattttgtg tttgatgctt ttagtttggt ttgttttcta gttatgtgct | 840 |
| tgatggggtg cctagaatga gggagagacc tataggagat ttggttgttg gtcttaagca | 900 |
| gcttggtgct gatgttgaat gtactctcgg cactaactgt cctcctgttc gtgtcaatgc | 960 |
| taatggtggc cttcccggtg aaaggtgat cttgtttgca gcagtctttg ttcatcacag | 1020 |
| cctttgcttc acattattac atcttttagt ttgttgttgt gacttgatgg atcttaaaaa | 1080 |
| aaggaattgg gaactggtgt gaaagtgatt agcaatcttt ctcgattcct tgcagggccg | 1140 |
| tgggcattac taagtgaaac attagcctat aaccccccaa atattttgaa aaaaatttag | 1200 |
| tatatggccc caaatagtt tttaagaaat tagaaaaact tttaataaat cgtctacggt | 1260 |
| ccccattta gagccgaccc tgcttgtatg gtttcttgag tgagatattt tacatgttt | 1320 |
| gcatttttcag gtgaagcttt ctggatcaat cagtagtcaa tacttgactg ccttgctcat | 1380 |
| ggcagctcct ttagctcttg gagacgtgga gattgagatc attgataaac tgatttctgt | 1440 |
| tccatatgtt gaaatgacat tgaagttgat ggaacgtttt ggtgttagtg ccgagcatag | 1500 |
| tgatagctgg gatcgtttct ttgtcaaggg cggtcagaag tacaagtaag aattcttaa | 1560 |
| attaaagaat tagattgaag aaaatgactg attaaccaaa tggcaaaact gattcaggtc | 1620 |
| gcctggtaat gcttatgtag aaggtgatgc ttcagtgct agctacttct tggctggtgc | 1680 |
| tgctattacc ggtgaaaccg tcactgttga aggttgtgga acaactagcc tccaggtagt | 1740 |
| ttctccactc tgaatcatca aatattatac tccctccgtt ttgtattaag tgtcattta | 1800 |

```
gcttttaaat tttgtctcat taaaagtgtc attttacatt ttcaatgtat atattaaata    1860
aattttccag tttttactaa ttcattatat taaataatat aaaacagaaa atttaacaat    1920
tatcgtaatt cgtgtgcaaa gttgattagt tcaaagttgt gtgtaacatg ttttgaagaa    1980
tctaagctca ttctcttttt attttttttg tgatgaatcc caaagggaga tgtgaaattc    2040
gcagaggtac ttgagaaaat gggatgtaaa gtgtcatgga cagagaacag tgtgactgtg    2100
actgaccat ctagagatgc ttttggaatg agacacttgc gtgctgttga tgtcaacatg     2160
aataaaatgc ccgatgtagc catgactctt gccgttgttg ctctctttgc cgatggtcca    2220
accaccatca gagatggtaa agcaaaaccc tctctttgaa tcagcgtctt ttaaaagatt    2280
catggttgct ttaactctat ttggtcaatg tagtggctag ctggagagtt aaggagacag    2340
aaaggatgat agccatctgc acagagcttc gaaaggtaag tttccttttc tctcatgctc    2400
tcattctaag ttaatcgttg cataactttt tggggttttt ttttgcgtt cagcttggag      2460
ctacagtgga agaaggttca gattattgtg tgataactcc accagcgaag gtgaaaccgg    2520
cggagattga tacgtatgat gatcatagaa tggcgatggc gttctcgctt gcagcatgtg    2580
ctgatgttcc agtcaccatc aaggatcctg gctgcaccag aaagactttc cctgactact    2640
ttcaagtcct tgaaagtatc acaaagcact aaaaagatca tttcctttga atccaaatgt    2700
gagaatgtgt tcttcctct ctctgttgcc actgtaacat ttattagaag aacaaagtgt     2760
gtgtgtttaa gagtgtgttt gcttgtaatg aactgagtga gatgcaatcg ttgaatcagt    2820
tttgggccaa gggc                                                      2834
```

<210> SEQ ID NO 13
<211> LENGTH: 2889
<212> TYPE: DNA
<213> ORGANISM: B. napus

<400> SEQUENCE: 13

```
atggcgcaag ctagcagaat ctgccatggc gtgcagaacc catgtgttat catctccaat     60
ctctccaaat ccaaccaaaa caaatcacct ctctccgtct ccttgaagac gcatcagcct    120
cgagcttctt cgtggggatt gaagaagagt ggaacgacgc taaacggttc tgtaattcgc    180
ccggttaagg taacagcttc tgtttccacg tccgagaaag cttcagagat tgtgcttcaa    240
ccaatcagag aaatctcggg tctcattaag ctacccggat ccaaatctct ctccaatcgg    300
atcctccttc ttgccgctct atctgaggta catatacttg cttagtgtta ggcctttgct    360
gtgagatttt gggaactata gacaatttag taagaattta tatataattt ttttaaaaaa    420
aatcagaagc ctatatatat ttaaattttt ccaaattttt tggaggttat aggcttgtgt    480
tacaccattc tagtctgcat ctttcggttt gagactgaag aattttattt tttaaaaaat    540
tattataggg aactactgta gtggacaact tgttgaacag tgatgacatc aactacatgc    600
ttgatgcgtt gaagaagctg gggcttaacg tggaacgtga cagtgtaaac aaccgtgcgg    660
ttgttgaagg atgcggtgga atattcccag cttccttaga ttccaagagt gatattgagt    720
tgtaccttgg gaatgcagga acagccatgc gtccactcac cgctgcagtt acagctgcag    780
gtggcaacgc gaggtaaggt taacgagttt ttgttattg tcaagaaatt gatcttgtgt      840
ttgatgcttt tagtttggtt tgttttctag ttatgtactt gatgggtgc ctagaatgag      900
ggaaagacct ataggagatt tggttgttgg tcttaagcag cttggtgctg atgttgagtg    960
tactcttggc actaactgtc ctcctgttcg tgtcaatgct aatggtggcc ttcccggtgg   1020
```

```
aaaggtgatc ttcacatttta ctctatgaat tgtttgcagc agtctttgtt catcacagcc    1080
tttgcttcac attatttcat cttttagttt gttgttatat tacttgatgg atctttaaaa    1140
aggaattggg tctggtgtga aagtgattag caatctttct cgattccttg cagggccgtg    1200
ggcattacta agtgaaacat tagcctatta accccaaaa tttttgaaaa aaatttagta    1260
tatggcccca aaatagtttt taaaaaatta gaaaaacttt taataaatcg tctacagtcc    1320
caaaaatctt agagccggcc ctgcttgtat ggtttctcga ttgatatatt agactatgtt    1380
ttgaattttc aggtgaagct ttctggatcg atcagtagtc agtacttgac tgccctcctc    1440
atggcagctc ctttagctct tggagacgtg gagattgaga tcattgataa actgatatct    1500
gttccatatg ttgaaatgac attgaagttg atggaacgtc ttggtgttag tgccgagcat    1560
agtgatagct gggatcgttt ctttgtcaag ggcggtcaga agtacaagta agaattcttt    1620
aaattaaaga attagattga agaaaatgac tgattaacca aatggcaaaa ctgattcagg    1680
tcgcctggta atgcttatgt agaaggtgat gcttctagtg ctagctactt cttggctggt    1740
gctgctatta ccggtgaaac cgtcactgtt gaaggttgtg aacaactag cctccaggta    1800 gtttctccac tctgaatcat caaatattat actccctccg ttttgtatta agtgtcattt    1860
tagcttttaa attttgtctc attaaaagtg tcattttaca ttttcaatgt atatattaaa    1920
taaattttcc agtttttact aattcattat attaaataat ataaacaga aatttaaca    1980 attatcgtaa ttcgtgtgca aagttgatta gttcaaagtt gtgtgtaaca tgttttgaag    2040
aatctaagct cattctcttc ttatttttt tgtgatgaat cccaaaggga gatgtgaaat    2100
tcgcagaggt acttgagaaa atgggatgta aagtgtcatg gacagagaac agtgtgactg    2160
tgactggacc atctagagat gcttttggaa tgagacactt gcgtgctgtt gatgtcaaca    2220
tgaataaaat gcccgatgta gccatgactc ttgccgttgt tgctctcttt gccgatggtc    2280
caaccaccat cagagatggt aaagcaaaac cctctctttg aatcagcgtc ttttaaaaga    2340
ttcatggttg ctttaactct atttggtcaa tgtagtggct agctggagag ttaaggagac    2400
agaaaggatg atagccatct gcacagagct tcgaaaggta agtttccttt tctctcatgc    2460
tctcattcta agttaatcgt tgcataactt ttttggggttt tttttttgcgt tcagcttgga    2520 gctacagtgg aagaaggttc agattattgt gtgataactc caccagcgaa ggtgaaaccg    2580
gcggagattg atacgtatga tgatcataga atggcgatgg cgttctcgct tgcagcatgt    2640
gctgatgttc cagtcaccat caaggatcct ggctgcacca gaaagacttt ccctgactac    2700
tttcaagtcc ttgaaagtat cacaaagcac taaaaagatc atttcctttg aatccaaatg    2760
tgagaatgtg tttcttcctc tctctgttgc cactgtaaca tttattagaa gaacaaagtg    2820
tgtgtgttta agagtgtgtt tgcttgtaat gaactgagtg agatgcaatc gttgaatcag    2880
ttttgggcc                                                             2889
```

<210> SEQ ID NO 14
<211> LENGTH: 2958
<212> TYPE: DNA
<213> ORGANISM: B. napus

<400> SEQUENCE: 14

```
atggcgcaag ctagcagaat ctgccatggc gtgcagaacc catgtgttat catctccaat      60
ctctccaaat ccaaccaaaa caaatcacct ttctccgtct ccttgaagac gcatcagcct     120
cgagcttctt cgtggggatt gaagaagagt ggaacgatgc taaacggttc tgtaattcgc     180
ccggttaagg taacagcttc tgtttccacg tccgagaaag cttcagagat tgtgcttcaa     240
```

```
ccaatcagag aaatctcggg tctcattaag ctacccggat ccaaatctct ctccaatcgg    300
atcctccttc ttgccgctct atctgaggta catatacttg cttagtgtta ggcctttgct    360
gtgagatttt gggaactata gacaatttag taagaattta tatataattt ttttaaaaaa    420
aatcagaagc ctatatatat ttaaattttt ccaaatttt tggaggttat aggcttatgt    480
tacaccattc tagtctgcat cttccggttt gagactgaag aattttattt tttaaaaaat    540
tattataggg aactactgta gtggacaact tgttgaacag tgatgacatc aactacatgc    600
ttgatgcgtt gaagaagctg gggcttaacg tggaacgtga cagtgtaaac aaccgtgcgg    660
ttgttgaagg atgcggtgga atattcccag cttccttaga ttccaagagt gatattgagt    720
tgtaccttgg gaatgcagga acagccatgc gtccactcac cgctgcagtt acagctgcag    780
gtggcaacgc gaggtaaggt taacgagttt tttgttattg tcaagaaatt gatcttgtgt    840
ttgatgcttt tagtttggtt tgttttctag tgatgtactt gatgggtgc ctagaatgag    900 ggaaagacct ataggagatt tggttgttgg tcttaagcag cttggtgctg atgttgagtg    960
tactcttggc actaactgtc ctcctgttcg tgtcaatgct aatggtggcc ttcccggtgg   1020
gaaggtgatc ttcacattta ctctatgaat tgtttgcagc agtctttgtt catcacagcc   1080
tttgcttcac attatttcat cttttagttt gttgttatat tacttgatgg atctttaaaa   1140
aggaattggg tctggtgtga aagtgattag caatctttct cgattccttg cagggccgtg   1200
ggcattacta agtgaaacat tagcctatta accccaaaa ttttgaaaa aaatttagta    1260 tatggcccca aaatagtttt taaaaaatta gaaaaacttt taataaatcg tctacagtcc   1320
caaaaatctt agagccggcc ctgcttgtat ggtttctcga ttgatatatt agactatgtt   1380
ttgaattttc aggtgaagct tcctggatcg atcagtagtc agtacttgac tgccctcctc   1440
atggcagctc ctttagctct tggagacgtg gagattgaga tcattgataa actgatatct   1500
gttccatatg ttgaaatgac attgaagttg atggagcgtt ttggtgttag tgccgagcat   1560
agtgatagct gggatcgttt ctttgtcaag ggcggtcaga aatacaagta atgagttctt   1620
ttaagttgag agttagattg aagaatgaat gactgattaa ccaaatggca aaactgattc   1680
aggtcgcctg gtaatgctta tgtagaaggt gatgcttcta gtgctagcta cttcttggct   1740
ggtgctgcca ttactggtga aactgttact gtcgaaggtt gtggaacaac tagcctccag   1800
gtagtttatc cactctgaat catcaaatat tatactccct ccgttttatg ttaagtgtca   1860
ttagctttta aattttgttt cattaaaagt gtcattttac attttcaatg catatattaa   1920
ataaattttc cagttttta ctaattcatta attagcaaaa tcaaacaaaa attatattaa   1980
ataatgtaaa attcgtaatt tgtgtgcaaa taccttaaac cttatgaaac ggaaaccttta   2040 tgaaacagag ggagtactaa ttttataata aaatttgatt agttcaaagt tgtgtataac   2100
atgttctgta agaatctaag ctcattctct ttttatttt tgtgatgaat cccaaaggga   2160
gatgtgaaat tcgcagaggt tcttgagaaa atgggatgta aggtgtcatg gacagagaac   2220
agtgtgactg tgactggacc atcaagagat gcttttggaa tgaggcactt gcgtgctgtt   2280
gatgtcaaca tgaacaaaat gcctgatgta gccatgactc tagccgttgt tgctctcttt   2340
gccgatggtc caaccaccat cagagatggt aaagcaaaac cctctctttg aatcagcgtg   2400
ttttaaaaga ttcatggttg cttaaactct atttggtcaa tgtagtggct agctggagag   2460
ttaaggagac agagaggatg attgccattt gcacagagct tagaaaggta agtttccttt   2520
tctctcatgc tctctcattc gaagttaatc gttgcataac ttttttgcggt ttttttttt    2580
```

```
gcgttcagct tggagctaca gtggaagaag gttcagatta ttgtgtgata actccaccag    2640
caaaggtgaa accggcggag attgatacgt atgatgatca tagaatggcg atggcgttct    2700
cgcttgcagc ttgtgctgat gttccagtca ccatcaagga tcctggctgc accaggaaga    2760
ctttccctga ctacttccaa gtccttgaaa gtatcacaaa gcattaaaag acccttcct    2820 ctgatccaaa tgtgagaatc tgttgctttc tctttgttgc caccgtaaca tttattagaa    2880
gaacaaagtg tgtgtgttaa gagtgtgttt gcttgtaatg aactgagtga gatgcaatcg    2940
ttgaatcagt tttgggcc                                                  2958
```

```
<210> SEQ ID NO 15
<211> LENGTH: 7
<212> TYPE: PRT
<213> ORGANISM: Artificial Sequence
<220> FEATURE:
<223> OTHER INFORMATION: Synthetic peptide

<400> SEQUENCE: 15

Pro Lys Lys Lys Arg Lys Val
1               5

<210> SEQ ID NO 16
<211> LENGTH: 18
<212> TYPE: PRT
<213> ORGANISM: Thosea asigna virus

<400> SEQUENCE: 16

Glu Gly Arg Gly Ser Leu Leu Thr Cys Gly Asp Val Glu Glu Asn Pro
1               5                   10                  15

Gly Pro

<210> SEQ ID NO 17
<211> LENGTH: 24
<212> TYPE: DNA
<213> ORGANISM: Artificial Sequence
<220> FEATURE:
<223> OTHER INFORMATION: Synthetic oligonucleotide

<400> SEQUENCE: 17
tcccagcttc tttagattct aagg                                            24

<210> SEQ ID NO 18
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 18
ctgcaacttt tcacatagca a                                               21

<210> SEQ ID NO 19
<211> LENGTH: 34
<212> TYPE: DNA
<213> ORGANISM: Artificial Sequence
<220> FEATURE:
<223> OTHER INFORMATION: Synthetic oligonucleotide

<400> SEQUENCE: 19
caagagtgat atcgagttgt accttgggaa tgct                                 34

<210> SEQ ID NO 20
<211> LENGTH: 26
```

```
<212> TYPE: DNA
<213> ORGANISM: Artificial Sequence
<220> FEATURE:
<223> OTHER INFORMATION: Synthetic oligonucleotide

<400> SEQUENCE: 20
aggccatcat atcgagcaaa cgcagt                                          26

<210> SEQ ID NO 21
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 21
gggtaaacaa ccgtgctgta                                                 20

<210> SEQ ID NO 22
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 22
aaagactgct gcaaacaaga tc                                              22

<210> SEQ ID NO 23
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 23
ggttgttgaa ggatgcggt                                                  19

<210> SEQ ID NO 24
<211> LENGTH: 25
<212> TYPE: DNA
<213> ORGANISM: Artificial Sequence
<220> FEATURE:
<223> OTHER INFORMATION: Synthetic oligonucleotide

<400> SEQUENCE: 24
gcaaacaatt catagagtaa atgtg                                           25

<210> SEQ ID NO 25
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ggc, cgc, ggc, cgg, ccg, or gcg

<400> SEQUENCE: 25
nnnagttgta ccttgggaat g                                               21

<210> SEQ ID NO 26
<211> LENGTH: 24
<212> TYPE: DNA
<213> ORGANISM: Artificial Sequence
<220> FEATURE:
```

<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ggc, cgc, ggc, cgg, ccg, or gcg

<400> SEQUENCE: 26
nnnatcaatt tcttgacaat aaca                                          24

<210> SEQ ID NO 27
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ggc, cgg, or gcc

<400> SEQUENCE: 27
nnnatcgagt tgtaccttgg gaatg                                         25

<210> SEQ ID NO 28
<211> LENGTH: 25
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ggc, cgg, or gcc

<400> SEQUENCE: 28
nnnaataagt ccttaacctt acctt                                         25

<210> SEQ ID NO 29
<211> LENGTH: 27
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is cgg, cgc, or gcc

<400> SEQUENCE: 29
nnnagagtga tatcgagttg taccttg                                       27

<210> SEQ ID NO 30
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is cgg, cgc, or gcc

<400> SEQUENCE: 30
nnnacactcc ttaaccttac ctt                                           23

<210> SEQ ID NO 31
<211> LENGTH: 27
<212> TYPE: DNA
<213> ORGANISM: Artificial Sequence

```
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is cgg, ggc, or gcc

<400> SEQUENCE: 31
nnnagagtga tattgagttg taccttg                                          27

<210> SEQ ID NO 32
<211> LENGTH: 24
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is cgg, ggc, or gcc

<400> SEQUENCE: 32
nnnaaagctc cttaaccttt acct                                             24

<210> SEQ ID NO 33
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 33
cagcgtggag cttatcaga                                                   19

<210> SEQ ID NO 34
<211> LENGTH: 22
<212> TYPE: DNA
<213> ORGANISM: Artificial Sequence
<220> FEATURE:
<223> OTHER INFORMATION: Synthetic oligonucleotide

<400> SEQUENCE: 34
gaagagtaac aacggctctg tg                                               22

<210> SEQ ID NO 35
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 35
aaacgcaaca ctaagcaaac                                                  20

<210> SEQ ID NO 36
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ccg, gcg, or cgc

<400> SEQUENCE: 36
nnntctgttt ccacggcgga g                                                21
```

```
<210> SEQ ID NO 37
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ccg, gcg, or cgc

<400> SEQUENCE: 37
nnnaagcggc aagaagaaga atc                                              23

<210> SEQ ID NO 38
<211> LENGTH: 21
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ggc, gcc, or cgg

<400> SEQUENCE: 38
nnntctgttt ccacggctga g                                                21

<210> SEQ ID NO 39
<211> LENGTH: 23
<212> TYPE: DNA
<213> ORGANISM: Artificial Sequence
<220> FEATURE:
<223> OTHER INFORMATION: Synthetic oligonucleotide
<220> FEATURE:
<221> NAME/KEY: misc_feature
<222> LOCATION: (1)..(3)
<223> OTHER INFORMATION: nnn is ggc, gcc, or cgg

<400> SEQUENCE: 39
nnnattggac agagatttgg gtc                                              23

<210> SEQ ID NO 40
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 40
gtccacttac cgctgcagtt actgctgcag gtggca                                36

<210> SEQ ID NO 41
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 41
gtccactcac cgctgcagtt actgctgcag gtggca                                36

<210> SEQ ID NO 42
<211> LENGTH: 36
<212> TYPE: DNA
<213> ORGANISM: Artificial Sequence
<220> FEATURE:
<223> OTHER INFORMATION: Synthetic oligonucleotide
```

-continued

<400> SEQUENCE: 42
gtccactcac cgctgcagtt acagctgcag gtggca                                36

<210> SEQ ID NO 43
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 43
tgccacctgc agcagtaact gcagcggtga gtggac                                36

<210> SEQ ID NO 44
<211> LENGTH: 36
<212> TYPE: DNA
<213> ORGANISM: Artificial Sequence
<220> FEATURE:
<223> OTHER INFORMATION: Synthetic oligonucleotide

<400> SEQUENCE: 44
gtccactcac cgctgcagtt acagctgcag gtggca                                36

<210> SEQ ID NO 45
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 45
ttcaacccat tagagaaatc tcgggtctga                                       30

<210> SEQ ID NO 46
<211> LENGTH: 30
<212> TYPE: DNA
<213> ORGANISM: Artificial Sequence
<220> FEATURE:
<223> OTHER INFORMATION: Synthetic oligonucleotide

<400> SEQUENCE: 46
tcagacccga gatttctcta atgggttgaa                                       30

<210> SEQ ID NO 47
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 47
ttcaacccat tagagaaatc tcgggtctg                                        29

<210> SEQ ID NO 48
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 48
ttcagcccat tagagaaatc tcgggtctg                                        29

<210> SEQ ID NO 49

```
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 49
ttcagcccat tagagaaatc tcgggtctg                                29

<210> SEQ ID NO 50
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 50
ttcaaccaat cagagaaatc tcgggtctc                                29

<210> SEQ ID NO 51
<211> LENGTH: 29
<212> TYPE: DNA
<213> ORGANISM: Artificial Sequence
<220> FEATURE:
<223> OTHER INFORMATION: Synthetic oligonucleotide

<400> SEQUENCE: 51
ttcaaccaat cagagaaatc tcgggtctc                                29

<210> SEQ ID NO 52
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 52
ggaatgcagg aacagccatg cgtccactca ccgctgcagt tacagctgca ggtggcaacg     60
cgaggtaagg ttaacgagtt t                                        81

<210> SEQ ID NO 53
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 53
ggaatgcagg aacagccatg cgtccactca ccgctgcata cagctgcagg tggcaacgcg     60
aggtaaggtt aacgagttt                                           79

<210> SEQ ID NO 54
<211> LENGTH: 78
<212> TYPE: DNA
<213> ORGANISM: Artificial Sequence
<220> FEATURE:
<223> OTHER INFORMATION: Synthetic oligonucleotide

<400> SEQUENCE: 54
aacagccatg cgtccactca ccgctgcagt tacagctgca ggtggcaacg cgaggtaagg     60
ttaacgagtt ttttgtta                                            78

<210> SEQ ID NO 55
<211> LENGTH: 66
```

```
<212> TYPE: DNA
<213> ORGANISM: Artificial Sequence
<220> FEATURE:
<223> OTHER INFORMATION: Synthetic oligonucleotide

<400> SEQUENCE: 55
aacagccatg cgtccactca ccgctgcagt tggcaacgcg aggtaaggtt aacgagtttt    60
ttgtta                                                                66

<210> SEQ ID NO 56
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 56
aacagccatg cgtccactca ccgctgctgc aggtggcaac gcgaggtaag gttaacgagt    60
tttttgtta                                                             69

<210> SEQ ID NO 57
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 57
aacagccatg cgtccactca ccgctgctgc aggtggcaac gcgaggtaag gttaacgagt    60
tttttgtta                                                             69

<210> SEQ ID NO 58
<211> LENGTH: 68
<212> TYPE: DNA
<213> ORGANISM: Artificial Sequence
<220> FEATURE:
<223> OTHER INFORMATION: Synthetic oligonucleotide

<400> SEQUENCE: 58
aacagccatg cgtccactca ccgctgctgc aggtggcaac gcgaggtaag gttaacgagt    60
ttttgtta                                                              68

<210> SEQ ID NO 59
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 59
aacagccatg cgtccactca ccgctgctgc aggtggcaac gcgaggtaag gttaacgtag    60 tttttttgtta                                                           70

<210> SEQ ID NO 60
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 60
aacagccatg cgtccactta cagctgcagg tggcaacgcg aggtaaggtt aacgagtttt    60
``` ttgtta                                                          66

<210> SEQ ID NO 61
<211> LENGTH: 65
<212> TYPE: DNA
<213> ORGANISM: Artificial Sequence
<220> FEATURE:
<223> OTHER INFORMATION: Synthetic oligonucleotide

<400> SEQUENCE: 61
aacagccatg cgtccactta cagctgcagg tggcaacgcg aggtaaggtt aacgagtttt   60
tgtta                                                              65

<210> SEQ ID NO 62
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 62
aaagctcctt aacctttacc ttgcgttgcc acctgcagca gtaacggcag cggtgagtgg   60
acgcatggct gttcctgcat tcccaaggta                                   90

<210> SEQ ID NO 63
<211> LENGTH: 58
<212> TYPE: DNA
<213> ORGANISM: Artificial Sequence
<220> FEATURE:
<223> OTHER INFORMATION: Synthetic oligonucleotide

<400> SEQUENCE: 63
aaagctcctt aacctttacc ttgcgtggac gcatggctgt tcctgcattc ccaaggta     58

<210> SEQ ID NO 64
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 64
agagtgatat tgagttgtac cttgggaatg caggaacagc catgcgtcca ctcaccgctg   60
ccgttactgc tgcaggtggc aacgcaaggt                                   90

<210> SEQ ID NO 65
<211> LENGTH: 84
<212> TYPE: DNA
<213> ORGANISM: Artificial Sequence
<220> FEATURE:
<223> OTHER INFORMATION: Synthetic oligonucleotide

<400> SEQUENCE: 65
agagtgatat tgagttgtac cttggaatgc aggaacagcc atgcgtccac tcaccgctga   60
ctgctgcagg tggcaacgca aggt                                         84

<210> SEQ ID NO 66
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 66

```
agagtgatat tgagttgtac cttgggaatg caggaacagc catgcgtcca ctcaccgctg    60
actgctgcag gtggcaacgc aaggt                                         85
```

<210> SEQ ID NO 67
<211> LENGTH: 85
<212> TYPE: DNA
<213> ORGANISM: Artificial Sequence
<220> FEATURE:
<223> OTHER INFORMATION: Synthetic oligonucleotide

<400> SEQUENCE: 67

```
agagtgatat tgagttgtac cttgggaatg caggaacagc catgcgtcca ctcaccgctg    60
actgctgcag gtggcaacgc aaggt                                         85
```

<210> SEQ ID NO 68
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 68

```
agttgtacct tgggaatgca ggaacagcca tgcgtccact caccgctgca gttacagctg    60
caggtggcaa cgcgaggtaa ggttaacgag                                    90
```

<210> SEQ ID NO 69
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 69

```
agttgtacct tgggaatgca ggaacagcca tgcaggtggc aacgcgaggt aaggttaacg    60
ag                                                                  62
```

<210> SEQ ID NO 70
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 70

```
agttgtacct tgggaatgca ggaacagcca tgcaggtggc aacgcgaggt aaggttaacg    60
ag                                                                  62
```

<210> SEQ ID NO 71
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 71

```
agttgtacct tgggaatgca ggaacagcca tgcaggtggt aacgcgaggt aaggttaacg    60
ag                                                                  62
```

<210> SEQ ID NO 72
<211> LENGTH: 81
<212> TYPE: DNA

<213> ORGANISM: Artificial Sequence
<220> FEATURE:
<223> OTHER INFORMATION: Synthetic oligonucleotide

<400> SEQUENCE: 72
agttgtacct tgggaatgca ggaacagcca tgcgtccact caccgctgct gcaggtggca    60
acgcgaggta aggttaacga g    81

<210> SEQ ID NO 73
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 73
agttgtacct tgggaatgca ggaacagcca tgcgtccact caccgctgct gcaggtggca    60
acgcgaggta aggttaacga g    81

<210> SEQ ID NO 74
<211> LENGTH: 90
<212> TYPE: DNA
<213> ORGANISM: Artificial Sequence
<220> FEATURE:
<223> OTHER INFORMATION: Synthetic oligonucleotide

<400> SEQUENCE: 74
atcaatttct tgacaataac aaaaaactcg ttaaccttac ctcgcgttgc cacctgcagc    60
tgtaactgca gcggtgagtg gacgcatggc    90

<210> SEQ ID NO 75
<211> LENGTH: 83
<212> TYPE: DNA
<213> ORGANISM: Artificial Sequence
<220> FEATURE:
<223> OTHER INFORMATION: Synthetic oligonucleotide

<400> SEQUENCE: 75
atcaatttct tgacaataac aaaaaaacta cgttaacctt acctcgcgtt gccacctgca    60
gcagcggtga gtggacgcat ggc    83

<210> SEQ ID NO 76
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 76
atcaatttct tgacaataac aaaaaactac gttaacctta cctcgcgttg ccacctgcag    60
cagcggtgag tggacgcatg gc    82

<210> SEQ ID NO 77
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 77
atcaatttct tgacaataac aaaaaactac gttaacctta cctcgcgttg ccacctgcag    60
cagcggtgag tggacgcatg gc    82

<210> SEQ ID NO 78
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 78
atcaatttct tgacaataac aaaaaactac gttaacctta cctcgcgttg ccacctgcag      60
cagcggtgag tggacgcatg gc                                              82

<210> SEQ ID NO 79
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 79
atcaatttct tgacaataac aaaaaactac gttaacctta cctcgcgttg ccacctgcag      60
cagcggtgag tggacgcatg gc                                              82

<210> SEQ ID NO 80
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 80
atcaatttct tgacaataac aaaaaactac gttaacctta cctcgcgttg ccacctgcag      60
cagcggtgag tggacgcatg gc                                              82

<210> SEQ ID NO 81
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 81
atcaatttct tgacaataac aaaaaactac gttaacctta cctcgcgttg ccacctgcag      60
cagcggtgag tggacgcatg gc                                              82

<210> SEQ ID NO 82
<211> LENGTH: 82
<212> TYPE: DNA
<213> ORGANISM: Artificial Sequence
<220> FEATURE:
<223> OTHER INFORMATION: Synthetic oligonucleotide

<400> SEQUENCE: 82
atcaatttct tgacaataac aaaaaactac gttaacctta cctcgcgttg ccacctgcag      60
cagcggtgag tggacgcatg gc                                              82

<210> SEQ ID NO 83
<211> LENGTH: 82
<212> TYPE: DNA
<213> ORGANISM: Artificial Sequence
<220> FEATURE:
<223> OTHER INFORMATION: Synthetic oligonucleotide

```
<400> SEQUENCE: 83
atcaatttct tgacaataac aaaaaactac gttaacctta cctcgcgttg ccacctgcag      60
cagcggtgag tggacgcatg gc                                              82

<210> SEQ ID NO 84
<211> LENGTH: 81
<212> TYPE: DNA
<213> ORGANISM: Artificial Sequence
<220> FEATURE:
<223> OTHER INFORMATION: Synthetic oligonucleotide

<400> SEQUENCE: 84
agcttcggag attgtgcttc aacccattag agaaatctcg ggtctgatca agctacccgg      60
atccaaatct ctgtccaacc g                                               81

<210> SEQ ID NO 85
<211> LENGTH: 48
<212> TYPE: DNA
<213> ORGANISM: Artificial Sequence
<220> FEATURE:
<223> OTHER INFORMATION: Synthetic oligonucleotide

<400> SEQUENCE: 85
agcttcggag attgtgcttc aacccggatc caaatctctg tccaaccg                  48

<210> SEQ ID NO 86
<211> LENGTH: 67
<212> TYPE: DNA
<213> ORGANISM: Artificial Sequence
<220> FEATURE:
<223> OTHER INFORMATION: Synthetic oligonucleotide

<400> SEQUENCE: 86
agcttcggag attgtgcttc aacccaggtc tgatcaagct acccggatcc aaatctctgt      60
ccaaccg                                                               67

<210> SEQ ID NO 87
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 87
agcttcggag attgtgcttc aacccatcgg gtctgatcaa gctacccgga tccaaatctc      60
tgtccaaccg                                                            70

<210> SEQ ID NO 88
<211> LENGTH: 70
<212> TYPE: DNA
<213> ORGANISM: Artificial Sequence
<220> FEATURE:
<223> OTHER INFORMATION: Synthetic oligonucleotide

<400> SEQUENCE: 88
agcttcggag attgtgcttc aacccatcgg gtctgatcaa gctacccgga tccaaatctc      60
tgtccaaccg                                                            70

<210> SEQ ID NO 89
<211> LENGTH: 70
<212> TYPE: DNA
<213> ORGANISM: Artificial Sequence
```

<220> FEATURE:
<223> OTHER INFORMATION: Synthetic oligonucleotide

<400> SEQUENCE: 89
agcttcggag attgtgcttc aacccatcgg gtctgatcaa gctacccgga tccaaatctc    60
tgtccaaccg                                                           70

<210> SEQ ID NO 90
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 90
gaaagaaaga agcaaaccga c                                              21

<210> SEQ ID NO 91
<211> LENGTH: 7
<212> TYPE: PRT
<213> ORGANISM: Artificial Sequence
<220> FEATURE:
<223> OTHER INFORMATION: Synthetic peptide

<400> SEQUENCE: 91

Gln Ser Gly Asp Leu Thr Arg
1               5

<210> SEQ ID NO 92
<211> LENGTH: 7
<212> TYPE: PRT
<213> ORGANISM: Artificial Sequence
<220> FEATURE:
<223> OTHER INFORMATION: Synthetic peptide

<400> SEQUENCE: 92

Arg Ser Asp Thr Leu Ser Thr
1               5

<210> SEQ ID NO 93
<211> LENGTH: 7
<212> TYPE: PRT
<213> ORGANISM: Artificial Sequence
<220> FEATURE:
<223> OTHER INFORMATION: Synthetic peptide

<400> SEQUENCE: 93

Arg Asn Asp Asn Arg Ile Thr
1               5

<210> SEQ ID NO 94
<211> LENGTH: 7
<212> TYPE: PRT
<213> ORGANISM: Artificial Sequence
<220> FEATURE:
<223> OTHER INFORMATION: Synthetic peptide

<400> SEQUENCE: 94

Gln Ser Ser Asp Leu Ser Arg
1               5

<210> SEQ ID NO 95
<211> LENGTH: 7
<212> TYPE: PRT
<213> ORGANISM: Artificial Sequence
<220> FEATURE:

<223> OTHER INFORMATION: Synthetic peptide

<400> SEQUENCE: 95

Gln Ser Ser Asp Leu Thr Arg
1               5

<210> SEQ ID NO 96
<211> LENGTH: 7
<212> TYPE: PRT
<213> ORGANISM: Artificial Sequence
<220> FEATURE:
<223> OTHER INFORMATION: Synthetic peptide

<400> SEQUENCE: 96

Asp Arg Ser Asn Leu Ser Arg
1               5

<210> SEQ ID NO 97
<211> LENGTH: 7
<212> TYPE: PRT
<213> ORGANISM: Artificial Sequence
<220> FEATURE:
<223> OTHER INFORMATION: Synthetic peptide

<400> SEQUENCE: 97

Arg Ser Asp Ala Leu Ala Arg
1               5

<210> SEQ ID NO 98
<211> LENGTH: 7
<212> TYPE: PRT
<213> ORGANISM: Artificial Sequence
<220> FEATURE:
<223> OTHER INFORMATION: Synthetic peptide

<400> SEQUENCE: 98

Gln Asn Ala His Arg Lys Thr
1               5

<210> SEQ ID NO 99
<211> LENGTH: 7
<212> TYPE: PRT
<213> ORGANISM: Artificial Sequence
<220> FEATURE:
<223> OTHER INFORMATION: Synthetic peptide

<400> SEQUENCE: 99

Arg Ser Asp His Leu Ser Glu
1               5

<210> SEQ ID NO 100
<211> LENGTH: 7
<212> TYPE: PRT
<213> ORGANISM: Artificial Sequence
<220> FEATURE:
<223> OTHER INFORMATION: Synthetic peptide

<400> SEQUENCE: 100

Asn Ser Arg Asn Arg Lys Thr
1               5

<210> SEQ ID NO 101
<211> LENGTH: 7
<212> TYPE: PRT
<213> ORGANISM: Artificial Sequence
<220> FEATURE:
<223> OTHER INFORMATION: Synthetic peptide

<400> SEQUENCE: 101

Arg Ser Asp His Leu Ser Arg
1               5

<210> SEQ ID NO 102
<211> LENGTH: 7
<212> TYPE: PRT
<213> ORGANISM: Artificial Sequence
<220> FEATURE:
<223> OTHER INFORMATION: Synthetic peptide

<400> SEQUENCE: 102

Gln Ser Ser Asp Leu Arg Arg
1               5

<210> SEQ ID NO 103
<211> LENGTH: 7
<212> TYPE: PRT
<213> ORGANISM: Artificial Sequence
<220> FEATURE:
<223> OTHER INFORMATION: Synthetic peptide

<400> SEQUENCE: 103

Gln Ser Gly Asn Leu Ala Arg
1               5

<210> SEQ ID NO 104
<211> LENGTH: 7
<212> TYPE: PRT
<213> ORGANISM: Artificial Sequence
<220> FEATURE:
<223> OTHER INFORMATION: Synthetic peptide

<400> SEQUENCE: 104

Arg Ser Asp Val Leu Ser Gln
1               5

<210> SEQ ID NO 105
<211> LENGTH: 7
<212> TYPE: PRT
<213> ORGANISM: Artificial Sequence
<220> FEATURE:
<223> OTHER INFORMATION: Synthetic peptide

<400> SEQUENCE: 105

Arg Asn Ala Asn Arg Lys Lys
1               5

<210> SEQ ID NO 106
<211> LENGTH: 7
<212> TYPE: PRT
<213> ORGANISM: Artificial Sequence
<220> FEATURE:
<223> OTHER INFORMATION: Synthetic peptide

<400> SEQUENCE: 106

Arg Ser Asp Asn Leu Ser Thr
1               5

<210> SEQ ID NO 107
<211> LENGTH: 7
<212> TYPE: PRT
<213> ORGANISM: Artificial Sequence
<220> FEATURE:
<223> OTHER INFORMATION: Synthetic peptide

```
<400> SEQUENCE: 107

Arg Asn Asp Ala Arg Ile Thr
1               5

<210> SEQ ID NO 108
<211> LENGTH: 7
<212> TYPE: PRT
<213> ORGANISM: Artificial Sequence
<220> FEATURE:
<223> OTHER INFORMATION: Synthetic peptide

<400> SEQUENCE: 108

Asp Asn Ser Ser Arg Ile Thr
1               5

<210> SEQ ID NO 109
<211> LENGTH: 7
<212> TYPE: PRT
<213> ORGANISM: Artificial Sequence
<220> FEATURE:
<223> OTHER INFORMATION: Synthetic peptide

<400> SEQUENCE: 109

Arg Ser Asp Val Leu Ser Glu
1               5

<210> SEQ ID NO 110
<211> LENGTH: 7
<212> TYPE: PRT
<213> ORGANISM: Artificial Sequence
<220> FEATURE:
<223> OTHER INFORMATION: Synthetic peptide

<400> SEQUENCE: 110

Thr Ser Gly His Leu Ser Arg
1               5

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 111

Arg Ser Asp Asp Leu Ser Lys
1               5

<210> SEQ ID NO 112
<211> LENGTH: 7
<212> TYPE: PRT
<213> ORGANISM: Artificial Sequence
<220> FEATURE:
<223> OTHER INFORMATION: Synthetic peptide

<400> SEQUENCE: 112

Asp Ser Ser Ala Arg Lys Lys
1               5

<210> SEQ ID NO 113
<211> LENGTH: 7
<212> TYPE: PRT
<213> ORGANISM: Artificial Sequence
<220> FEATURE:
<223> OTHER INFORMATION: Synthetic peptide

<400> SEQUENCE: 113
```

Thr Ser Gly Asn Leu Thr Arg
1               5

<210> SEQ ID NO 114
<211> LENGTH: 7
<212> TYPE: PRT
<213> ORGANISM: Artificial Sequence
<220> FEATURE:
<223> OTHER INFORMATION: Synthetic peptide

<400> SEQUENCE: 114

Thr Ser Gly Ser Leu Thr Arg
1               5

<210> SEQ ID NO 115
<211> LENGTH: 7
<212> TYPE: PRT
<213> ORGANISM: Artificial Sequence
<220> FEATURE:
<223> OTHER INFORMATION: Synthetic peptide

<400> SEQUENCE: 115

Arg Ser Asp His Leu Ser Thr
1               5

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide

<400> SEQUENCE: 116

Gln Ser Ala Asn Arg Thr Lys
1               5

<210> SEQ ID NO 117
<211> LENGTH: 7
<212> TYPE: PRT
<213> ORGANISM: Artificial Sequence
<220> FEATURE:
<223> OTHER INFORMATION: Synthetic peptide

<400> SEQUENCE: 117

Arg Ser Asp His Leu Ser Gln
1               5

<210> SEQ ID NO 118
<211> LENGTH: 7
<212> TYPE: PRT
<213> ORGANISM: Artificial Sequence
<220> FEATURE:
<223> OTHER INFORMATION: Synthetic peptide

<400> SEQUENCE: 118

Thr Ser Ser Asn Arg Ile Thr
1               5

<210> SEQ ID NO 119
<211> LENGTH: 7
<212> TYPE: PRT
<213> ORGANISM: Artificial Sequence
<220> FEATURE:
<223> OTHER INFORMATION: Synthetic peptide

<400> SEQUENCE: 119

Asp Arg Ser Ala Leu Ser Arg
1               5

<210> SEQ ID NO 120
<211> LENGTH: 7
<212> TYPE: PRT
<213> ORGANISM: Artificial Sequence
<220> FEATURE:
<223> OTHER INFORMATION: Synthetic peptide

<400> SEQUENCE: 120

His Ser Asp Thr Arg Lys Lys
1               5

<210> SEQ ID NO 121
<211> LENGTH: 7
<212> TYPE: PRT
<213> ORGANISM: Artificial Sequence
<220> FEATURE:
<223> OTHER INFORMATION: Synthetic peptide

<400> SEQUENCE: 121

Arg Ser Asp Asp Leu Ser Glu
1               5

<210> SEQ ID NO 122
<211> LENGTH: 7
<212> TYPE: PRT
<213> ORGANISM: Artificial Sequence
<220> FEATURE:
<223> OTHER INFORMATION: Synthetic peptide

<400> SEQUENCE: 122

Thr Asn Ser Asn Arg Lys Arg
1               5

<210> SEQ ID NO 123
<211> LENGTH: 7
<212> TYPE: PRT
<213> ORGANISM: Artificial Sequence
<220> FEATURE:
<223> OTHER INFORMATION: Synthetic peptide

<400> SEQUENCE: 123

Arg Ser Asp Ser Leu Ser Ala
1               5

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide

<400> SEQUENCE: 124

Thr Ser Ala Asn Leu Ser Arg
1               5

<210> SEQ ID NO 125
<211> LENGTH: 7
<212> TYPE: PRT
<213> ORGANISM: Artificial Sequence
<220> FEATURE:
<223> OTHER INFORMATION: Synthetic peptide

<400> SEQUENCE: 125

Arg Arg Glu Asp Leu Ile Thr

```
<210> SEQ ID NO 126
<211> LENGTH: 7
<212> TYPE: PRT
<213> ORGANISM: Artificial Sequence
<220> FEATURE:
<223> OTHER INFORMATION: Synthetic peptide

<400> SEQUENCE: 126

Thr Ser Ser Asn Leu Ser Arg
1               5

<210> SEQ ID NO 127
<211> LENGTH: 7
<212> TYPE: PRT
<213> ORGANISM: Artificial Sequence
<220> FEATURE:
<223> OTHER INFORMATION: Synthetic peptide

<400> SEQUENCE: 127

Arg Ser Asp Thr Leu Ser Glu
1               5

<210> SEQ ID NO 128
<211> LENGTH: 7
<212> TYPE: PRT
<213> ORGANISM: Artificial Sequence
<220> FEATURE:
<223> OTHER INFORMATION: Synthetic peptide

<400> SEQUENCE: 128

Gln Asn Ala Asn Arg Lys Thr
1               5

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 129

Arg Ser Asp Asn Leu Ser Ala
1               5

<210> SEQ ID NO 130
<211> LENGTH: 7
<212> TYPE: PRT
<213> ORGANISM: Artificial Sequence
<220> FEATURE:
<223> OTHER INFORMATION: Synthetic peptide

<400> SEQUENCE: 130

Gln Asn Arg Asp Arg Lys Asn
1               5

<210> SEQ ID NO 131
<211> LENGTH: 7
<212> TYPE: PRT
<213> ORGANISM: Artificial Sequence
<220> FEATURE:
<223> OTHER INFORMATION: Synthetic peptide

<400> SEQUENCE: 131

Arg Ser Asp Asn Leu Arg Glu
1               5
```

```
<210> SEQ ID NO 132
<211> LENGTH: 7
<212> TYPE: PRT
<213> ORGANISM: Artificial Sequence
<220> FEATURE:
<223> OTHER INFORMATION: Synthetic peptide

<400> SEQUENCE: 132

Arg Ser Ala Ala Leu Ala Arg
1               5

<210> SEQ ID NO 133
<211> LENGTH: 7
<212> TYPE: PRT
<213> ORGANISM: Artificial Sequence
<220> FEATURE:
<223> OTHER INFORMATION: Synthetic peptide

<400> SEQUENCE: 133

Arg Ser Asp Asp Leu Thr Arg
1               5

<210> SEQ ID NO 134
<211> LENGTH: 7
<212> TYPE: PRT
<213> ORGANISM: Artificial Sequence
<220> FEATURE:
<223> OTHER INFORMATION: Synthetic peptide

<400> SEQUENCE: 134

Arg Ser Asp Thr Leu Ser Gln
1               5

<210> SEQ ID NO 135
<211> LENGTH: 7
<212> TYPE: PRT
<213> ORGANISM: Artificial Sequence
<220> FEATURE:
<223> OTHER INFORMATION: Synthetic peptide

<400> SEQUENCE: 135

Gln Ser Gly Ser Leu Thr Arg
1               5

<210> SEQ ID NO 136
<211> LENGTH: 7
<212> TYPE: PRT
<213> ORGANISM: Artificial Sequence
<220> FEATURE:
<223> OTHER INFORMATION: Synthetic peptide

<400> SEQUENCE: 136

Leu Leu Thr Thr Leu Lys Ala
1               5

<210> SEQ ID NO 137
<211> LENGTH: 7
<212> TYPE: PRT
<213> ORGANISM: Artificial Sequence
<220> FEATURE:
<223> OTHER INFORMATION: Synthetic peptide

<400> SEQUENCE: 137

Lys Asn Phe Asn Leu His Gln
1               5
```

<210> SEQ ID NO 138
<211> LENGTH: 7
<212> TYPE: PRT
<213> ORGANISM: Artificial Sequence
<220> FEATURE:
<223> OTHER INFORMATION: Synthetic peptide

<400> SEQUENCE: 138

Thr Ser Thr Gly Leu Leu Ile
1               5

<210> SEQ ID NO 139
<211> LENGTH: 7
<212> TYPE: PRT
<213> ORGANISM: Artificial Sequence
<220> FEATURE:
<223> OTHER INFORMATION: Synthetic peptide

<400> SEQUENCE: 139

Val Ser His Thr Arg Leu Asp
1               5

<210> SEQ ID NO 140
<211> LENGTH: 7
<212> TYPE: PRT
<213> ORGANISM: Artificial Sequence
<220> FEATURE:
<223> OTHER INFORMATION: Synthetic peptide

<400> SEQUENCE: 140

Thr Arg Tyr Lys Leu Met Ser
1               5

<210> SEQ ID NO 141
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 141
ttactgctgc aggtggcaac                                        20

<210> SEQ ID NO 142
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 142
ggcagcggtg agtggacgc                                         19

<210> SEQ ID NO 143
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 143
ttgaagaagc tggggctta                                         19

<210> SEQ ID NO 144
<211> LENGTH: 23
<212> TYPE: DNA

```
<213> ORGANISM: Artificial Sequence
<220> FEATURE:
<223> OTHER INFORMATION: Synthetic oligonucleotide

<400> SEQUENCE: 144
gcatcaagca tgtagttgat gtc                                           23

<210> SEQ ID NO 145
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 145
aaatctcggg tctgat                                                   16

<210> SEQ ID NO 146
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 146
tctaatgggt tgaagc                                                   16

<210> SEQ ID NO 147
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 147
gagatttgga tccggg                                                   16

<210> SEQ ID NO 148
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 148
tccaaccgga ttcttc                                                   16

<210> SEQ ID NO 149
<211> LENGTH: 21
<212> TYPE: DNA
<213> ORGANISM: Artificial Sequence
<220> FEATURE:
<223> OTHER INFORMATION: Synthetic oligonucleotide

<400> SEQUENCE: 149
tgcaggtggc aacgcaagga t                                             21

<210> SEQ ID NO 150
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 150
cagtaacggc agcggtgag                                                19
```

<210> SEQ ID NO 151
<211> LENGTH: 17
<212> TYPE: DNA
<213> ORGANISM: Artificial Sequence
<220> FEATURE:
<223> OTHER INFORMATION: Synthetic oligonucleotide

<400> SEQUENCE: 151
gcagcggtga gtggacg                                           17

<210> SEQ ID NO 152
<211> LENGTH: 19
<212> TYPE: DNA
<213> ORGANISM: Artificial Sequence
<220> FEATURE:
<223> OTHER INFORMATION: Synthetic oligonucleotide

<400> SEQUENCE: 152
tgcagctgta agtggacgc                                         19

<210> SEQ ID NO 153
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 153
ttactgctgc tggtggcaac                                        20

<210> SEQ ID NO 154
<211> LENGTH: 59
<212> TYPE: DNA
<213> ORGANISM: Artificial Sequence
<220> FEATURE:
<223> OTHER INFORMATION: Synthetic oligonucleotide

<400> SEQUENCE: 154
agcttcggag attgtgcttc aacccattag ctacccggat ccaaatctct gtccaaccg    59

<210> SEQ ID NO 155
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 155
agcttcggag attgtgcttc aacccattag ggtctgatca agctacccgg atccaaatct   60
ctgtccaacc g                                                       71

<210> SEQ ID NO 156
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 156
agcttcggag attgtgcttc aacccattaa atctcgggtc tgatcaagct acccggatcc   60
aaatctctgt ccaaccg                                                 77

<210> SEQ ID NO 157

<211> LENGTH: 72
<212> TYPE: DNA
<213> ORGANISM: Artificial Sequence
<220> FEATURE:
<223> OTHER INFORMATION: Synthetic oligonucleotide

<400> SEQUENCE: 157
agcttcggag attgtgcttc aacccattag gggtctgatc aagctacccg gatccaaatc          60
tctgtccaac cg          72

<210> SEQ ID NO 158
<211> LENGTH: 79
<212> TYPE: DNA
<213> ORGANISM: Artificial Sequence
<220> FEATURE:
<223> OTHER INFORMATION: Synthetic oligonucleotide

<400> SEQUENCE: 158
cggctgagaa atcttcggag attgtgcttc agcccattag agaaatctcg ggtctgatca          60
agctacccgg acccaaatc          79

<210> SEQ ID NO 159
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 159
cggctgagaa atcttcggag attgtgctca agctacccgg acccaaatc          49

<210> SEQ ID NO 160
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 160
cggctgagaa atcttcggag attgtgctca agctacccgg acccaaatc          49

<210> SEQ ID NO 161
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 161
cggctgagaa atcttcggag attgtgctca agctacccgg acccaaatc          49

<210> SEQ ID NO 162
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 162
cggctgagaa atcttcggag attgtgctca agctacccgg acccaaatc          49

<210> SEQ ID NO 163
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 163
cggctgagaa atcttcggag attgtgctca agctacccgg acccaaatc          49

<210> SEQ ID NO 164
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 164
cggctgagaa atcttcggag attgtgctca agctacccgg acccaaatc          49

<210> SEQ ID NO 165
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 165
cggctgagaa atcttcggag attgtgctca agctacccgg acccaaatc          49

<210> SEQ ID NO 166
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 166
cggctgagaa atcttcggag attgtgctca agctacccgg acccaaatc          49

<210> SEQ ID NO 167
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 167
cggctgagaa atcttcggag attgtgctca agctacccgg acccaaatc          49

<210> SEQ ID NO 168
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 168
cggctgagaa atcttcggag attgtgctca agctacccgg acccaaatc          49

<210> SEQ ID NO 169
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 169
cggctgagaa atcttcggag attgtgctca agctacccgg acccaaatc          49

<210> SEQ ID NO 170
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 170
cggctgagaa atcttcggag attgtgctca agctacccgg acccaaatc        49

<210> SEQ ID NO 171
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 171
cggctgagaa atcttcggag attgtgctca agctacccgg acccaaatc        49

<210> SEQ ID NO 172
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 172
cggctgagaa atcttcggag attgtgctca agctacccgg acccaaatc        49

<210> SEQ ID NO 173
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 173
cggctgagaa atcttcggag attgtgctca agctacccgg acccaaatc        49

<210> SEQ ID NO 174
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 174
cggctgagaa atcttcggag attgtgctca agctacccgg acccaaatc        49

<210> SEQ ID NO 175
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 175
cggctgagaa atcttcggag attgtgctca agctacccgg acccaaatc        49

<210> SEQ ID NO 176
<211> LENGTH: 49
<212> TYPE: DNA
<213> ORGANISM: Artificial Sequence
<220> FEATURE:
<223> OTHER INFORMATION: Synthetic oligonucleotide

<400> SEQUENCE: 176
cggctgagaa atcttcggag attgtgctca agctacccgg acccaaatc                49

<210> SEQ ID NO 177
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 177
cggctgagaa atcttcggag attgtctgat caagctaccc ggacccaaat c              51

<210> SEQ ID NO 178
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 178
cggctgagaa atcttcggag attgtctgat caagctaccc ggacccaaat c              51

<210> SEQ ID NO 179
<211> LENGTH: 51
<212> TYPE: DNA
<213> ORGANISM: Artificial Sequence
<220> FEATURE:
<223> OTHER INFORMATION: Synthetic oligonucleotide

<400> SEQUENCE: 179
cggctgagaa atcttcggag attgtctgat caagctaccc ggacccaaat c              51

<210> SEQ ID NO 180
<211> LENGTH: 62
<212> TYPE: DNA
<213> ORGANISM: Artificial Sequence
<220> FEATURE:
<223> OTHER INFORMATION: Synthetic oligonucleotide

<400> SEQUENCE: 180
cggctgagaa atcttcggag attgtgcttc agcccactga tcaagctacc cggacccaaa     60
tc                                                                   62

<210> SEQ ID NO 181
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 181
cggctgagaa atcttcggag attgtgcttc agcccagggt ctgatcaagc tacccggacc     60
caaatc                                                               66

<210> SEQ ID NO 182
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 182

```
cggctgagaa atcttcggag attgtgcttc agcccagggt ctgatcaagc tacccggacc    60
caaatc                                                               66

<210> SEQ ID NO 183
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 183
cggctgagaa atcttcggag attgtgcttc agcccaatct cgggtctgat caagctaccc    60
ggacccaaat c                                                         71

<210> SEQ ID NO 184
<211> LENGTH: 71
<212> TYPE: DNA
<213> ORGANISM: Artificial Sequence
<220> FEATURE:
<223> OTHER INFORMATION: Synthetic oligonucleotide

<400> SEQUENCE: 184
cggctgagaa atcttcggag attgtgcttc agcccaatct cgggtctgat caagctaccc    60
ggacccaaat c                                                         71

<210> SEQ ID NO 185
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 185
cggctgagaa atcttcggag attgtgcttc agcccattgt ctgatcaagc tacccggacc    60
caaatc                                                               66

<210> SEQ ID NO 186
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 186
cggctgagaa atcttcggag attgtgcttc agcccattcg ggtctgatca agctacccgg    60
acccaaatc                                                            69

<210> SEQ ID NO 187
<211> LENGTH: 69
<212> TYPE: DNA
<213> ORGANISM: Artificial Sequence
<220> FEATURE:
<223> OTHER INFORMATION: Synthetic oligonucleotide

<400> SEQUENCE: 187
cggctgagaa atcttcggag attgtgcttc agcccattcg ggtctgatca agctacccgg    60
acccaaatc                                                            69

<210> SEQ ID NO 188
<211> LENGTH: 69
<212> TYPE: DNA
<213> ORGANISM: Artificial Sequence
```

-continued

```
<220> FEATURE:
<223> OTHER INFORMATION: Synthetic oligonucleotide

<400> SEQUENCE: 188
cggctgagaa atcttcggag attgtgcttc agcccattcg ggtctgatca agctacccgg    60
acccaaatc                                                           69

<210> SEQ ID NO 189
<211> LENGTH: 66
<212> TYPE: DNA
<213> ORGANISM: Artificial Sequence
<220> FEATURE:
<223> OTHER INFORMATION: Synthetic oligonucleotide

<400> SEQUENCE: 189
cggctgagaa atcttcggag attgtgcttc agcccattat ctgatcaagc tacccggacc    60
caaatc                                                              66

<210> SEQ ID NO 190
<211> LENGTH: 77
<212> TYPE: DNA
<213> ORGANISM: Artificial Sequence
<220> FEATURE:
<223> OTHER INFORMATION: Synthetic oligonucleotide

<400> SEQUENCE: 190
cggctgagaa atcttcggag attgtgcttc agcccattag aaatctcggg tctgatcaag    60
ctacccggac ccaaatc                                                  77
```

US 10,344,289 B2

ENGINEERED ZINC FINGER PROTEINS TARGETING 5-ENOLPYRUVYL SHIKIMATE-3-PHOSPHATE SYNTHASE GENES

CROSS REFERENCE TO RELATED APPLICATIONS

The present application is a continuation application of U.S. patent application Ser. No. 13/766,380, filed Feb. 13, 2013, now allowed, which is a divisional application of U.S. patent application Ser. No. 12/284,888, filed Sep. 25, 2008 which issued as U.S. Pat. No. 8,399,218 on Mar. 19, 2013, which claims the benefit of U.S. Provisional Application No. 60/995,557, filed Sep. 27, 2007, the disclosure of which is hereby incorporated by reference in its entirety.

TECHNICAL FIELD

The disclosure relates generally to the fields of genome engineering, gene targeting, targeted chromosomal integration, and protein expression in plants. In particular, the present disclosure relates to engineered zinc finger proteins that target 5-enolpyruvyl shikimate-3-phosphate synthase (EPSPS) genes and methods of using such zinc finger proteins in modulating gene expression, gene inactivation, and targeted gene modification. More particularly, the disclosure pertains to engineered zinc finger nucleases for targeted cleavage and alteration of EPSPS genes.

BACKGROUND

A major area of interest in agriculture, especially in light of the determination of the complete nucleotide sequences of a number of plant genomes, is the targeted regulation of gene expression and alteration of gene sequences. In particular, the ability to modulate gene expression or modify endogenous plant sequences would facilitate numerous applications such as, for example, the optimization of crop traits affecting nutritional value, yield, stress tolerance, pathogen resistance, oil quality and resistance to agrochemicals and/or the adaptation of plants for use as biological factories for the production of pharmaceutical compounds or industrial chemicals.

Engineered zinc fingers proteins (ZFPs) have been used advantageously to selectively modulate gene expression and for targeted alteration of gene sequences in plants (see, e.g., U.S. Pat. Nos. 7,262,054, 7,235,354, 7,220,719, 7,001,768, and 6,534,261; and U.S. Patent Publication No. 20080182332). Zinc finger proteins (ZFPs) are proteins that bind to DNA, RNA and/or protein, in a sequence-specific manner, by virtue of a metal stabilized domain known as a zinc finger. See, for example, Miller et al. (1985) EMBO J. 4:1609-1614; Rhodes et al. (1993) Sci. Amer. 268(2):56-65; and Klug (1999) J. Mol. Biol. 293:215-218. ZFPs are commonly found in transcription factors, and to date, over 10,000 zinc finger sequences have been identified in several thousand known or putative transcription factors.

Regulation and alteration of selected gene targets can theoretically be achieved by design of ZFPs of predetermined DNA sequence specificity having desired biological activities. Zinc finger domains have been combined, for example, in fusion proteins with regulatory domains to produce engineered zinc finger transcription factors for controlling gene regulation (see, e.g, U.S. Pat. No. 6,534,261). Zinc finger domains have also been combined with nuclease cleavage domains to produce zinc finger nucleases (ZFNs) for specific targeting of a double-stranded break to the region of a genome where modification (e.g., deletion, mutation, homologous recombination, or insertion of an exogenous sequence) is desired (see, e.g., U.S. Patent Application Publication Nos. 2007/0134796 and 2005/0064474). Engineered ZFPs greatly facilitate the insertion of exogenous sequences or modification of endogenous sequences at specific target sites in plants and provide for targeted alteration of plant genomes with greater efficiencies than conventional methods (see, e.g., U.S. Pat. Nos. 7,262,054, 7,235,354, 7,220,719, 7,001,768, and 6,534,261).

However, genome duplication is common in plants and there remains a need for compositions and methods for targeted alteration of such paralogous genes, in plant genomes and modulation of expression of paralogous genes in plants.

SUMMARY

The present disclosure provides compositions and methods for modulating expression and for targeted alteration of one or more paralogous genes (e.g., EPSPS genes) in plant cells. Plant cells can be from monocotyledonous (monocots) or dicotyledonous (dicots) plant species and also include cultured cells, cells in a plant at any stage of development, and plant cells that have been removed from a whole plant and which cells (or their descendants) will be returned to the plant. Plant cells can contain one or more homologous or paralogous gene sequences, any number of which or all of which can be targeted for modification by the methods disclosed herein.

In one aspect, described herein is a zinc finger protein (ZFP) that binds to an EPSPS target genomic region of interest, wherein the ZFP comprises one or more engineered zinc finger binding domains. In certain embodiments, the zinc finger binding domains comprise a sequence as shown in Table A. In certain embodiments, the EPSPS gene targeted by the ZFP comprises a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto. In certain embodiments, the ZFP is a fusion protein comprising one or more regulatory domains. In one embodiment, one or more regulatory domains are selected from the group consisting of a transcriptional repressor, an endonuclease, a methyl transferase, a histone deacetylase, a transcriptional activator, and a histone acetyltransferase. In one embodiment, the ZFP binds to a target sequence of the EPSPS gene, wherein expression of EPSPS is increased or decreased. In one embodiment, the ZFP binds to a transcriptional regulatory sequence of the EPSPS gene. In another embodiment, the ZFP binds upstream of a transcription initiation site of the EPSPS gene. In another embodiment, the ZFP binds adjacent to a transcription initiation site of the EPSPS gene. In another embodiment, the ZFP binds downstream of a transcription initiation site of the EPSPS gene. In one embodiment, the ZFP binds adjacent to an RNA polymerase pause site downstream of a transcription initiation site of the EPSPS gene.

In one embodiment, the ZFP is a zinc finger nuclease (ZFN) that cleaves an EPSPS target genomic region of interest, wherein the ZFN comprises one or more engineered zinc finger binding domains and a nuclease cleavage domain. In certain embodiments, the ZFN comprises a fusion polypeptide comprising an engineered zinc finger binding domain having specificity for an EPSPS gene sequence and a cleavage domain, and/or one or more fusion polypeptides comprising an engineered zinc finger binding domain and a cleavage half-domain. In certain embodiments, the zinc finger binding domains comprises a sequence selected from the group consisting of zinc finger proteins comprising the recognition domains shown in Table A. Cleavage domains and cleavage half domains can be obtained, for example, from various restriction endonucleases and/or homing endonucleases. In one embodiment, the cleavage half-domains are derived from a Type IIS restriction endonuclease (e.g., Fok I). The ZFN may specifically cleave one particular EPSPS gene sequence. Alternatively, the ZFN may cleave two or more homologous EPSPS gene sequences, which may include EPSPS paralogous or orthologous gene sequences.

In certain embodiments, the EPSPS gene targeted by the ZFN comprises a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

The ZFN may bind to and/or cleave an EPSPS gene within the coding region of the gene or in a non-coding sequence within or adjacent to the gene, such as, for example, a leader sequence, trailer sequence or intron, or within a non-transcribed region, either upstream or downstream of the coding region. In certain embodiments, the ZFN binds to and/or cleaves a coding sequence or a regulatory sequence of the EPSPS gene. In certain embodiments, the ZFN binds to and cleaves an EPSPS gene within a region consisting of a nucleotide sequence selected from the group consisting of SEQ ID NOS:10-14.

In another aspect, described herein are compositions comprising one or more ZFPs, which may include one or more ZFNs. Plant cells may contain one unique EPSPS gene or multiple paralogous EPSPS genes. Thus, compositions may comprise one or more ZFPs that target one or more EPSPS genes in a plant cell, for example, 1, 2, 3, 4, 5, or up to any number of EPSPS paralogs or all EPSPS paralogs present in a plant cell. In one embodiment, the composition comprises one or more ZFPs that target all EPSPS paralogous genes in a plant cell. In another embodiment, the composition comprises one ZFP that specifically targets one particular EPSPS paralogous gene in a plant cell. For example, the composition may comprise one ZFN that specifically binds to and cleaves one particular EPSPS paralogous gene in a plant cell, or multiple ZFNs that bind to and cleave two or more EPSPS paralogous genes in a plant cell. Additionally, compositions may contain non-nuclease ZFPs that alter transcriptional regulation of one or more EPSPS paralogous genes.

In another aspect, described herein is a polynucleotide encoding one or more ZFPs described herein. In one embodiment, the polynucleotide encodes at least one ZFN. Exemplary polynucleotides comprise a nucleotide sequence encoding any of the zinc finger proteins as shown in Table A.

In another aspect, described herein is a ZFP expression vector comprising a polynucleotide, encoding one or more ZFPs described herein, operably linked to a promoter. In one embodiment, one or more of the ZFPS are ZFNs.

In another aspect, described herein is a plant host cell comprising one or more ZFP expression vectors. The plant host cell may be stably transformed or transiently transfected or a combination thereof with one or more ZFP expression vectors. In one embodiment, the one or more ZFP expression vectors express one or more ZFNs in the plant host cell.

In another aspect, described herein is a method for cleaving one or more paralogous genes in a plant cell, the method comprising: (a) introducing, into the plant cell, one or more expression vectors encoding one or more ZFNs that bind to a target site in the one or more paralogous genes under conditions such that the ZFN(s) is (are) expressed and the one or more paralogous genes are cleaved. In certain embodiments, the target site is in an EPSPS gene. In one embodiment, one particular EPSPS paralogous gene in a plant cell is cleaved. In another embodiment, more than one EPSPS paralog is cleaved, for example, 2, 3, 4, 5, or up to any number of EPSPS paralogs or all EPSPS paralogs present in a plant cell are cleaved.

In another aspect, described herein is a donor vector comprising first and second DNA sequences, wherein (i) the first sequence is homologous to a third sequence and the second sequence is homologous to a fourth sequence; and (ii) the third and fourth sequences are chromosomal DNA sequences. In certain embodiments, the near edges of third and fourth sequences are separated by at least 1 nucleotide pair. In one embodiment, the third and fourth sequences are endogenous sequences. In another embodiment, the third and fourth sequences are exogenous sequences. In any of the donor vectors the targeted chromosomal DNA sequences may be EPSPS sequences. In certain embodiments, the chromosomal EPSPS DNA sequences belong to an EPSPS gene comprising a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

In certain embodiments, at least one of the first or second sequences in the donor vector has a length of 100 nucleotides or less. In addition, any of the vectors described herein may further comprise a fifth sequence, wherein the fifth sequence: (a) is interposed between the first and second sequences; and (b) is an exogenous sequence. In certain embodiments, the fifth sequence has a size of at least 1 base pair but may be as large as 22 kilobase pairs or more.

The donor vectors (e.g., the fifth sequence) may also comprise sequences encoding a protein or portions of a protein. In certain embodiments, the protein-encoding sequence encodes a selectable marker (e.g., green fluorescent protein (GFP), β-glucuronidase (GUS), phosphinothricin N-acetyl transferase (PAT, BAR), neomycin phosphotransferase, hygromycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase). In other embodiments, the protein-encoding sequence (e.g., the fifth sequence) encodes a protein or portion of protein, for example a sequence that is homologous to chromosomal sequences.

In still other embodiments, the donor vectors (e.g., the fifth sequence) comprise one or more transcriptional regulatory sequences. For example, a donor vector may comprise one or more transcriptional regulatory sequences that increase or decrease expression of the paralogous gene (e.g., EPSPS). In certain embodiments, the donor vector comprises one or more protein targeting sequences that enhance or diminish protein transport.

In still further embodiments, the donor vectors (e.g., fifth sequence) may comprise a wild-type counterpart of a mutant chromosomal sequence (e.g., EPSPS) or, alternatively, a mutant counterpart of a wild-type chromosomal sequence (e.g., EPSPS). In certain embodiments, the mutant chromosomal sequence comprises one or more mutations selected from the group consisting of a point mutation, a substitution, a deletion, and an insertion. In one embodiment, the donor vector comprises a mutant EPSPS chromosomal sequence that increases tolerance of a plant to the herbicide glyphosate.

In any of the donor vectors described herein, the first sequence may have at least 35% homology to the third sequence. Similarly, in any of the vectors described herein, the second sequence may have at least 35% homology to the fourth sequence. In some embodiments the first sequence has at least 35% to 50%, at least 50% to 70%, at least 70% to 80%, at least 80% to 85%, at least 85% to 90%, at least 90% to 95%, at least 95%, 96%, 97%, 98%, 99% or 100% homology to the third sequence. In some embodiments the second sequence has at least 35% to 50%, at least 50% to 70%, at least 70% to 80%, at least 80% to 85%, at least 85% to 90%, at least 90% to 95%, at least 95%, 96%, 97%, 98%, 99% or 100% homology to the fourth sequence.

In yet another aspect, described herein is a method for introducing an exogenous sequence into the genome of a plant cell, the method comprising the steps of: (a) contacting the cell with any of the donor vectors described herein; and (b) expressing one or more zinc finger nucleases in the cell, wherein the one or more zinc finger nucleases cleave chromosomal DNA within between 0.4 and 3 kilobase pairs of either of the third or fourth sequences; such that cleavage of chromosomal DNA in step (b) stimulates incorporation of the donor vector into the genome by homologous recombination. In certain embodiments, the one or more nucleases are fusions between the cleavage domain of a Type IIS restriction endonuclease and an engineered zinc finger binding domain.

In certain embodiments, the zinc finger nucleases cleave an EPSPS gene comprising a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

In another aspect, described herein is a method for expressing the product of an exogenous nucleic acid sequence in a plant cell, the method comprising the steps of: (a) contacting the cell with a donor vector comprising an exogenous nucleic acid sequence; and (b) expressing a zinc finger nuclease (ZFN) in the cell, wherein the ZFN cleaves one or more paralogous genes (e.g., one or more EPSPS genes) in chromosomal DNA within 3 kilobase pairs of either of the third or fourth sequences. Cleavage of the chromosomal DNA in step (b) results in incorporation of the donor vector into the genome by homologous recombination and expression of the product of the exogenous nucleic acid sequence.

In certain embodiments, the zinc finger nuclease cleaves an EPSPS gene comprising a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

In another aspect, described herein is a method for intramolecular homologous recombination in the genome of a plant cell, the method comprising the steps of: (a) providing a DNA segment comprising a sequence of a target gene and further comprising a first sequence that is homologous to a second sequence; and (b) contacting said DNA segment with the ZFN as described herein, wherein the ZFN cleaves the DNA segment at a target gene sequence thereby stimulating intramolecular homologous recombination. In certain embodiments, the DNA segment is endogenous to the cell. In other embodiments, the DNA segment is exogenous to the cell. In certain embodiments, the target gene is unique to the cell. In other embodiments, the target gene is a paralogous gene. In any of these methods the target gene may comprise a unique or paralogous EPSPS gene and the ZFN comprises any of the sequences shown in Table A. In certain embodiments, homologous recombination may occur in a chromosome. In one embodiment, the DNA between the first and second sequences is deleted from the chromosome. In one embodiment, the sequences deleted from the chromosome may encode all or part of the target gene. In another embodiment, the sequences deleted from the chromosome may encode all or part of a selectable marker, for example, green fluorescent protein (GFP), β-glucuronidase (GUS), phosphinothricin N-acetyl transferase (PAT, BAR), neomycin phosphotransferase, hygromycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

In certain embodiments, the deleted DNA is replaced by an exogenous sequence, the method further comprising introducing a polynucleotide into the cell, wherein the polynucleotide comprises (i) fourth and fifth sequences, wherein the fourth sequence is homologous to non-deleted sequences in proximity to the first sequence and the fifth sequence is homologous to non-deleted sequences in proximity to the second sequence; and (ii) the exogenous sequence.

In certain embodiments, the deleted DNA is replaced by a gene sequence, which may comprise a mutant counterpart of a wild-type gene sequence. In certain embodiments, the mutant gene sequence comprises one or more mutations selected from the group consisting of a point mutation, a substitution, a deletion, and an insertion. In one embodiment, the deleted DNA is replaced by an EPSPS gene sequence, for example, an EPSPS gene sequence comprises a mutation that increases tolerance of a plant to the herbicide glyphosate.

In another embodiment, the exogenous sequence may be a selectable marker, for example, green fluorescent protein (GFP), β-glucuronidase (GUS), phosphinothricin N-acetyl transferase (PAT, BAR), neomycin phosphotransferase, hygromycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

In another embodiment, described herein is a method for deleting a gene sequence from the genome of a plant cell, the method comprising (a) providing a plant cell comprising a gene sequence; and (b) expressing first and second zinc finger nucleases (ZFNs) in the cell, wherein the first ZFN cleaves at a first cleavage site and the second ZFN cleaves at a second cleavage site, wherein the gene sequence is located between the first cleavage site and the second cleavage site, wherein cleavage of the first and second cleavage sites results in deletion of the gene sequence. In certain embodiments, the gene sequence is an EPSPS gene.

The size of the deletion in the gene sequence is determined by the distance between the first and second cleavage sites. Accordingly, deletions of any size, in any genomic region of interest, can be obtained. Deletions of 25, 50, 100, 200, 300, 400, 500, 600, 700, 800, 900, 1,000 nucleotide pairs, or any integral value of nucleotide pairs within this range, can be obtained. In addition deletions of a sequence of any integral value of nucleotide pairs greater than 1,000 nucleotide pairs can be obtained using the methods and compositions disclosed herein. In one embodiment, the first and second cleavage sites are separated by at least 100 nucleotides. In one embodiment, an entire gene (e.g., EPSPS) is deleted. In another embodiment, a portion of a gene (e.g., EPSPS) is deleted. In one embodiment, the gene sequence (e.g., EPSPS gene sequence) is deleted from a transgenic plant cell. The gene sequence (e.g., EPSPS) can be an endogenous or an exogenous sequence.

In another aspect, described herein is a method for modulating regulation of a plant gene, the method comprising (a) providing a plant cell comprising an target gene sequence; and (b) expressing a ZFP in the cell, wherein the ZFP binds to a regulatory sequence of the target gene, thereby modulating regulation of the target gene. In certain embodiments, the gene sequence is an EPSPS gene. Binding of the ZFP to the regulatory sequence may increase or decrease transcription of the target (e.g., EPSPS) gene. In certain embodiments, the ZFP also increases or decreases tolerance of a plant to the herbicide glyphosate.

In a still further aspect, a transgenic plant cell obtained according to any of the methods described herein is also provided.

In another aspect, provided herein is a plant comprising a transgenic plant cell obtained as described herein.

In any of the methods described herein, modification of the target plant gene sequences (e.g., transcriptional regulatory sequences or EPSPS coding sequences) can be used to increase or decrease tolerance of a plant to the herbicide glyphosate.

Thus, the present disclosure encompasses, but is not limited to, the following numbered embodiments:

1. A zinc finger protein (ZFP) that binds to an EPSPS target genomic region of interest, said ZFP comprising one or more engineered zinc finger binding domains.
2. The ZFP of embodiment 1, wherein the target genomic region is in cell of a dicotyledonous plant.
3. The ZFP of embodiment 2, wherein the target genomic region is in a cell of a canola plant.
4. The ZFP of embodiment 2, wherein the target genomic region is in a cell of *Brassica* plant.
5. The ZFP of embodiment 1, wherein the EPSPS target genomic region of interest belongs to an EPSPS gene comprising a nucleotide sequence selected from the group consisting of SEQ ID NOS:10-14 or a sequence at least 95% identical thereto.
6. The ZFP of embodiment 1, wherein the ZFP is a fusion protein comprising one or more functional domains.
7. The ZFP of embodiment 6, comprising one or more functional domains selected from the group consisting of a transcriptional repressor, an endonuclease, a methyl transferase, a histone deacetylase, a transcriptional activator, and a histone acetyltransferase.
8. The ZFP of any of embodiments 1-7, wherein the ZFP binds to a transcriptional regulatory sequence of the EPSPS gene.
9. The ZFP of any of embodiments 1-7, wherein the ZFP binds upstream of a transcription initiation site of the EPSPS gene.
10. The ZFP of any of embodiments 1-7, wherein the ZFP binds adjacent to a transcription initiation site of the EPSPS gene.
11. The ZFP of any of embodiments 1-10, wherein the ZFP increases transcription of the EPSPS gene.
12. The ZFP of any of embodiments 1-10, wherein the ZFP decreases transcription of the EPSPS gene.
13. The ZFP of embodiment 1, wherein the ZFP is a zinc finger nuclease (ZFN) that cleaves the EPSPS target genomic region of interest, said ZFN comprising one or more engineered zinc finger binding domains and a nuclease cleavage domain.
14. The ZFN of embodiment 13, wherein the cleavage domain comprises two cleavage half-domains.
15. The ZFN of embodiment 14 wherein the cleavage half-domains are derived from the same nuclease.
16. The ZFN of embodiment 15, wherein the cleavage half domains are derived from a Type IIS restriction endonuclease.
17. The ZFN of embodiment 16, wherein the Type IIS restriction endonuclease is Fok I.
18. The ZFN of embodiment 13, wherein the EPSPS target genomic region of interest belongs to an EPSPS gene comprising a nucleotide sequence selected from the group consisting of SEQ ID NOS:10-14 or a sequence at least 95% identical thereto.
19. The ZFN of embodiment 13, wherein the ZFN binds to a sequence in the coding region of an EPSPS gene.
20. The ZFN of embodiment 13, wherein the ZFN binds to a sequence in the non-coding region of an EPSPS gene.
21. The ZFN of embodiment 20, wherein the ZFN binds to a regulatory sequence of the EPSPS gene.
22. The ZFN of embodiment 13, wherein the ZFN cleaves one or more EPSPS paralogous or orthologous gene sequences.
23. The ZFN of embodiment 13, wherein the ZFN specifically cleaves one EPSPS paralogous or orthologous gene sequence.
24. The ZFN of embodiment 13 comprising a zinc finger binding domain comprising a sequence as shown in Table A.
25. The ZFN of embodiment 13, wherein the ZFN binds to and cleaves an EPSPS gene within a region consisting of a nucleotide sequence selected from the group consisting of SEQ ID NOS:10-14.
26. The ZFN of embodiment 13, wherein the ZFN comprises:
    (a) a first fusion protein comprising a first zinc finger binding domain and a first cleavage half-domain, wherein the first zinc finger binding domain binds to a first nucleotide sequence; and
    (b) a second fusion protein comprising a second zinc finger binding domain and a second cleavage half-domain, wherein the second zinc finger binding domain binds to a second nucleotide sequence.
27. The ZFN of embodiment 26, wherein the second nucleotide sequence is located between 2 and 50 nucleotides from the first nucleotide sequence.
28. The ZFN of embodiment 26, wherein cleavage occurs between the first and second nucleotide sequences.
29. A composition comprising one or more zinc finger proteins (ZFPs) according to any of embodiments 1-28.
30. The composition of embodiment 29, wherein one or more of the ZFPs are zinc finger nucleases (ZFNs).
31. The composition of embodiment 29, comprising one or more ZFPs that target one or more EPSPS genes in a plant cell.

32. The composition of embodiment 29, comprising two or more ZFPs that in combination target all EPSPS paralogous genes in a plant cell.

33. The composition of embodiment 30, comprising one ZFN that specifically binds to and cleaves one EPSPS paralogous gene in a plant cell.

34. The composition of embodiment 30, comprising two or more ZFNs that bind to and cleave two or more EPSPS paralogous genes in a plant cell.

35. The composition of embodiment 30, comprising one or more ZFNs that bind to and cleave all EPSPS paralogous genes in a plant cell.

36. A polynucleotide encoding one or more zinc finger proteins (ZFPs) according to any of embodiments 1 to 28.

37. The polynucleotide of embodiment 36 comprising a nucleotide sequence encoding a zinc finger protein as shown in Table A.

38. A ZFP expression vector comprising the polynucleotide of any of embodiments 36 or 37 operably linked to a promoter.

39. A plant host cell comprising one or more ZFP expression vectors according to embodiment 38.

40. The plant host cell of embodiment 39, wherein the cell is stably transfected with one or more ZFP expression vectors.

41. The plant host cell of embodiment 39, wherein the cell is transiently transfected with one or more ZFP expression vectors.

42. A method for cleaving one or more EPSPS genes in a plant cell, the method comprising:
  (a) transfecting the plant cell with one or more ZFP expression vectors encoding one or more ZFNs according to embodiment 10; and
  (b) expressing the one or more ZFNs in the cell, wherein the ZFNs cleave one or more EPSPS genes.

43. The method of embodiment 42, wherein at least one ZFP expression vector is stably transfected into the plant cell.

44. The method of embodiment 42, wherein at least one ZFP expression vector is transiently transfected into the plant cell.

45. The method of embodiments 42-44 wherein at least two ZFP expression vectors are transfected into the cell.

46. The method of embodiment 45, wherein the at least two ZFP expression vectors are co-transfected into the cell.

47. The method of embodiment 45, wherein the at least two ZFP expression vectors are transfected sequentially into the cell.

48. The method of any of embodiments 42 to 47, wherein all EPSPS paralogous genes in the plant cell are cleaved.

49. The method of any of embodiments 42 to 47, wherein one EPSPS paralogous gene in the plant cell is cleaved.

50. The method of any of embodiments 42 to 47, wherein at least two EPSPS paralogous genes in the plant cell are cleaved.

51. A donor vector comprising first and second DNA sequences;
  wherein the first sequence is homologous to a third sequence and the second sequence is homologous to a fourth sequence; and
  wherein the third and fourth sequences are chromosomal EPSPS DNA sequences.

52. The donor vector of embodiment 51, wherein the near edges of third and fourth sequences are contiguous.

53. The donor vector of embodiment 51, wherein the near edges of the third and fourth sequences are separated by at least 1 nucleotide pair.

54. The vector of any of embodiments embodiment 51 to 53, wherein the chromosomal EPSPS DNA sequences belong to an EPSPS gene comprising a nucleotide sequence selected from the group consisting of SEQ ID NOS:10-14 or a sequence at least 95% identical thereto.

55. The vector of any of embodiments 51 to 54, wherein the third and fourth sequences are exogenous sequences.

56. The vector of any of embodiments 51 to 54, wherein the third and fourth sequences are endogenous sequences.

57. The vector of any of embodiments 51 to 56, wherein at least one of the first or second sequences has a length of 100 nucleotides or less.

58. The vector of any of embodiments 51 to 57, further comprising a fifth sequence, wherein the fifth sequence:
  (a) is interposed between the first and second sequences; and
  (b) is an exogenous nucleic acid sequence.

59. The vector of embodiment 58, wherein the fifth sequence has a size of at least 1 base pair.

60. The vector of embodiment 58 or 59, wherein the fifth sequence comprises sequences encoding a selectable marker.

61. The vector of embodiment 60, wherein the selectable marker is selected from the group consisting of green fluorescent protein (GFP), β-glucuronidase (GUS), phosphinothricin N-acetyl transferase (PAT, BAR), neomycin phosphotransferase, hygromycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

62. The vector of embodiment 58, wherein the fifth sequence comprises sequences encoding a protein other than a selectable marker.

63. The vector of any of embodiments 58 to 62, wherein the fifth sequence comprises one or more transcriptional regulatory sequences.

64. The vector of any of embodiments 58 to 63, wherein the fifth sequence comprises one or more sequences which enhance or diminish protein targeting.

65. The vector of embodiment 63, wherein the one or more transcriptional regulatory sequences increase expression of EPSPS.

66. The vector of embodiment 63, wherein the one or more transcriptional regulatory sequences decrease expression of EPSPS.

67. The vector of any of embodiments 58 to 66, wherein the fifth sequence comprises one or more sequences encoding a portion of a protein or a small interfering RNA or a micro RNA.

68. The vector of embodiment 67, wherein the sequences encoding the portion of the protein comprise sequences homologous to EPSPS chromosomal sequences.

69. The vector of embodiment 58, wherein the fifth sequence comprises a wild-type counterpart of a mutant EPSPS chromosomal sequence.

70. The vector of embodiment 58, wherein the fifth sequence comprises a mutant counterpart of a wild-type EPSPS chromosomal sequence.

71. The vector of embodiment 70, wherein the mutant EPSPS chromosomal sequence increases tolerance of a plant to the herbicide glyphosate.

72. The vector of any of embodiments 51 to 71, wherein the first sequence has at least 35% homology to the third sequence.

73. The vector of any of embodiments 51 to 72, wherein the second sequence has at least 35% homology to the fourth sequence.

74. A method for introducing an exogenous nucleic acid sequence into the genome of a plant cell, the method comprising the steps of:
(a) contacting the cell with a donor vector according to any of embodiments 51 to 73; and
(b) expressing a zinc finger nuclease (ZFN) in the cell, wherein the ZFN cleaves an EPSPS gene in chromosomal DNA within 3 kilobase pairs of either of the third or fourth sequences;
such that cleavage of the chromosomal DNA in step (b) stimulates incorporation of the donor vector into the genome by homologous recombination.

75. The method of embodiment 74, wherein the EPSPS gene comprises a nucleotide sequence selected from the group consisting of SEQ ID NOS:10-14 or a sequence at least 95% identical thereto.

76. A method for expressing the product of an exogenous nucleic acid sequence in a plant cell, the method comprising the steps of:
(a) contacting the cell with the donor vector of embodiment 58-73; and
(b) expressing a zinc finger nuclease (ZFN) in the cell, wherein the ZFN cleaves an EPSPS gene in chromosomal DNA within 3 kilobase pairs of either of the third or fourth sequences;
such that cleavage of the chromosomal DNA in step (b) results in incorporation of the donor vector into the genome by homologous recombination and expression of the product of the exogenous nucleic acid sequence.

77. The method of embodiment 76, wherein the EPSPS gene comprises a nucleotide sequence selected from the group consisting of SEQ ID NOS:10-14 or a sequence at least 95% identical thereto.

78. A transgenic plant cell obtained according to the method of any of embodiments 74 or 75.

79. A plant comprising a transgenic plant cell according to embodiment 78.

80. A method for intramolecular homologous recombination in the genome of a plant cell, the method comprising the steps of:
(a) providing a DNA segment comprising an EPSPS gene and further comprising a first sequence that is homologous to a second sequence; and
(b) contacting said DNA segment with the ZFN of any of embodiments 14 to 28, wherein the ZFN cleaves the DNA segment at an EPSPS gene sequence thereby stimulating intramolecular homologous recombination.

81. The method of embodiment 80, wherein the DNA segment is endogenous to the cell.

82. The method of embodiment 80 or 81, wherein the homologous recombination occurs in a chromosome.

83. The method of embodiment 82, wherein DNA between the first and second sequences is deleted from the chromosome.

84. The method of any of embodiments 80 to 83, wherein the EPSPS gene is unique in the genome.

85. The method of any of embodiments 80 to 83, wherein one or more paralogs of the EPSPS gene are present in the genome.

86. The method of any of embodiments 80 to 85, wherein the ZFN comprises a pair of fusion proteins, wherein each fusion protein is a fusion between the cleavage domain of a Type IIS restriction endonuclease and an engineered zinc finger binding domain.

87. The method of any of embodiments 80 to 86, wherein the second sequence is at least 100 base pairs from the first sequence.

88. The method of any of embodiments 80 to 86, wherein the EPSPS gene sequence is at least 100 base pairs from the first or second sequence.

89. The method of any of embodiments 80 to 86, wherein the EPSPS gene sequence lies between the first and second sequences.

90. The method of any of embodiments 80 to 89, wherein one of the first or second sequences is exogenous to the organism.

91. The method of any of embodiments 80 to 90, wherein both of the first and second sequences are exogenous to the organism.

92. The method of embodiment 83, wherein the sequences deleted from the chromosome encode all or part of an EPSPS gene.

93. The method of embodiment 83, wherein the sequences deleted from the chromosome encode all or part of a selectable marker.

94. The method of embodiment 93, wherein the selectable marker is selected from the group consisting of green fluorescent protein (GFP), β-glucuronidase (GUS), phosphinothricin N-acetyl transferase (PAT, BAR), neomycin phosphotransferase, hygromycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

95. The method of embodiment 83, wherein the deleted DNA is replaced by an exogenous sequence, the method further comprising:
introducing a polynucleotide into the cell, wherein the polynucleotide comprises:
(a) fourth and fifth sequences, wherein the fourth sequence is homologous to non-deleted sequences in proximity to the first sequence and the fifth sequence is homologous to non-deleted sequences in proximity to the second sequence; and
(b) the exogenous sequence.

96. The method of embodiment 95, wherein the exogenous sequence is a selectable marker.

97. The method of embodiment 96, wherein the selectable marker is selected from the group consisting of green fluorescent protein (GFP), β-glucuronidase (GUS), phosphinothricin N-acetyl transferase (PAT, BAR), neomycin phosphotransferase, hygromycin phosphotransferase, β-lactamase, catechol dioxygenase, α-amylase, tyrosinase, β-galactosidase, luciferase, aequorin, EPSP synthase, nitrilase, acetolactate synthase (ALS), dihydrofolate reductase (DHFR), dalapon dehalogenase and anthranilate synthase.

98. The method of embodiment 95, wherein the exogenous sequence is an EPSPS gene sequence.

99. The method of embodiment 98, wherein the EPSPS gene sequence comprises a mutation.

100. The method of embodiment 99, wherein the mutation increases tolerance of a plant to the herbicide glyphosate.

101. A method for deleting an EPSPS gene sequence from the genome of a plant cell, the method comprising:
(a) providing a plant cell comprising an EPSPS gene sequence; and
(b) expressing first and second zinc finger nucleases (ZFNs) in the cell, wherein the first ZFN cleaves at a first cleavage site and the second ZFN cleaves at a second cleavage site, wherein the EPSPS gene sequence is located between the first cleavage site and the second cleavage site, wherein cleavage of the first and second cleavage sites results in deletion of the EPSPS gene sequence.

102. The method of embodiment 101, wherein the EPSPS gene sequence is deleted by non-homologous end joining of first and second cleavage sites.

103. The method of embodiment 101 or 102, wherein the first and second cleavage sites are separated by at least 100 nucleotides.

104. The method of embodiment 101 or 102, wherein the plant cell is a transgenic plant cell.

105. The method of embodiment 101 or 102, wherein the EPSPS gene sequence is an exogenous sequence.

106. The method of embodiment 101 or 102, wherein the EPSPS gene sequence is an endogenous sequence.

107. A method for modulating regulation of an EPSPS gene, the method comprising:
  (a) providing a plant cell comprising an EPSPS gene sequence; and
  (b) expressing a ZFP in the cell, wherein said ZFP binds to a target site in the EPSPS gene, thereby modulating regulation of the EPSPS gene.

108. The method of embodiment 107, wherein the target site is a regulatory sequence of the EPSPS gene.

109. The method of embodiment 107, wherein the target site is upstream of a transcription initiation site of the EPSPS gene.

110. The method of embodiment 107, wherein the target site is adjacent to a transcription initiation site of the EPSPS gene.

111. The method of embodiment 107, wherein the target site is downstream of a transcription initiation site of the EPSPS gene.

112. The method of embodiment 107, wherein the ZFP increases transcription of the EPSPS gene.

113. The method of embodiment 112, wherein the ZFP increases tolerance of a plant to the herbicide glyphosate.

114. The method of embodiment 107, wherein the ZFP decreases transcription of the EPSPS gene.

115. The method of embodiment 114, wherein the ZFP decreases tolerance of a plant to the herbicide glyphosate.

These and other embodiments of the present disclosure will readily occur to those of skill in the art in view of the disclosure herein.

BRIEF DESCRIPTION OF THE DRAWINGS

FIGS. 3A-3D represent paralogs A, B, C and D-specific PCR assays respectively. Lanes 1-6 contained the following DNA. Lane 1: No DNA PCR control; lane 2: *B. napus* variety Nex710 DNA (10 ng/μl); lane 3, 4, 5 and 6 contained amplified DNA of paralogs D, C, B and A (1570 bp) as positive controls at 1 ng/μl concentration. PCR products were run on an 2% E-GEL 96 (Invitrogen, Carlsbad, Calif.) and visualized using the GEL DOC 2000 gel documentation system (Bio-Rad, Hercules, Calif.). The image was captured and analyzed using QUANTITY ONE software (Bio-Rad, Hercules, Calif.) and further processed using E-EDITOR software (Invitrogen, Carlsbad, Calif.). Fragment sizes are shown in base pairs (bp).

FIG. 4 shows the binding and cleavage sites of ZFNs for the *B. napus* EPSPS paralogs. Two ZFN proteins are required to carry out double-stranded (ds) cleavage of DNA. In paralog D, the binding site in for ZFP 10654 is shown in SEQ ID NO:42 and the binding site for ZFP 10657 or ZFP 10658 is shown in SEQ ID NO:43. In paralog A, the binding site in for ZFP 10740 is shown in SEQ ID NO:45 and the binding site for ZFP 10741 or ZFP 10742 is shown in SEQ ID NO:46. Upstream of the cleavage site, indicated with a downward arrow, one protein (10657 or 10658 in paralog D and 10741 or 10742 in paralog A) was bound to nucleotides as underlined, where another protein (10654 in paralog D and 10740 in paralog A) bound downstream to the underlined sequence as shown. Only when both proteins were bound to their respective sites did cleavage occur. Minor sequence differences (underlined) in the binding sites of one or both ZFNs of a pair among the 5 paralogs. For ZFPs 10654 and 10657/10658 the sequence comparisons of the binding sites are as follows: SEQ ID NO: 3 (paralog A), SEQ ID NO:40 (paralog B); SEQ ID NO:41 (paralog C) and SEQ ID NO:42 (paralog D and E)). For ZFPs 10740 and 10741/10742 the sequence comparisons of the binding sites are as follows: SEQ ID NO:45 (paralog A): SEQ ID NO:49 (paralogs B and C); SEQ ID NO:50 (paralog D and E). The ZFNs provided sequence specificity and resulted in selective double-stranded cleavage of the paralogs.

FIG. 6 shows ZFN-mediated double-stranded breaks resulting in NHEJs in *B. napus* EPSPS paralog D. The wild-type sequence is shown in SEQ ID NO:54 and sequences of samples 2, 4 and 5 are shown in SEQ ID NO:55 (sample 2); SEQ ID NO:56 (sample 4); SEQ ID NO:57 (sample 5 (35)); SEQ ID NO:58 (sample 5, 5$^{th}$ line of Figure); SEQ ID NO:59 (sample 5, 6$^{th}$ line of Figure); and SEQ ID NO:60 (sample 5(8) and sample 5, last line of Figure). Alignment of multiple NHEJ deletions with respect to the predicted cleavage site (top) in the wild-type DNA is shown. Numbers in the brackets on the right hand side show the number of identical molecules observed in the alignment.

FIGS. 7A-7B show ZFN-mediated double-stranded breaks resulting in NHEJs in EPSPS paralogs C and D of *B. napus* (SEQ ID NO: 62-83). Alignment of multiple NHEJ deletions with respect to the predicted cleavage site (top) in the wild-type and treated samples are shown. SEQ ID NOs:62 and 64 show the wild type reverse and forward sequences of Paralog C, respectively and the NHEJ modifications of Paralog C are shown in SEQ ID NO:63 (sample 16) and SEQ ID NO:65-67 (sample 17). SEQ ID NOs:68 and 74 show the wild type and reverse sequences of Paralog D, respectively and the NHEJ modifications of Paralog D are shown in SEQ II) NO:69-73 (sample forward sequence) and SEC) ID NO:75-83 (sample 24 NHEJs). The sample numbers correspond to those shown in Table 5.

FIGS. 8A-8C show ZFN-mediated double-stranded breaks resulting in NHEJs in the EPSPS paralogs A and B of B. napus (SEQ ID NOS: 84-89 and 154-190). Alignment of multiple NHEJ deletions with respect to the predicted cleavage site (top) in the wild-type and transgenic samples are shown. In FIG. 8A, SEQ ID NO:84 shows the wild type forward sequence of Paralog A and the NHEJ modifications of Paralog A are shown in SEQ ID NO:85-89 and 154-157 (sample 3 NHEJs). Also shown in FIG. 8A is the wild type forward sequence of Paralog B (SEQ ID NO:158). FIGS. 8B and 8C show NHEJ modifications of Paralog B (SEQ ID NO:159-190 (sample 9 NHEJs)). The sample numbers correspond to those shown in Table 6.

FIG. 9A shows gene correction using ZFN pair 10654 and 10658. FIG. 9B gene correction activity of ZFN pair 10654 and 10658. FIG. 9C shows gene correction activity of ZFN pair 9875 and 10275. FIG. 9E shows gene correction activity for ZFN pairs 10740/10741 and 10749/10742. FIG. 9E shows gene correction activity for the ZFN pairs indicated beneath each bar.

DETAILED DESCRIPTION

Figure 1:
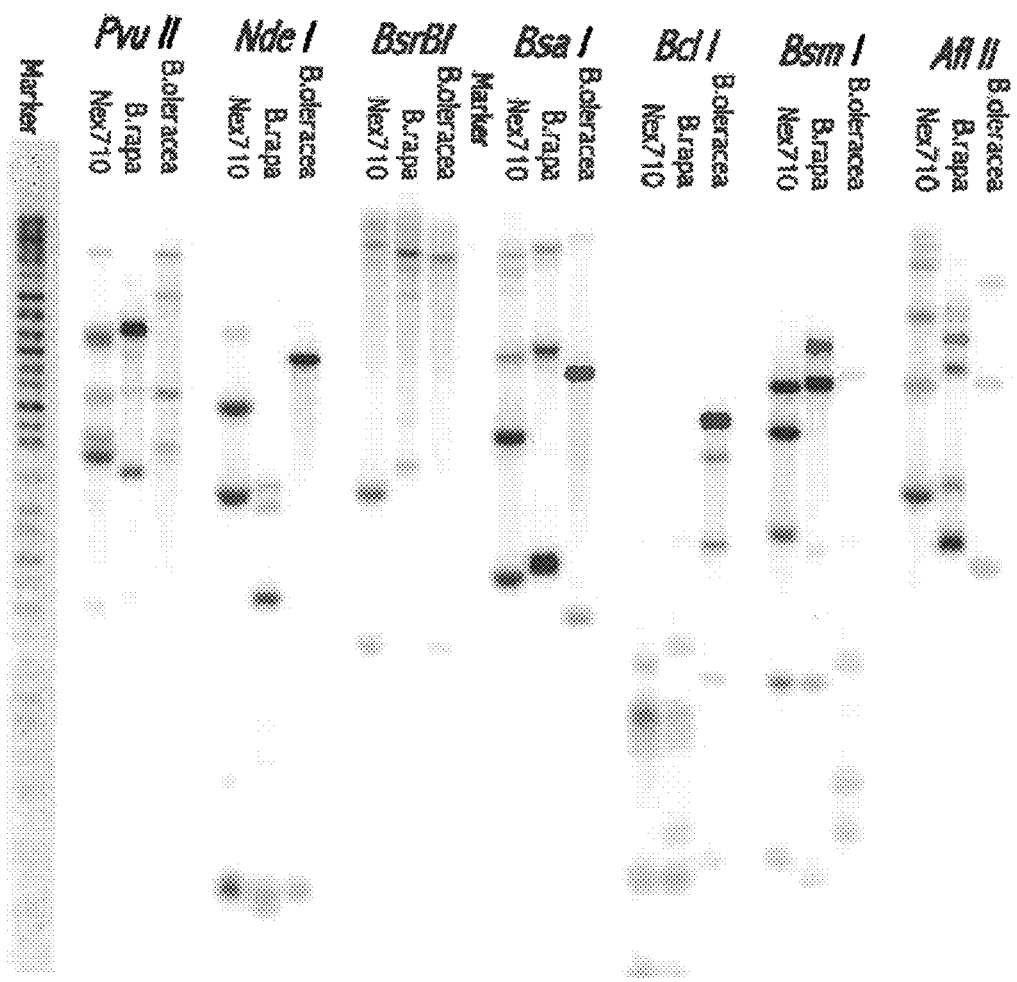
FIG. 1 shows a Southern blot providing an estimation of the number of EPSPS genes in the *B. napus* variety Nex710, *B. rapa* and *B. oleracea* genomes. (Standard markers are Promega's analytical DNA wide range markers.)

Disclosed herein are compositions and methods useful for modulation of expression and targeted cleavage and alteration of genes in plants, particularly paralogous genes in plants. Regulation of a paralogous gene can be modulated, e.g., by using engineered ZFP transcription factors or modifying gene regulatory regions. genes can be altered, e.g., by targeted cleavage followed by intrachromosomal homologous recombination or by targeted cleavage followed by homologous recombination between an exogenous polynucleotide (comprising one or more regions of homology with the gene nucleotide sequence) and a genomic sequence. A non-limiting example of a paralogous gene in plants is the EPSPS gene.

Genomic sequences include those present in chromosomes, episomes, organellar genomes (e.g., mitochondria, chloroplasts), artificial chromosomes and any other type of nucleic acid present in a cell such as, for example, amplified sequences, double minute chromosomes and the genomes of endogenous or infecting bacteria and viruses. Genomic sequences can be normal (i.e., wild-type) or mutant; mutant sequences can comprise, for example, insertions, deletions, translocations, rearrangements, and/or point mutations. A genomic sequence can also comprise one of a number of different alleles.

Compositions disclosed herein comprise one or more ZFPs comprising engineered zinc finger binding domains, polynucleotides encoding these polypeptides, and combinations of ZFPs and ZFP-encoding polynucleotides. A zinc finger binding domain can comprise one or more zinc fingers (e.g., 2, 3, 4, 5, 6, 7, 8, 9 or more zinc fingers), and can be engineered to bind to any EPSPS genomic sequence.

ZFPs as described herein can be used to regulate EPSPS gene expression, either through activation or repression of gene transcription. ZFPs comprising fusions of zinc finger domains linked to regulatory domains can be constructed to create chimeric transcription factors that activate or repress transcription. ZFPs can also be used for targeted cleavage of an EPSPS genomic region of interest by linking zinc finger domains with nuclease cleavage domains (or cleavage half-domains) to produce zinc finger nucleases. Thus, by identifying a target EPSPS genomic region of interest at which gene regulation, cleavage, or recombination is desired, one can, according to the methods disclosed herein, construct a zinc finger protein comprising one or more fusion proteins comprising one or more regulatory domains and/or cleavage domains (or cleavage half-domains) linked to a zinc finger domain engineered to recognize an EPSPS gene sequence in that genomic region. The presence of such a ZFP comprising a fusion protein (or proteins) in a cell will result in binding of the fusion protein(s) to its (their) binding site(s) and altered regulation or cleavage within or near the genomic region. Additionally, if an EPSPS genomic region is cleaved and an exogenous polynucleotide homologous to that EPSPS genomic region is also present in the cell, homologous recombination occurs at a high rate between the EPSPS genomic region and the exogenous polynucleotide.

Plant cells can contain one or more homologous or paralogous EPSPS gene sequences, any number of which or all of which can be targeted for modification by the methods disclosed herein. Thus, compositions described herein may target one or more EPSPS genes in a plant cell, for example, 1, 2, 3, 4, 5, or up to any number of EPSPS paralogs or all EPSPS paralogs present in a plant cell. Some ZFPs may specifically bind to one particular EPSPS paralogous gene in a plant cell. Other ZFPs may bind to multiple EPSPS paralogous genes in a plant cell. Therefore, one or more ZFPs or expression vectors encoding ZFPs of different specificities may be combined to target the desired EPSPS genes of interest in a plant.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence (e.g., an EPSPS gene sequence). Non-limiting examples of methods for engineering zinc finger proteins are design and selection. A designed zinc finger protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; 6,534,261; and 6,785,613; see, also WO 98/53058; WO 98/53059; WO 98/53060; WO 02/016536 and WO 03/016496; and U.S. Pat. Nos. 6,746,838; 6,866,997; and 7,030,215. Thus, an "engineered" zinc finger protein or "non-naturally occurring" zinc finger protein is one in which one or more of the component zinc finger DNA binding domains (recognition helices) are not naturally occurring and have been engineered to bind to a pre-selected target site.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; 6,733,970; U.S. RE39,229; and WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 25,000 nucleotides in length (or any integer value therebetween or thereabove), preferably between about 100 and 5,000 nucleotides in length (or any integer therebetween), more preferably between about 200 and 2,500 nucleotides in length.

A "homologous sequence" refers to a first sequence which shares a degree of sequence identity with a second sequence, and whose sequence may be identical to that of the second sequence. A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+EMBL+DDBJ+ PDB+GenBank CDS translations+Swiss protein+Spupdate+ PIR. Details of these programs can be found on the internet. With respect to sequences described herein, the range of desired degrees of sequence identity is approximately 35% to 100% and any integer value therebetween. Typically the percent identities between sequences are at least 35%-40%; 40%-45%; 45%-50%; 50%-60%; 60%-70%; 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under, for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule for template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

A "cleavage domain" comprises one or more polypeptide sequences which possesses catalytic activity for DNA cleavage. A cleavage domain can be contained in a single polypeptide chain or cleavage activity can result from the association of two (or more) polypeptides.

A "cleavage half-domain" is a polypeptide sequence, which in conjunction with a second polypeptide (either identical or different) forms a complex having cleavage activity (preferably double-strand cleavage activity).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, an *Agrogacterium tumefacians* T-strand, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposomes, including neutral and cationic lipids), electroporation, direct injection, cell fusion, particle bombardment, calcium phosphate co-precipitation, DEAE-dextran-mediated transfer and viral vector-mediated transfer. The exogenous molecule non-plant molecule, for example, a mammalian (e.g., human or humanized) antibody.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a ZFN comprising a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, shRNA, micro RNA, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Plant" cells include, but are not limited to, cells of monocotyledonous (monocots) or dicotyledonous (dicots) plants. Non-limiting examples of monocots include cereal plants such as maize, rice, barley, oats, wheat, sorghum, rye, sugarcane, pineapple, onion, banana, and coconut. Non-limiting examples of dicots include tobacco, tomato, sunflower, cotton, sugarbeet, potato, lettuce, melon, soybean, canola (rapeseed), and alfalfa. Plant cells may be from any part of the plant and/or from any stage of plant development.

A "region of interest" is any region of cellular chromatin, such as, for example, a gene or a non-coding sequence within or adjacent to a gene, in which it is desirable to bind an exogenous molecule (e.g., an EPSPS genomic region of interest includes a region within or adjacent to an EPSPS gene). Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 25,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Target Sites

The disclosed methods and compositions include ZFPs comprising fusion proteins comprising a regulatory domain or cleavage domain (or a cleavage half-domain) and a zinc finger domain, in which the zinc finger domain, by binding to a sequence in cellular chromatin (e.g., an EPSPS gene target site or binding site), directs the activity of the regulatory domain or cleavage domain (or cleavage half-domain) to the vicinity of the sequence and, hence, modulates transcription or induces cleavage in the vicinity of the target sequence. As set forth elsewhere in this disclosure, a zinc finger domain can be engineered to bind to virtually any desired sequence. Accordingly, after identifying a region of interest containing a sequence at which gene regulation, cleavage, or recombination is desired, one or more zinc finger binding domains can be engineered to bind to one or more sequences in the region of interest.

Selection of an EPSPS genomic region of interest in cellular chromatin for binding by a zinc finger domain (e.g., a target site) can be accomplished, for example, according to the methods disclosed in co-owned U.S. Pat. No. 6,453,242 (Sep. 17, 2002), which also discloses methods for designing ZFPs to bind to a selected sequence. It will be clear to those skilled in the art that simple visual inspection of a nucleotide sequence can also be used for selection of a target site. Accordingly, any means for target site selection can be used in the claimed methods.

Target sites are generally composed of a plurality of adjacent target subsites. A target subsite refers to the sequence (usually either a nucleotide triplet, or a nucleotide quadruplet that can overlap by one nucleotide with an adjacent quadruplet) bound by an individual zinc finger. See, for example, WO 02/077227. If the strand with which a zinc finger protein makes most contacts is designated the target strand "primary recognition strand," or "primary contact strand," some zinc finger proteins bind to a three base triplet in the target strand and a fourth base on the non-target strand. A target site generally has a length of at least 9 nucleotides and, accordingly, is bound by a zinc finger binding domain comprising at least three zinc fingers. However binding of, for example, a 4-finger binding domain to a 12-nucleotide target site, a 5-finger binding domain to a 15-nucleotide target site or a 6-finger binding domain to an 18-nucleotide target site, is also possible. As will be apparent, binding of larger binding domains (e.g., 7-, 8-, 9-finger and more) to longer target sites is also possible.

It is not necessary for a target site to be a multiple of three nucleotides. For example, in cases in which cross-strand interactions occur (see, e.g., U.S. Pat. No. 6,453,242 and WO 02/077227), one or more of the individual zinc fingers of a multi-finger binding domain can bind to overlapping quadruplet subsites. As a result, a three-finger protein can bind a 10-nucleotide sequence, wherein the tenth nucleotide is part of a quadruplet bound by a terminal finger, a four-finger protein can bind a 13-nucleotide sequence, wherein the thirteenth nucleotide is part of a quadruplet bound by a terminal finger, etc.

The length and nature of amino acid linker sequences between individual zinc fingers in a multi-finger binding domain also affects binding to a target sequence. For example, the presence of a so-called "non-canonical linker," "long linker" or "structured linker" between adjacent zinc fingers in a multi-finger binding domain can allow those fingers to bind subsites which are not immediately adjacent. Non-limiting examples of such linkers are described, for example, in U.S. Pat. No. 6,479,626 and WO 01/53480. Accordingly, one or more subsites, in a target site for a zinc finger binding domain, can be separated from each other by 1, 2, 3, 4, 5 or more nucleotides. To provide but one example, a four-finger binding domain can bind to a 13-nucleotide target site comprising, in sequence, two contiguous 3-nucleotide subsites, an intervening nucleotide, and two contiguous triplet subsites. See, also, U.S. Patent Publication No. 20090305419 for compositions and methods for linking artificial nucleases to bind to target sites separated by different numbers of nucleotides Distance between sequences (e.g., target sites) refers to the number of nucleotides or nucleotide pairs intervening between two sequences, as measured from the edges of the sequences nearest each other.

In certain embodiments, ZFPs with transcription factor function are designed. For transcription factor function, simple binding and sufficient proximity to the promoter are all that is generally needed. Exact positioning relative to the promoter, orientation, and within limits, distance does not matter greatly. This feature allows considerable flexibility in choosing target sites for constructing artificial transcription factors. The target site recognized by the ZFP therefore can be any suitable site in the target gene that will allow activation or repression of gene expression by a ZFP, optionally linked to a regulatory domain. Preferred target sites include regions adjacent to, downstream, or upstream of the transcription start site. In addition, target sites that are located in enhancer regions, repressor sites, RNA polymerase pause sites, and specific regulatory sites (e.g., SP-1 sites, hypoxia response elements, nuclear receptor recognition elements, p53 binding sites), sites in the cDNA encoding region or in an expressed sequence tag (EST) coding region.

In other embodiments, ZFPs with nuclease activity are designed. Expression of a ZFN comprising a fusion protein comprising a zinc finger binding domain and a cleavage domain (or of two fusion proteins, each comprising a zinc finger binding domain and a cleavage half-domain), in a cell, effects cleavage in the vicinity of the target sequence. In certain embodiments, cleavage depends on the binding of two zinc finger domain/cleavage half-domain fusion molecules to separate target sites. The two target sites can be on opposite DNA strands, or alternatively, both target sites can be on the same DNA strand.

Zinc Finger Binding Domains

A zinc finger binding domain comprises one or more zinc fingers. Miller et al. (1985) *EMBO J.* 4:1609-1614; Rhodes (1993) *Scientific American* February:56-65; U.S. Pat. No. 6,453,242. Typically, a single zinc finger domain is about 30 amino acids in length. Structural studies have demonstrated that each zinc finger domain (motif) contains two beta sheets (held in a beta turn which contains the two invariant cysteine residues) and an alpha helix (containing the two invariant histidine residues), which are held in a particular conformation through coordination of a zinc atom by the two cysteines and the two histidines.

Zinc fingers include both canonical $C_2H_2$ zinc fingers (i.e., those in which the zinc ion is coordinated by two cysteine and two histidine residues) and non-canonical zinc fingers such as, for example, $C_3H$ zinc fingers (those in which the zinc ion is coordinated by three cysteine residues and one histidine residue) and $C_4$ zinc fingers (those in which the zinc ion is coordinated by four cysteine residues). See also WO 02/057293.

Zinc finger binding domains can be engineered to bind to a sequence of choice. See, for example, Beerli et al. (2002) *Nature Biotechnol.* 20:135-141; Pabo et al. (2001) *Ann. Rev. Biochem.* 70:313-340; Isalan et al. (2001) *Nature Biotechnol.* 19:656-660; Segal et al. (2001) *Curr. Opin. Biotechnol.* 12:632-637; Choo et al. (2000) *Curr. Opin. Struct. Biol.* 10:411-416. An engineered zinc finger binding domain can have a novel binding specificity, compared to a naturally-occurring zinc finger protein. Engineering methods include, but are not limited to, rational design and various types of selection. Rational design includes, for example, using databases comprising triplet (or quadruplet) nucleotide sequences and individual zinc finger amino acid sequences, in which each triplet or quadruplet nucleotide sequence is associated with one or more amino acid sequences of zinc fingers which bind the particular triplet or quadruplet sequence. See, for example, co-owned U.S. Pat. Nos. 6,453, 242 and 6,534,261. Additional design methods are disclosed, for example, in U.S. Pat. Nos. 6,746,838; 6,785,613; 6,866,997; and 7,030,215.

Exemplary selection methods, including phage display and two-hybrid systems, are disclosed in U.S. Pat. Nos. 5,789,538; 5,925,523; 6,007,988; 6,013,453; 6,410,248; 6,140,466; 6,200,759; and 6,242,568; as well as WO 98/37186; WO 98/53057; WO 00/27878; WO 01/88197 and GB 2,338,237.

Enhancement of binding specificity for zinc finger binding domains has been described, for example, in co-owned U.S. Pat. No. 6,794,136.

Since an individual zinc finger binds to a three-nucleotide (i.e., triplet) sequence (or a four-nucleotide sequence which can overlap, by one nucleotide, with the four-nucleotide binding site of an adjacent zinc finger), the length of a sequence to which a zinc finger binding domain is engineered to bind (e.g., a target sequence) will determine the number of zinc fingers in an engineered zinc finger binding domain. For example, for ZFPs in which the finger motifs do not bind to overlapping subsites, a six-nucleotide target sequence is bound by a two-finger binding domain; a nine-nucleotide target sequence is bound by a three-finger binding domain, etc. As noted herein, binding sites for individual zinc fingers (i.e., subsites) in a target site need not be contiguous, but can be separated by one or several nucleotides, depending on the length and nature of the amino acids sequences between the zinc fingers (i.e., the inter-finger linkers) in a multi-finger binding domain.

In a multi-finger zinc finger binding domain, adjacent zinc fingers can be separated by amino acid linker sequences of approximately 5 amino acids (so-called "canonical" inter-finger linkers) or, alternatively, by one or more non-canonical linkers. See, e.g., co-owned U.S. Pat. Nos. 6,453,242 and 6,534,261. For engineered zinc finger binding domains comprising more than three fingers, insertion of longer ("non-canonical") inter-finger linkers between certain of the zinc fingers may be preferred as it may increase the affinity and/or specificity of binding by the binding domain. See, for example, U.S. Pat. No. 6,479,626 and WO 01/53480. Accordingly, multi-finger zinc finger binding domains can also be characterized with respect to the presence and location of non-canonical inter-finger linkers. For example, a six-finger zinc finger binding domain comprising three fingers (joined by two canonical inter-finger linkers), a long linker and three additional fingers (joined by two canonical inter-finger linkers) is denoted a 2×3 configuration. Similarly, a binding domain comprising two fingers (with a canonical linker therebetween), a long linker and two additional fingers (joined by a canonical linker) is denoted a 2×2 protein. A protein comprising three two-finger units (in each of which the two fingers are joined by a canonical linker), and in which each two-finger unit is joined to the adjacent two finger unit by a long linker, is referred to as a 3×2 protein.

The presence of a long or non-canonical inter-finger linker between two adjacent zinc fingers in a multi-finger binding domain often allows the two fingers to bind to subsites which are not immediately contiguous in the target sequence. Accordingly, there can be gaps of one or more nucleotides between subsites in a target site; i.e., a target site can contain one or more nucleotides that are not contacted by a zinc finger. For example, a 2×2 zinc finger binding domain can bind to two six-nucleotide sequences separated by one nucleotide, i.e., it binds to a 13-nucleotide target site. See also Moore et al. (2001a) Proc. Natl. Acad. Sci. USA 98:1432-1436; Moore et al. (2001b) Proc. Natl. Acad. Sci. USA 98:1437-1441 and WO 01/53480.

As mentioned previously, a target subsite is a three- or four-nucleotide sequence that is bound by a single zinc finger. For certain purposes, a two-finger unit is denoted a binding module. A binding module can be obtained by, for example, selecting for two adjacent fingers in the context of a multi-finger protein (generally three fingers) which bind a particular six-nucleotide target sequence. Alternatively, modules can be constructed by assembly of individual zinc fingers. See also WO 98/53057 and WO 01/53480.

A zinc finger binding domain can be designed to bind one or more homologous (e.g., orthologous or paralogous) EPSPS target genomic sequences. For example, a zinc finger binding domain may be designed to bind specifically to one unique EPSPS target sequence. Alternatively, a zinc finger binding domain can be designed to bind multiple orthologous or paralogous EPSPS genomic sequences.

In one embodiment, described herein is a zinc finger binding domain comprising an amino acid sequence as shown in Table A. In another embodiment, the disclosure provides a polynucleotide encoding a zinc finger binding domain, wherein the zinc finger binding domain comprises an amino acid sequence as shown in Table A.

Regulatory Domains

The ZFPs described herein can optionally be associated with regulatory domains for modulation of gene expression. The ZFP can be covalently or non-covalently associated with one or more regulatory domains, alternatively two or more regulatory domains, with the two or more domains being two copies of the same domain, or two different domains. The regulatory domains can be covalently linked to the ZFP, e.g., via an amino acid linker, as part of a fusion protein. The ZFPs can also be associated with a regulatory domain via a non-covalent dimerization domain, e.g., a leucine zipper, a STAT protein N terminal domain, or an FK506 binding protein (see, e.g., O'Shea, Science 254: 539 (1991), Barahmand-Pour et al, Curr. Top. Microbiol. Immunol. 211:121-128 (1996); Klemm et al., Annu Rev. Immunol. 16:569-592 (1998); Klemm et al., Annu Rev. Immunol. 16:569-592 (1998); Ho et al., Nature 382:822-826 (1996); and Pomeranz et al., Biochem. 37:965 (1998)). The regulatory domain can be associated with the ZFP at any suitable position, including the C- or N-terminus of the ZFP.

Common regulatory domains for addition to the ZFP include, e.g., effector domains from transcription factors (activators, repressors, co-activators, co-repressors), silencers, nuclear hormone receptors, oncogene transcription factors (e.g., myc, jun, fos, myb, max, mad, rel, ets, bcl, myb, mos family members etc.); DNA repair enzymes and their associated factors and modifiers; DNA rearrangement enzymes and their associated factors and modifiers; chromatin associated proteins and their modifiers (e.g., kinases, acetylases and deacetylases); and DNA modifying enzymes (e.g., methyltransferases, topoisomerases, helicases, ligases, kinases, phosphatases, polymerases, endonucleases) and their associated factors and modifiers.

Transcription factor polypeptides from which one can obtain a regulatory domain include those that are involved in regulated and basal transcription. Such polypeptides include transcription factors, their effector domains, coactivators, silencers, nuclear hormone receptors (see, e.g., Goodrich et al., Cell 84:825-30 (1996) for a review of proteins and nucleic acid elements involved in transcription; transcription factors in general are reviewed in Barnes & Adcock, Clin. Exp. Allergy 25 Suppl. 2:46-9 (1995) and Roeder, Methods Enzymol. 273:165-71 (1996)). Databases dedicated to transcription factors are known (see, e.g., Science 269:630 (1995)). Nuclear hormone receptor transcription factors are described in, for example, Rosen et al., J. Med. Chem. 38:4855-74 (1995). The C/EBP family of transcription factors are reviewed in Wedel et al., Immunobiology 193:171-85 (1995). Coactivators and co-repressors that mediate transcription regulation by nuclear hormone receptors are reviewed in, for example, Meier, Eur. J. Endocrinol. 134(2): 158-9 (1996); Kaiser et al., Trends Biochem. Sci. 21:342-5 (1996); and Utley et al., Nature 394:498-502 (1998)). GATA transcription factors, which are involved in regulation of hematopoiesis, are described in, for example, Simon, Nat. Genet. 11:9-11 (1995); Weiss et al., Exp. Hematol. 23:99-107. TATA box binding protein (TBP) and its associated TAP polypeptides (which include TAF30, TAF55, TAF80, TAF 10, TAF150, and TAF250) are described in Goodrich & Tjian, Curr. Opin. Cell Biol. 6:403-9 (1994) and Hurley, Curr. Opin. Struct. Biol. 6:69-75 (1996). The STAT family of transcription factors are reviewed in, for example, Barahmand-Pour et al., Curr. Top. Microbiol. Immunol. 211:121-8 (1996). Transcription factors involved in disease are reviewed in Aso et al., J. Clin. Invest. 97:1561-9 (1996).

In one embodiment, the KRAB repression domain from the human KOX-1 protein is used as a transcriptional repressor (Thiesen et al., New Biologist 2:363-374 (1990); Margolin et al., PNAS 91:4509-4513 (1994); Pengue et al., Nucl. Acids Res. 22:2908-2914 (1994); Witzgall et al., PNAS 91:4514-4518 (1994)). In another embodiment, KAP-1, a KRAB co-repressor, is used with KRAB (Friedman et al., Genes Dev. 10:2067-2078 (1996)). Alternatively, KAP-1 can be used alone with a ZFP. Other preferred transcription factors and transcription factor domains that act as transcriptional repressors include MAD (see, e.g., Sommer et al., J. Biol. Chem. 273:6632-6642 (1998); Gupta et al., Oncogene 16:1149-1159 (1998); Queva et al., Oncogene 16:967-977 (1998); Larsson et al., Oncogene 15:737-748 (1997); Laherty et al., Cell 89:349-356 (1997); and Cultraro et al, Mol. Cell. Biol. 17:2353-2359 (19977)); FKHR (forkhead in rhapdosarcoma gene; Ginsberg et al., Cancer Res. 15:3542-3546 (1998); Epstein et al, Mol. Cell. Biol. 18:4118-4130 (1998)); EGR-1 (early growth response gene product-1; Yan et al., PNAS 95:8298-8303 (1998); and Liu et al., Cancer Gene Ther. 5:3-28 (1998)); the ets2 repressor factor repressor domain (ERD; Sgouras et al., EMBO J. 14:4781-4793 ((19095)); and the MAD smSIN3 interaction domain (SID; Ayer et al., Mol. Cell. Biol. 16:5772-5781 (1996)).

In one embodiment, the HSV VP16 activation domain is used as a transcriptional activator (see, e.g., Hagmann et al., J. Virol. 71:5952-5962 (1997)). Other preferred transcription factors that could supply activation domains include the VP64 activation domain (Seipel et al., EMBO J. 11:4961-4968 (1996)); nuclear hormone receptors (see, e.g., Torchia et al., Curr. Opin. Cell. Biol. 10:373-383 (1998)); the p65 subunit of nuclear factor kappa B (Bitko & Barik, J. Virol. 72:5610-5618 (1998) and Doyle & Hunt, Neuroreport 8:2937-2942 (1997)); and EGR-1 (early growth response gene product-1; Yan et al., PNAS 95:8298-8303 (1998); and Liu et al., Cancer Gene Ther. 5:3-28 (1998)).

Kinases, phosphatases, and other proteins that modify polypeptides involved in gene regulation are also useful as regulatory domains for ZFPs. Such modifiers are often involved in switching on or off transcription mediated by, for example, hormones. Kinases involved in transcriptional regulation are reviewed in Davis, Mol. Reprod. Dev. 42:459-67 (1995), Jackson et al., Adv. Second Messenger Phosphoprotein Res. 28:279-86 (1993), and Boulikas, Crit. Rev. Eukaryot. Gene Expr. 5:1-77 (1995), while phosphatases are reviewed in, for example, Schonthal & Semin, Cancer Biol. 6:239-48 (1995). Nuclear tyrosine kinases are described in Wang, Trends Biochem. Sci. 19:373-6 (1994).

As described, useful domains can also be obtained from the gene products of oncogenes (e.g., myc, jun, fos, myb, max, mad, rel, ets, bcl, myb, mos family members) and their associated factors and modifiers. Oncogenes are described in, for example, Cooper, Oncogenes, 2nd ed., The Jones and Bartlett Series in Biology, Boston, Mass., Jones and Bartlett Publishers, 1995. The ets transcription factors are reviewed in Waslyk et al., Eur. J. Biochem. 211:7-18 (1993) and Crepieux et al., Crit. Rev. Oncog. 5:615-38 (1994). Myc oncogenes are reviewed in, for example, Ryan et al., Biochem. J. 314:713-21 (1996). The jun and fos transcription factors are described in, for example, The Fos and Jun Families of Transcription Factors, Angel & Herrlich, eds. (1994). The max oncogene is reviewed in Hurlin et al., Cold Spring Harb. Symp. Quant. Biol. 59:109-16. The myb gene family is reviewed in Kanei-Ishii et al., Curr. Top. Microbiol. Immunol. 211:89-98 (1996). The mos family is reviewed in Yew et al., Curr. Opin. Genet. Dev. 3:19-25 (1993).

ZFPs can include regulatory domains obtained from DNA repair enzymes and their associated factors and modifiers. DNA repair systems are reviewed in, for example, Vos, Curr. Opin. Cell Biol. 4:385-95 (1992); Sancar, Ann. Rev. Genet. 29:69-105 (1995); Lehmann, Genet. Eng. 17:1-19 (1995); and Wood, Ann. Rev. Biochem. 65:135-67 (1996). DNA rearrangement enzymes and their associated factors and modifiers can also be used as regulatory domains (see, e.g., Gangloff et al., Experientia 50:261-9 (1994); Sadowski, FASEB J. 7:760-7 (1993)).

Similarly, regulatory domains can be derived from DNA modifying enzymes (e.g., DNA methyltransferases, topoisomerases, helicases, ligases, kinases, phosphatases, polymerases) and their associated factors and modifiers. Helicases are reviewed in Matson et al., Bioessays, 16:13-22 (1994), and methyltransferases are described in Cheng, Curr. Opin. Struct. Biol. 5:4-10 (1995). Chromatin associated proteins and their modifiers (e.g., kinases, acetylases and deacetylases), such as histone deacetylase (Wolffe, Science 272:371-2 (1996)) are also useful as domains for addition to the ZFP of choice. In one preferred embodiment, the regulatory domain is a DNA methyl transferase that acts as a transcriptional repressor (see, e.g., Van den Wyngaert et al., FEBS Lett. 426:283-289 (1998); Flynn et al., J. Mol. Biol. 279:101-116 (1998); Okano et al., Nucleic Acids Res. 26:2536-2540 (1998); and Zardo & Caiafa, J. Biol. Chem. 273:16517-16520 (1998)). In another preferred embodiment, endonucleases such as Fok1 are used as transcriptional repressors, which act via gene cleavage (see, e.g., WO95/09233; and PCT/US94/01201).

Factors that control chromatin and DNA structure, movement and localization and their associated factors and modifiers; factors derived from microbes (e.g., prokaryotes, eukaryotes and virus) and factors that associate with or modify them can also be used to obtain chimeric proteins. In one embodiment, recombinases and integrases are used as regulatory domains. In one embodiment, histone acetyltransferase is used as a transcriptional activator (see, e.g., Jin & Scotto, Mol. Cell. Biol. 18:4377-4384 (1998); Wolffe, Science 272:371-372 (1996); Taunton et al., Science 272: 408-411 (1996); and Hassig et al., PNAS 95:3519-3524 (1998)). In another embodiment, histone deacetylase is used as a transcriptional repressor (see, e.g., Jin & Scotto, Mol. Cell. Biol. 18:4377-4384 (1998); Syntichaki & Thireos, J. Biol. Chem. 273:24414-24419 (1998); Sakaguchi et al., Genes Dev. 12:2831-2841 (1998); and Martinez et al, J. Biol. Chem. 273:23781-23785 (1998)).

Linker domains between polypeptide domains, e.g., between two ZFPs or between a ZFP and a regulatory domain, can be included. Such linkers are typically polypeptide sequences, such as poly gly sequences of between about 5 and 200 amino acids. Preferred linkers are typically flexible amino acid subsequences which are synthesized as part of a recombinant fusion protein. See, e.g., U.S. Pat. No. 6,534,261; Liu et al., Proc. Nat. Acad. Sci. USA, 95:5525-5530 (1997); Pomerantz et al., Proc. Nat. Acad. Sci. USA 92:9752-9756 (1995); Kim et al., Proc. Nat. Acad. Sci. USA 93:1156-1160 (1996); herein incorporated by reference in their entireties. Alternatively, flexible linkers can be rationally designed using computer program capable of modeling both DNA-binding sites and the peptides themselves (Desjarlais & Berg, *Proc. Nat. Acad. Sci. USA* 90:2256-2260 (1993), *Proc. Nat. Acad. Sci. USA* 91:11099-11103 (1994) or by phage display methods.

In other embodiments, a chemical linker is used to connect synthetically or recombinantly produced domain sequences. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages. In addition to covalent linkage of ZFPs to regulatory domains, non-covalent methods can be used to produce molecules with ZFPs associated with regulatory domains.

Cleavage Domains

The cleavage domain portion of the fusion proteins disclosed herein can be obtained from any endonuclease or exonuclease. Exemplary endonucleases from which a cleavage domain can be derived include, but are not limited to, restriction endonucleases and homing endonucleases. See, for example, 2002-2003 Catalogue, New England Biolabs, Beverly, Mass.; and Belfort et al. (1997) *Nucleic Acids Res.* 25:3379-3388. Additional enzymes which cleave DNA are known (e.g., S1 Nuclease; mung bean nuclease; pancreatic DNase I; micrococcal nuclease; yeast HO endonuclease; see also Linn et al. (eds.) *Nucleases*, Cold Spring Harbor Laboratory Press, 1993). One or more of these enzymes (or functional fragments thereof) can be used as a source of cleavage domains and cleavage half-domains.

Similarly, a cleavage half-domain (e.g., fusion proteins comprising a zinc finger binding domain and a cleavage half-domain) can be derived from any nuclease or portion thereof, as set forth above, that requires dimerization for cleavage activity. In general, two fusion proteins are required for cleavage if the fusion proteins comprise cleavage half-domains. Alternatively, a single protein comprising two cleavage half-domains can be used. The two cleavage half-domains can be derived from the same endonuclease (or functional fragments thereof), or each cleavage half-domain can be derived from a different endonuclease (or functional fragments thereof). In addition, the target sites for the two fusion proteins are preferably disposed, with respect to each other, such that binding of the two fusion proteins to their respective target sites places the cleavage half-domains in a spatial orientation to each other that allows the cleavage half-domains to form a functional cleavage domain, e.g., by dimerizing. Thus, in certain embodiments, the near edges of the target sites are separated by 5-8 nucleotides or by 15-18 nucleotides. However any integral number of nucleotides or nucleotide pairs can intervene between two target sites (e.g., from 2 to 50 nucleotides or more). In general, the point of cleavage lies between the target sites.

Restriction endonucleases (restriction enzymes) are present in many species and are capable of sequence-specific binding to DNA (at a recognition site), and cleaving DNA at or near the site of binding. Certain restriction enzymes (e.g., Type IIS) cleave DNA at sites removed from the recognition site and have separable binding and cleavage domains. For example, the Type IIS enzyme Fok I catalyzes double-stranded cleavage of DNA, at 9 nucleotides from its recognition site on one strand and 13 nucleotides from its recognition site on the other. See, for example, U.S. Pat. Nos. 5,356,802; 5,436,150 and 5,487,994; as well as Li et al. (1992) *Proc. Natl. Acad. Sci. USA* 89:4275-4279; Li et al. (1993) *Proc. Natl. Acad. Sci. USA* 90:2764-2768; Kim et al. (1994a) *Proc. Natl. Acad. Sci. USA* 91:883-887; Kim et al. (1994b) *J. Biol. Chem.* 269:31,978-31,982. Thus, in one embodiment, fusion proteins comprise the cleavage domain (or cleavage half-domain) from at least one Type IIS restriction enzyme and one or more zinc finger binding domains, which may or may not be engineered.

An exemplary Type IIS restriction enzyme, whose cleavage domain is separable from the binding domain, is Fok I. This particular enzyme is active as a dimer (Bitinaite et al. (1998) *Proc. Natl. Acad. Sci. USA* 95: 10,570-10,575). Accordingly, for the purposes of the present disclosure, the portion of the Fok I enzyme used in the disclosed fusion proteins is considered a cleavage half-domain. Thus, for targeted double-stranded cleavage and/or targeted replacement of cellular sequences using zinc finger-Fok I fusions, two fusion proteins, each comprising a FokI cleavage half-domain, can be used to reconstitute a catalytically active cleavage domain. Alternatively, a single polypeptide molecule containing a zinc finger binding domain and two Fok I cleavage half-domains can also be used. Parameters for targeted cleavage and targeted sequence alteration using zinc finger-Fok I fusions are provided elsewhere in this disclosure.

A cleavage domain or cleavage half-domain can be any portion of a protein that retains cleavage activity, or that retains the ability to multimerize (e.g., dimerize) to form a functional cleavage domain.

Exemplary Type IIS restriction enzymes are listed in Table 1. Additional restriction enzymes also contain separable binding and cleavage domains, and these are contemplated by the present disclosure. See, for example, Roberts et al. (2003) *Nucleic Acids Res.* 31:418-420.

TABLE 1

Some Type IIS Restriction Enzymes

| | | |
|---|---|---|
| Aar I | BsrB I | SspD5 I |
| Ace III | BsrD I | Sth132 I |
| Aci I | BstF5 I | Sts I |
| Alo I | Btr I | TspDT I |
| Bae I | Bts I | TspGW I |
| Bbr7 I | Cdi I | Tth111 II |
| Bbv I | CjeP I | UbaP I |
| Bbv II | Drd II | Bsa I |
| BbvC I | Eci I | BsmB I |
| Bcc I | Eco31 I | |
| Bce83 I | Eco57 I | |
| BceA I | Eco57M I | |
| Bcef I | Esp3 I | |
| Bcg I | Fau I | |
| BciV I | Fin I | |
| Bfi I | Fok I | |
| Bin I | Gdi II | |
| Bmg I | Gsu I | |
| Bpu10 I | Hga I | |
| BsaX I | Hin4 II | |
| Bsb I | Hph I | |
| BscA I | Ksp632 I | |
| BscG I | Mbo II | |
| BseR I | Mly I | |
| BseY I | Mme I | |
| Bsi I | Mnl I | |
| Bsm I | Pfl1108 I | |
| BsmA I | Ple I | |
| BsmF I | Ppi I | |
| Bsp24 I | Psr I | |
| BspG I | RleA I | |
| BspM I | Sap I | |
| BspNC I | SfaN I | |
| Bsr I | Sim I | |

Zinc Finger Fusion Proteins

Methods for design and construction of fusion proteins (and polynucleotides encoding same) are known to those of skill in the art. For example, methods for the design and construction of fusion proteins comprising zinc finger domains and regulatory or cleavage domains (or cleavage half-domains), and polynucleotides encoding such fusion proteins, are described in co-owned U.S. Pat. Nos. 6,453, 242 and 6,534,261 and U.S. Patent Application Publications 2007/0134796 and 2005/0064474; herein incorporated by reference in their entireties. In certain embodiments, polynucleotides encoding the fusion proteins are constructed. These polynucleotides can be inserted into a vector and the vector can be introduced into a cell (see below for additional disclosure regarding vectors and methods for introducing polynucleotides into cells).

In certain embodiments of the methods described herein, a zinc finger nuclease comprises a fusion protein comprising a zinc finger binding domain and a cleavage half-domain from the Fok I restriction enzyme, and two such fusion proteins are expressed in a cell. Expression of two fusion proteins in a cell can result from delivery of the two proteins to the cell; delivery of one protein and one nucleic acid encoding one of the proteins to the cell; delivery of two nucleic acids, each encoding one of the proteins, to the cell; or by delivery of a single nucleic acid, encoding both proteins, to the cell. In additional embodiments, a fusion protein comprises a single polypeptide chain comprising two cleavage half domains and a zinc finger binding domain. In this case, a single fusion protein is expressed in a cell and, without wishing to be bound by theory, is believed to cleave DNA as a result of formation of an intramolecular dimer of the cleavage half-domains.

In certain embodiments, the components of the fusion proteins (e.g., ZFP-Fok I fusions) are arranged such that the zinc finger domain is nearest the amino terminus of the fusion protein, and the cleavage half-domain is nearest the carboxy-terminus. This mirrors the relative orientation of the cleavage domain in naturally-occurring dimerizing cleavage domains such as those derived from the Fok I enzyme, in which the DNA-binding domain is nearest the amino terminus and the cleavage half-domain is nearest the carboxy terminus. In these embodiments, dimerization of the cleavage half-domains to form a functional nuclease is brought about by binding of the fusion proteins to sites on opposite DNA strands, with the 5' ends of the binding sites being proximal to each other.

In additional embodiments, the components of the fusion proteins (e.g., ZFP-Fok I fusions) are arranged such that the cleavage half-domain is nearest the amino terminus of the fusion protein, and the zinc finger domain is nearest the carboxy-terminus. In these embodiments, dimerization of the cleavage half-domains to form a functional nuclease is brought about by binding of the fusion proteins to sites on opposite DNA strands, with the 3' ends of the binding sites being proximal to each other.

In yet additional embodiments, a first fusion protein contains the cleavage half-domain nearest the amino terminus of the fusion protein, and the zinc finger domain nearest the carboxy-terminus, and a second fusion protein is arranged such that the zinc finger domain is nearest the amino terminus of the fusion protein, and the cleavage half-domain is nearest the carboxy-terminus. In these embodiments, both fusion proteins bind to the same DNA strand, with the binding site of the first fusion protein containing the zinc finger domain nearest the carboxy terminus located to the 5' side of the binding site of the second fusion protein containing the zinc finger domain nearest the amino terminus.

In certain embodiments, the disclosed fusion proteins the amino acid sequence between the zinc finger domain and the cleavage domain (or cleavage half-domain) is denoted the "ZC linker." The ZC linker is to be distinguished from the inter-finger linkers discussed above. See, e.g., U.S. Patent Publications 20050064474A1 and 20030232410, and International Patent Publication WO05/084190, for details on obtaining ZC linkers that optimize cleavage.

In one embodiment, the disclosure provides a ZFN comprising a zinc finger protein having the recognition helix amino acid sequences shown in Table A. In another embodiment, provided herein is an ZFP expression vector comprising a nucleotide sequence encoding a ZFP having the recognition helices shown in Table A.

Regulation of Gene Expression

A variety of assays can be used to determine whether a ZFP modulates gene expression. The activity of a particular ZFP can be assessed using a variety of in vitro and in vivo assays, by measuring, e.g., protein or mRNA levels, product levels, enzyme activity; transcriptional activation or repression of a reporter gene, using, e.g., immunoassays (e.g., ELISA and immunohistochemical assays with antibodies), hybridization assays (e.g., RNase protection, northerns, in situ hybridization, oligonucleotide array studies), colorimetric assays, amplification assays, enzyme activity assays, phenotypic assays, and the like.

ZFPs are typically first tested for activity in vitro using ELISA assays and then using kidney cells. The ZFP is often first tested using a transient expression system with a reporter gene, and then regulation of the target endogenous gene is tested in cells and in whole plants, both in vivo and ex vivo. The ZFP can be recombinantly expressed in a cell, recombinantly expressed in cells transplanted into a plant, or recombinantly expressed in a transgenic plant, as well as administered as a protein to plant or cell using delivery vehicles described below. The cells can be immobilized, be in solution, be injected into a plant, or be naturally occurring in a transgenic or non-transgenic plant.

Modulation of gene expression is tested using one of the in vitro or in vivo assays described herein. Samples or assays are treated with a ZFP and compared to control samples without the test compound, to examine the extent of modulation. For regulation of endogenous gene expression, the ZFP typically has a $K_d$ of 200 nM or less, more preferably 100 nM or less, more preferably 50 nM, most preferably 25 nM or less.

The effects of the ZFPs can be measured by examining any of the parameters described above. Any suitable gene expression, phenotypic, or physiological change can be used to assess the influence of a ZFP. When the functional consequences are determined using intact cells or plants, one can also measure a variety of effects such as plant growth, transcriptional changes to both known and uncharacterized genetic markers (e.g., northern blots or oligonucleotide array studies), changes in cell metabolism such as cell growth or pH changes, and changes in intracellular second messengers such as cGMP.

Preferred assays for ZFP regulation of endogenous gene expression can be performed in vitro. In one preferred in vitro assay format, ZFP regulation of endogenous gene expression in cultured cells is measured by examining protein production using an ELISA assay. The test sample is compared to control cells treated with an empty vector or an unrelated ZFP that is targeted to another gene.

In another embodiment, ZFP regulation of endogenous gene expression is determined in vitro by measuring the level of target gene mRNA expression. The level of gene expression is measured using amplification, e.g., using PCR, LCR, or hybridization assays, e.g., northern hybridization, RNase protection, dot blotting. RNase protection is used in one embodiment. The level of protein or mRNA is detected using directly or indirectly labeled detection agents, e.g., fluorescently or radioactively labeled nucleic acids, radioactively or enzymatically labeled antibodies, and the like, as described herein.

Alternatively, a reporter gene system can be devised using the target gene promoter operably linked to a reporter gene such as luciferase, green fluorescent protein, CAT, or β-gal. The reporter construct is typically co-transfected into a cultured cell. After treatment with the ZFP of choice, the amount of reporter gene transcription, translation, or activity is measured according to standard techniques known to those of skill in the art.

Transgenic and non-transgenic plants are also used as a preferred embodiment for examining regulation of endogenous gene expression in vivo. Transgenic plants can stably express the ZFP of choice. Alternatively, plants that transiently express the ZFP of choice, or to which the ZFP has been administered in a delivery vehicle, can be used. Regulation of endogenous gene expression is tested using any one of the assays described herein.

Methods for Targeted Cleavage

The disclosed methods and compositions can be used to cleave DNA at a region of interest in cellular chromatin (e.g., at a desired or predetermined site in a genome, for example, within or adjacent to an EPSPS gene, either mutant or wild-type). For such targeted DNA cleavage, a zinc finger binding domain is engineered to bind a target site at or near the predetermined cleavage site, and a fusion protein comprising the engineered zinc finger binding domain and a cleavage domain is expressed in a cell. Upon binding of the zinc finger portion of the fusion protein to the target site, the DNA is cleaved near the target site by the cleavage domain. The exact site of cleavage can depend on the length of the ZC linker.

Alternatively, two fusion proteins, each comprising a zinc finger binding domain and a cleavage half-domain, are expressed in a cell, and bind to target sites which are juxtaposed in such a way that a functional cleavage domain is reconstituted and DNA is cleaved in the vicinity of the target sites. In one embodiment, cleavage occurs between the target sites of the two zinc finger binding domains. One or both of the zinc finger binding domains can be engineered.

For targeted cleavage using a zinc finger binding domain-cleavage domain fusion polypeptide, the binding site can encompass the cleavage site, or the near edge of the binding site can be 1, 2, 3, 4, 5, 6, 10, 25, 50 or more nucleotides (or any integral value between 1 and 50 nucleotides) from the cleavage site. The exact location of the binding site, with respect to the cleavage site, will depend upon the particular cleavage domain, and the length of the ZC linker. For methods in which two fusion polypeptides, each comprising a zinc finger binding domain and a cleavage half-domain, are used, the binding sites generally straddle the cleavage site. Thus the near edge of the first binding site can be 1, 2, 3, 4, 5, 6, 10, 25 or more nucleotides (or any integral value between 1 and 50 nucleotides) on one side of the cleavage site, and the near edge of the second binding site can be 1, 2, 3, 4, 5, 6, 10, 25 or more nucleotides (or any integral value between 1 and 50 nucleotides) on the other side of the cleavage site. Methods for mapping cleavage sites in vitro and in vivo are known to those of skill in the art.

Thus, the methods described herein can employ an engineered zinc finger binding domain fused to a cleavage domain. In these cases, the binding domain is engineered to bind to a target sequence, at or near where cleavage is desired. The fusion protein, or a polynucleotide encoding same, is introduced into a plant cell. Once introduced into, or expressed in, the cell, the fusion protein binds to the target sequence and cleaves at or near the target sequence. The exact site of cleavage depends on the nature of the cleavage domain and/or the presence and/or nature of linker sequences between the binding and cleavage domains. In cases where two fusion proteins, each comprising a cleavage half-domain, are used, the distance between the near edges of the binding sites can be 1, 2, 3, 4, 5, 6, 7, 8, 9, 10, 25 or more nucleotides (or any integral value between 1 and 50 nucleotides). Optimal levels of cleavage can also depend on both the distance between the binding sites of the two fusion proteins (see, for example, Smith et al. (2000) *Nucleic Acids Res.* 28:3361-3369; Bibikova et al. (2001) *Mol. Cell. Biol.* 21:289-297) and the length of the ZC linker in each fusion protein. See, also, U.S. Patent Publication 20050064474A1 and International Patent Publications WO05/084190, WO05/014791 and WO03/080809.

In certain embodiments, the cleavage domain comprises two cleavage half-domains, both of which are part of a single polypeptide comprising a binding domain, a first cleavage half-domain and a second cleavage half-domain. The cleavage half-domains can have the same amino acid sequence or different amino acid sequences, so long as they function to cleave the DNA.

Cleavage half-domains may also be provided in separate molecules. For example, two fusion polypeptides may be introduced into a cell, wherein each polypeptide comprises a binding domain and a cleavage half-domain. The cleavage half-domains can have the same amino acid sequence or different amino acid sequences, so long as they function to cleave the DNA. Further, the binding domains bind to target sequences which are typically disposed in such a way that, upon binding of the fusion polypeptides, the two cleavage half-domains are presented in a spatial orientation to each other that allows reconstitution of a cleavage domain (e.g., by dimerization of the half-domains), thereby positioning the half-domains relative to each other to form a functional cleavage domain, resulting in cleavage of cellular chromatin in a region of interest. Generally, cleavage by the reconstituted cleavage domain occurs at a site located between the two target sequences. One or both of the proteins can be engineered to bind to its target site.

The two fusion proteins can bind in the region of interest in the same or opposite polarity, and their binding sites (i.e., target sites) can be separated by any number of nucleotides, e.g., from 0 to 200 nucleotides or any integral value therebetween. In certain embodiments, the binding sites for two fusion proteins, each comprising a zinc finger binding domain and a cleavage half-domain, can be located between 5 and 18 nucleotides apart, for example, 5-8 nucleotides apart, or 15-18 nucleotides apart, or 6 nucleotides apart, or 16 nucleotides apart, as measured from the edge of each binding site nearest the other binding site, and cleavage occurs between the binding sites.

The site at which the DNA is cleaved generally lies between the binding sites for the two fusion proteins. Double-strand breakage of DNA often results from two single-strand breaks, or "nicks," offset by 1, 2, 3, 4, 5, 6 or more nucleotides, (for example, cleavage of double-stranded DNA by native Fok I results from single-strand breaks offset by 4 nucleotides). Thus, cleavage does not necessarily occur at exactly opposite sites on each DNA strand. In addition, the structure of the fusion proteins and the distance between the target sites can influence whether cleavage occurs adjacent a single nucleotide pair, or whether cleavage occurs at several sites. However, for many applications, including targeted recombination and targeted mutagenesis (see infra) cleavage within a range of nucleotides is generally sufficient, and cleavage between particular base pairs is not required.

As noted above, the fusion protein(s) can be introduced as polypeptides and/or polynucleotides. For example, two polynucleotides, each comprising sequences encoding one of the aforementioned polypeptides, can be introduced into a cell, and when the polypeptides are expressed and each binds to its target sequence, cleavage occurs at or near the target sequence. Alternatively, a single polynucleotide comprising sequences encoding both fusion polypeptides is introduced into a cell. Polynucleotides can be DNA, RNA or any modified forms or analogues or DNA and/or RNA.

To enhance cleavage specificity, additional compositions may also be employed in the methods described herein. For example, single cleavage half-domains can exhibit limited double-stranded cleavage activity. In methods in which two fusion proteins, each containing a three-finger zinc finger domain and a cleavage half-domain, are introduced into the cell, either protein specifies an approximately 9-nucleotide target site. Although the aggregate target sequence of 18 nucleotides is likely to be unique in a mammalian genome, any given 9-nucleotide target site occurs, on average, approximately 23,000 times in the human genome. Thus, non-specific cleavage, due to the site-specific binding of a single half-domain, may occur. Accordingly, the methods described herein contemplate the use of a dominant-negative mutant of a cleavage half-domain such as Fok I (or a nucleic acid encoding same) that is expressed in a cell along with the two fusion proteins. The dominant-negative mutant is capable of dimerizing but is unable to cleave, and also blocks the cleavage activity of a half-domain to which it is dimerized. By providing the dominant-negative mutant in molar excess to the fusion proteins, only regions in which both fusion proteins are bound will have a high enough local concentration of functional cleavage half-domains for dimerization and cleavage to occur. At sites where only one of the two fusion proteins is bound, its cleavage half-domain forms a dimer with the dominant negative mutant half-domain, and undesirable, non-specific cleavage does not occur.

Three catalytic amino acid residues in the Fok I cleavage half-domain have been identified: Asp 450, Asp 467 and Lys 469. Bitinaite et al. (1998) *Proc. Natl. Acad. Sci. USA* 95: 10,570-10,575. Thus, one or more mutations at one of these residues can be used to generate a dominant negative mutation. Further, many of the catalytic amino acid residues of other Type IIS endonucleases are known and/or can be determined, for example, by alignment with Fok I sequences and/or by generation and testing of mutants for catalytic activity.

Dimerization Domain Mutations in the Cleavage Half-Domain

Methods for targeted cleavage which involve the use of fusions between a ZFP and a cleavage half-domain (such as, e.g., a ZFP/FokI fusion) require the use of two such fusion molecules, each generally directed to a distinct target sequence. Target sequences for the two fusion proteins can be chosen so that targeted cleavage is directed to a unique site in a genome, as discussed above. A potential source of reduced cleavage specificity could result from homodimerization of one of the two ZFP/cleavage half-domain fusions. This might occur, for example, due to the presence, in a genome, of inverted repeats of the target sequences for one of the two ZFP/cleavage half-domain fusions, located so as to allow two copies of the same fusion protein to bind with an orientation and spacing that allows formation of a functional dimer.

One approach for reducing the probability of this type of aberrant cleavage at sequences other than the intended target site involves generating variants of the cleavage half-domain that minimize or prevent homodimerization. Preferably, one or more amino acids in the region of the half-domain involved in its dimerization are altered. In the crystal structure of the FokI protein dimer, the structure of the cleavage half-domains is reported to be similar to the arrangement of the cleavage half-domains during cleavage of DNA by FokI. Wah et al. (1998) *Proc. Natl. Acad. Sci. USA* 95:10564-10569. This structure indicates that amino acid residues at positions 483 and 487 play a key role in the dimerization of the FokI cleavage half-domains. The structure also indicates that amino acid residues at positions 446, 447, 479, 483, 484, 486, 487, 490, 491, 496, 498, 499, 500, 531, 534, 537, and 538 are all close enough to the dimerization interface to influence dimerization. Accordingly, amino acid sequence alterations at one or more of the aforementioned positions will likely alter the dimerization properties of the cleavage half-domain. Such changes can be introduced, for example, by constructing a library containing (or encoding) different amino acid residues at these positions and selecting variants with the desired properties, or by rationally designing individual mutants. In addition to preventing homodimerization, it is also possible that some of these mutations may increase the cleavage efficiency above that obtained with two wild-type cleavage half-domains.

Accordingly, alteration of a FokI cleavage half-domain at any amino acid residue which affects dimerization can be used to prevent one of a pair of ZFP/FokI fusions from undergoing homodimerization which can lead to cleavage at undesired sequences. Thus, for targeted cleavage using a pair of ZFP/FokI fusions, one or both of the fusion proteins can comprise one or more amino acid alterations that inhibit self-dimerization, but allow heterodimerization of the two fusion proteins to occur such that cleavage occurs at the desired target site. In certain embodiments, alterations are present in both fusion proteins, and the alterations have additive effects; i.e., homodimerization of either fusion, leading to aberrant cleavage, is minimized or abolished, while heterodimerization of the two fusion proteins is facilitated compared to that obtained with wild-type cleavage half-domains.

Methods for Targeted Alteration of Paralogous Genomic Sequences and Targeted Recombination Also described herein are methods of replacing a genomic sequence, for example of one or more paralogous genes (e.g., an EPSPS target genomic region of interest in cellular chromatin) with a homologous non-identical sequence (i.e., targeted recombination). Previous attempts to replace particular sequences have involved contacting a cell with a polynucleotide comprising sequences bearing homology to a chromosomal region (i.e., a donor DNA), followed by selection of cells in which the donor DNA molecule had undergone homologous recombination into the genome. The success rate of these methods is low, due to poor efficiency of homologous recombination and a high frequency of non-specific insertion of the donor DNA into regions of the genome other than the target site.

The present disclosure provides methods of targeted sequence alteration characterized by a greater efficiency of targeted recombination and a lower frequency of non-specific insertion events. The methods involve making and using engineered zinc finger binding domains, which bind at or near a paralogous gene sequence (e.g., EPSPS gene sequence(s)), fused to cleavage domains (or cleavage half-domains) to make one or more targeted double-stranded breaks in cellular DNA. Because double-stranded breaks in cellular DNA stimulate cellular repair mechanisms several thousand-fold in the vicinity of the cleavage site, such targeted cleavage allows for the alteration or replacement (via homology-directed repair) of gene sequences (e.g., EPSPS) at virtually any site in the genome.

The methods described herein are applicable to any paralogous (e.g., EPSPS) gene sequence from any organism or species. In certain embodiments, the EPSPS target genomic region that is altered belongs to an EPSPS gene comprising a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

In addition to the fusion molecules described herein, targeted replacement of a selected genomic sequence also requires the introduction of the replacement (or donor) sequence. The donor sequence can be introduced into the cell prior to, concurrently with, or subsequent to, expression of the fusion protein(s). The donor polynucleotide contains sufficient homology to a genomic sequence (e.g., EPSPS) to support homologous recombination (or homology-directed repair) between it and the EPSPS genomic sequence to which it bears homology. Approximately 25, 50 100, 200, 500, 750, 1,000, 1,500, 2,000 nucleotides or more of sequence homology between a donor and a genomic sequence (or any integral value between 10 and 2,000 nucleotides, or more) will support homologous recombination therebetween. Donor sequences can range in length from 10 to 5,000 nucleotides (or any integral value of nucleotides therebetween) or longer. It will be readily apparent that the donor sequence is typically not identical to the genomic sequence that it replaces. For example, the sequence of the donor polynucleotide can contain one or more single base changes, insertions, deletions, inversions or rearrangements with respect to the genomic sequence, so long as sufficient homology with chromosomal sequences is present. Alternatively, a donor sequence can contain a non-homologous sequence flanked by two regions of homology. Additionally, donor sequences can comprise a vector molecule containing sequences that are not homologous to the region of interest in cellular chromatin. Generally, the homologous region(s) of a donor sequence will have at least 50% sequence identity to a genomic sequence with which recombination is desired. In certain embodiments, 60%, 70%, 80%, 90%, 95%, 98%, 99%, or 99.9% sequence identity is present. Any value between 1% and 100% sequence identity can be present, depending upon the length of the donor polynucleotide.

A donor molecule can contain several, discontinuous regions of homology to cellular chromatin. For example, for targeted insertion of sequences not normally present in a region of interest, said sequences can be present in a donor nucleic acid molecule and flanked by regions of homology to a gene sequence in the region of interest.

To simplify assays (e.g., hybridization, PCR, restriction enzyme digestion) for determining successful insertion of the donor sequence, certain sequence differences may be present in the donor sequence as compared to the EPSPS genomic sequence. Preferably, if located in a coding region, such nucleotide sequence differences will not change the amino acid sequence, or will make silent amino acid changes (i.e., changes which do not affect the structure or function of the protein). The donor polynucleotide can optionally contain changes in sequences corresponding to the zinc finger domain binding sites in the region of interest, to prevent cleavage of donor sequences that have been introduced into cellular chromatin by homologous recombination.

The donor polynucleotide can be DNA or RNA, single-stranded or double-stranded and can be introduced into a cell in linear or circular form. If introduced in linear form, the ends of the donor sequence can be protected (e.g., from exonucleolytic degradation) by methods known to those of skill in the art. For example, one or more dideoxynucleotide residues are added to the 3' terminus of a linear molecule and/or self-complementary oligonucleotides are ligated to one or both ends. See, for example, Chang et al. (1987) *Proc. Natl. Acad. Sci. USA* 84:4959-4963; Nehls et al. (1996) *Science* 272:886-889. Additional methods for protecting exogenous polynucleotides from degradation include, but are not limited to, addition of terminal amino group(s) and the use of modified internucleotide linkages such as, for example, phosphorothioates, phosphoramidates, and O-methyl ribose or deoxyribose residues.

A polynucleotide can be introduced into a cell as part of a vector molecule having additional sequences such as, for example, replication origins, promoters and genes encoding antibiotic resistance. Moreover, donor polynucleotides can be introduced as naked nucleic acid, as nucleic acid complexed with an agent such as a liposome or poloxamer, or can be delivered by bacteria or viruses (e.g., *Agrobacterium*, *Rhizobium* sp. NGR234, *Sinorhizoboium meliloti*, *Mesorhizobium loti*, tobacco mosaic virus, potato virus X, cauliflower mosaic virus and cassava vein mosaic virus. See, e.g., Chung et al. (2006) *Trends Plant Sci.* 11(1):1-4.

Without being bound by one theory, it appears that the presence of a double-stranded break in a cellular sequence, coupled with the presence of an exogenous DNA molecule having homology to a region adjacent to or surrounding the break, activates cellular mechanisms which repair the break by transfer of sequence information from the donor molecule into the cellular (e.g., genomic or chromosomal) sequence; i.e., by a processes of homology-directed repair, also known as "gene conversion." Applicants' methods advantageously combine the powerful targeting capabilities of engineered ZFPs with a cleavage domain (or cleavage half-domain) to specifically target paralogous genes such as EPSPS genes such that cleavage of the target sequence produces a double-stranded break in the region of the genome where insertion of exogenous sequences is desired.

For alteration of a chromosomal sequence, it is not necessary for the entire sequence of the donor to be copied into the chromosome, as long as enough of the donor sequence is copied to effect the desired sequence alteration.

The efficiency of insertion of donor sequences by homologous recombination is inversely related to the distance, in the cellular DNA, between the double-stranded break and the site at which recombination is desired. In other words, higher homologous recombination efficiencies are observed when the double-stranded break is closer to the site at which recombination is desired. In cases in which a precise site of recombination is not predetermined (e.g., the desired recombination event can occur over an interval of genomic sequence), the length and sequence of the donor nucleic acid, together with the site(s) of cleavage, are selected to obtain the desired recombination event. In cases in which the desired event is designed to change the sequence of a single nucleotide pair in a genomic sequence, cellular chromatin is cleaved within 10,000 nucleotides on either side of that nucleotide pair. In certain embodiments, cleavage occurs within 1,000, 500, 200, 100, 90, 80, 70, 60, 50, 40, 30, 20, 10, 5, or 2 nucleotides, or any integral value between 2 and 1,000 nucleotides, on either side of the nucleotide pair whose sequence is to be changed.

As detailed above, the binding sites for two fusion proteins, each comprising a zinc finger binding domain and a cleavage half-domain, can be located 5-8 or 15-18 nucleotides apart, as measured from the edge of each binding site nearest the other binding site, and cleavage occurs between the binding sites. Whether cleavage occurs at a single site or at multiple sites between the binding sites is immaterial, since the cleaved genomic sequences are replaced by the donor sequences. Thus, for efficient alteration of the sequence of a single nucleotide pair by targeted recombination, the midpoint of the region between the binding sites is within 10,000 nucleotides of that nucleotide pair, preferably within 1,000 nucleotides, or 500 nucleotides, or 200 nucleotides, or 100 nucleotides, or 50 nucleotides, or 20 nucleotides, or 10 nucleotides, or 5 nucleotide, or 2 nucleotides, or one nucleotide, or at the nucleotide pair of interest.

In certain embodiments, a homologous chromosome can serve as the donor polynucleotide. Thus, for example, correction of a mutation in a heterozygote can be achieved by engineering fusion proteins which bind to and cleave the mutant sequence on one chromosome, but do not cleave the wild-type sequence on the homologous chromosome. The double-stranded break on the mutation-bearing chromosome stimulates a homology-based "gene conversion" process in which the wild-type sequence from the homologous chromosome is copied into the cleaved chromosome, thus restoring two copies of the wild-type sequence.

Methods and compositions are also provided that may enhance levels of targeted recombination including, but not limited to, the use of additional ZFP-functional domain fusions to activate expression of genes involved in homologous recombination, such as, for example, members of the RAD52 epistasis group (e.g., Rad50, Rad51, Rad51B, Rad51C, Rad51D, Rad52, Rad54, Rad54B, Mre11, XRCC2, XRCC3), genes whose products interact with the aforementioned gene products (e.g., BRCA1, BRCA2) and/or genes in the NBS1 complex. See, e.g., Boyko et al. (2006) *Plant Physiology* 141:488-497 and LaFarge et al. (2003) *Nucleic Acids Res* 31(4): 1148-1155. Similarly ZFP-functional domain fusions can be used, in combination with the methods and compositions disclosed herein, to repress expression of genes involved in non-homologous end joining (e.g., Ku70/80, XRCC4, poly(ADP ribose) polymerase, DNA ligase 4). See, for example, Riha et al. (2002) *EMBO* 21:2819-2826; Freisner et al. (2003) *Plant J.* 34:427-440; Chen et al. (1994) *European Journal of Biochemistry* 224: 135-142. Methods for activation and repression of gene expression using fusions between a zinc finger binding domain and a functional domain are disclosed, for example, in co-owned U.S. Pat. Nos. 6,534,261; 6,824,978 and 6,933, 113. Additional repression methods include the use of antisense oligonucleotides and/or small interfering RNA (siRNA or RNAi) or shRNAs targeted to the sequence of the gene to be repressed.

As an alternative to or, in addition to, activating expression of gene products involved in homologous recombination, fusions of these protein (or functional fragments thereof) with a zinc finger binding domain targeted to the genomic region of interest (e.g., EPSPS), can be used to recruit these proteins (recombination proteins) to the region of interest, thereby increasing their local concentration and further stimulating homologous recombination processes. Alternatively, a polypeptide involved in homologous recombination as described above (or a functional fragment thereof) can be part of a triple fusion protein comprising a zinc finger binding domain, a cleavage domain (or cleavage half-domain) and the recombination protein (or functional fragment thereof). Additional proteins involved in gene conversion and recombination-related chromatin remodeling, which can be used in the aforementioned methods and compositions, include histone acetyltransferases (e.g., Esa1p, Tip60), histone methyltransferases (e.g., Dot1p), histone kinases and histone phosphatases. See, also, Bhat et al. (1999) *Plant J.* 33:455-469

Further increases in efficiency of targeted recombination, in cells comprising a zinc finger/nuclease fusion molecule and a donor DNA molecule, are achieved by blocking the cells in the $G_2$ phase of the cell cycle, when homology-driven repair processes are maximally active. Such arrest can be achieved in a number of ways. For example, cells can be treated with e.g., drugs, compounds and/or small molecules which influence cell-cycle progression so as to arrest cells in $G_2$ phase. Exemplary molecules of this type include, but are not limited to, compounds which affect microtubule polymerization (e.g., vinblastine, nocodazole, Taxol), compounds that interact with DNA (e.g., cis-platinum(II) diamine dichloride, Cisplatin, doxorubicin) and/or compounds that affect DNA synthesis (e.g., thymidine, hydroxyurea, L-mimosine, etoposide, 5-fluorouracil). Additional increases in recombination efficiency are achieved by the use of histone deacetylase (HDAC) inhibitors (e.g., sodium butyrate, trichostatin A) which alter chromatin structure to make genomic DNA more accessible to the cellular recombination machinery.

Additional methods for cell-cycle arrest include overexpression of proteins which inhibit the activity of the CDK cell-cycle kinases, for example, by introducing a cDNA encoding the protein into the cell or by introducing into the cell an engineered ZFP which activates expression of the gene encoding the protein. Cell-cycle arrest is also achieved by inhibiting the activity of cyclins and CDKs, for example, using RNAi methods (e.g., U.S. Pat. No. 6,506,559) or by introducing into the cell an engineered ZFP which represses expression of one or more genes involved in cell-cycle progression such as, for example, cyclin and/or CDK genes. See, e.g., co-owned U.S. Pat. No. 6,534,261 for methods for the synthesis of engineered zinc finger proteins for regulation of gene expression.

Alternatively, in certain cases, targeted cleavage is conducted in the absence of a donor polynucleotide (preferably in S or $G_2$ phase), and recombination occurs between homologous chromosomes.

Expression Vectors

A nucleic acid encoding one or more ZFPs can be cloned into a vector for transformation into prokaryotic or eukaryotic cells for replication and/or expression. Vectors can be prokaryotic vectors, e.g., plasmids, or shuttle vectors, insect vectors, or eukaryotic vectors. A nucleic acid encoding a ZFP can also be cloned into an expression vector, for administration to a plant cell.

To express the ZFPs, sequences encoding the ZFPs are typically subcloned into an expression vector that contains a promoter to direct transcription. Suitable bacterial and eukaryotic promoters are well known in the art and described, e.g., in Sambrook et al., *Molecular Cloning, A Laboratory Manual* (2nd ed. 1989; $3^{rd}$ ed., 2001); Kriegler,

*Gene Transfer and Expression: A Laboratory Manual* (1990); and *Current Protocols in Molecular Biology* (Ausubel et al., supra. Bacterial expression systems for expressing the ZFP are available in, e.g., *E. coli, Bacillus* sp., and *Salmonella* (Palva et al., *Gene* 22:229-235 (1983)). Kits for such expression systems are commercially available. Eukaryotic expression systems for mammalian cells, yeast, and insect cells are well known by those of skill in the art and are also commercially available.

The promoter used to direct expression of a ZFP-encoding nucleic acid depends on the particular application. For example, a strong constitutive promoter suited to the host cell is typically used for expression and purification of ZFPs.

In contrast, when a ZFP is administered in vivo for regulation of a plant gene (see, "Nucleic Acid Delivery to Plant Cells" section below), either a constitutive or an inducible promoter is used, depending on the particular use of the ZFP. Non-limiting examples of plant promoters include promoter sequences derived from *A. thaliana* ubiquitin-3 (ubi-3) (Callis, et al., 1990, J. Biol. Chem. 265-12486-12493); *A. tumifaciens* mannopine synthase (Δmas) (Petolino et al., U.S. Pat. No. 6,730,824); and/or Cassava Vein Mosaic Virus (CsVMV) (Verdaguer et al., 1996, Plant Molecular Biology 31:1129-1139). See, also, Examples.

In addition to the promoter, the expression vector typically contains a transcription unit or expression cassette that contains all the additional elements required for the expression of the nucleic acid in host cells, either prokaryotic or eukaryotic. A typical expression cassette thus contains a promoter operably linked, e.g., to a nucleic acid sequence encoding the ZFP, and signals required, e.g., for efficient polyadenylation of the transcript, transcriptional termination, ribosome binding sites, or translation termination. Additional elements of the cassette may include, e.g., enhancers, and heterologous splicing signals.

The particular expression vector used to transport the genetic information into the cell is selected with regard to the intended use of the ZFP, e.g., expression in plants, animals, bacteria, fungus, protozoa, etc. (see expression vectors described below). Standard bacterial and animal expression vectors are known in the art and are described in detail, for example, U.S. Patent Publication 20050064474A1 and International Patent Publications WO05/084190, WO05/014759 and WO03/080809.

Standard transfection methods can be used to produce bacterial, mammalian, yeast or insect cell lines that express large quantities of protein, which can then be purified using standard techniques (see, e.g., Colley et al., *J. Biol. Chem.* 264:17619-17622 (1989); *Guide to Protein Purification, in Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds., 1983).

Any of the well known procedures for introducing foreign nucleotide sequences into such host cells may be used. These include the use of calcium phosphate transfection, polybrene, protoplast fusion, electroporation, ultrasonic methods (e.g., sonoporation), liposomes, microinjection, naked DNA, plasmid vectors, viral vectors, both episomal and integrative, and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing the protein of choice.

Nucleic Acid Delivery to Plant Cells

As noted above, DNA constructs may be introduced into (e.g., into the genome of) a desired plant host by a variety of conventional techniques. For reviews of such techniques see, for example, Weissbach & Weissbach *Methods for Plant Molecular Biology* (1988, Academic Press, N.Y.) Section VIII, pp. 421-463; and Grierson & Corey, *Plant Molecular Biology* (1988, 2d Ed.), Blackie, London, Ch. 7-9.

For example, the DNA construct may be introduced directly into the genomic DNA of the plant cell using techniques such as electroporation and microinjection of plant cell protoplasts, or the DNA constructs can be introduced directly to plant tissue using biolistic methods, such as DNA particle bombardment (see, e.g., Klein et al (1987) *Nature* 327:70-73). Alternatively, the DNA constructs may be combined with suitable T-DNA flanking regions and introduced into a conventional *Agrobacterium tumefaciens* host vector. *Agrobacterium tumefaciens*-mediated transformation techniques, including disarming and use of binary vectors, are well described in the scientific literature. See, for example Horsch et al (1984) *Science* 233:496-498, and Fraley et al (1983) *Proc. Nat'l. Acad. Sci. USA* 80:4803.

In addition, gene transfer may be achieved using non-*Agrobacterium* bacteria or viruses such as *Rhizobium* sp. NGR234, *Sinorhizoboium meliloti, Mesorhizobium loti*, potato virus X, cauliflower mosaic virus and cassava vein mosaic virus and/or tobacco mosaic virus, See, e.g., Chung et al. (2006) *Trends Plant Sci.* 11(1):1-4.

The virulence functions of the *Agrobacterium tumefaciens* host will direct the insertion of the construct and adjacent marker into the plant cell DNA when the cell is infected by the bacteria using binary T DNA vector (Bevan (1984) *Nuc. Acid Res.* 12:8711-8721) or the co-cultivation procedure (Horsch et al (1985) *Science* 227:1229-1231). Generally, the *Agrobacterium* transformation system is used to engineer dicotyledonous plants (Bevan et al (1982) *Ann. Rev. Genet* 16:357-384; Rogers et al (1986) *Methods Enzymol.* 118:627-641). The *Agrobacterium* transformation system may also be used to transform, as well as transfer, DNA to monocotyledonous plants and plant cells. See U.S. Pat. No. 5,591,616; Hernalsteen et al (1984) *EMBO J.* 3:3039-3041; Hooykass-Van Slogteren et al (1984) *Nature* 311:763-764; Grimsley et al (1987) *Nature* 325:1677-179; Boulton et al (1989) *Plant Mol. Biol.* 12:31-40.; and Gould et al (1991) *Plant Physiol.* 95:426-434.

Alternative gene transfer and transformation methods include, but are not limited to, protoplast transformation through calcium-, polyethylene glycol (PEG)- or electroporation-mediated uptake of naked DNA (see Paszkowski et al. (1984) *EMBO J.* 3:2717-2722, Potrykus et al. (1985) *Molec. Gen. Genet.* 199:169-177; Fromm et al. (1985) *Proc. Nat. Acad. Sci. USA* 82:5824-5828; and Shimamoto (1989) *Nature* 338:274-276) and electroporation of plant tissues (D'Halluin et al. (1992) *Plant Cell* 4:1495-1505). Additional methods for plant cell transformation include microinjection, silicon carbide mediated DNA uptake (Kaeppler et al. (1990) *Plant Cell Reporter* 9:415-418), and microprojectile bombardment (see Klein et al. (1988) *Proc. Nat. Acad. Sci. USA* 85:4305-4309; and Gordon-Kamm et al. (1990) *Plant Cell* 2:603-618).

The disclosed methods and compositions can be used to insert exogenous sequences into a predetermined location in a plant cell genome. This is useful inasmuch as expression of an introduced transgene into a plant genome depends critically on its integration site. Accordingly, genes encoding, e.g., nutrients, antibiotics or therapeutic molecules can be inserted, by targeted recombination, into regions of a plant genome favorable to their expression.

Transformed plant cells which are produced by any of the above transformation techniques can be cultured to regenerate a whole plant which possesses the transformed genotype and thus the desired phenotype. Such regeneration techniques rely on manipulation of certain phytohormones in a tissue culture growth medium, typically relying on a biocide and/or herbicide marker which has been introduced together with the desired nucleotide sequences. Plant regeneration from cultured protoplasts is described in Evans, et al., "Protoplasts Isolation and Culture" in *Handbook of Plant Cell Culture*, pp. 124-176, Macmillian Publishing Company, New York, 1983; and Binding, *Regeneration of Plants, Plant Protoplasts*, pp. 21-73, CRC Press, Boca Raton, 1985. Regeneration can also be obtained from plant callus, explants, organs, pollens, embryos or parts thereof. Such regeneration techniques are described generally in Klee et al (1987) *Ann. Rev. of Plant Phys.* 38:467-486.

Nucleic acids introduced into a plant cell can be used to confer desired traits on essentially any plant. A wide variety of plants and plant cell systems may be engineered for the desired physiological and agronomic characteristics described herein using the nucleic acid constructs of the present disclosure and the various transformation methods mentioned above. In preferred embodiments, target plants and plant cells for engineering include, but are not limited to, those monocotyledonous and dicotyledonous plants, such as crops including grain crops (e.g., wheat, maize, rice, millet, barley), fruit crops (e.g., tomato, apple, pear, strawberry, orange), forage crops (e.g., alfalfa), root vegetable crops (e.g., carrot, potato, sugar beets, yam), leafy vegetable crops (e.g., lettuce, spinach); flowering plants (e.g., petunia, rose, chrysanthemum), conifers and pine trees (e.g., pine fir, spruce); plants used in phytoremediation (e.g., heavy metal accumulating plants); oil crops (e.g., sunflower, rape seed) and plants used for experimental purposes (e.g., *Arabidopsis*). Thus, the disclosed methods and compositions have use over a broad range of plants, including, but not limited to, species from the genera *Asparagus, Avena, Brassica, Citrus, Citrullus, Capsicum, Cucurbita, Daucus, Erigeron, Glycine, Gossypium, Hordeum, Lactuca, Lolium, Lycopersicon, Malus, Manihot, Nicotiana, Orychophragmus, Oryza, Persea, Phaseolus, Pisum, Pyrus, Prunus, Raphanus, Secale, Solanum, Sorghum, Triticum, Vitis, Vigna*, and *Zea*.

One of skill in the art will recognize that after the expression cassette is stably incorporated in transgenic plants and confirmed to be operable, it can be introduced into other plants by sexual crossing. Any of a number of standard breeding techniques can be used, depending upon the species to be crossed.

A transformed plant cell, callus, tissue or plant may be identified and isolated by selecting or screening the engineered plant material for traits encoded by the marker genes present on the transforming DNA. For instance, selection may be performed by growing the engineered plant material on media containing an inhibitory amount of the antibiotic or herbicide to which the transforming gene construct confers resistance. Further, transformed plants and plant cells may also be identified by screening for the activities of any visible marker genes (e.g., the β-glucuronidase, luciferase, B or C1 genes) that may be present on the recombinant nucleic acid constructs. Such selection and screening methodologies are well known to those skilled in the art.

Physical and biochemical methods also may be used to identify plant or plant cell transformants containing inserted gene constructs. These methods include but are not limited to: 1) Southern analysis or PCR amplification for detecting and determining the structure of the recombinant DNA insert; 2) Northern blot, S1 RNase protection, primer-extension or reverse transcriptase-PCR amplification for detecting and examining RNA transcripts of the gene constructs; 3) enzymatic assays for detecting enzyme or ribozyme activity, where such gene products are encoded by the gene construct; 4) protein gel electrophoresis, Western blot techniques, immunoprecipitation, or enzyme-linked immunoassays, where the gene construct products are proteins. Additional techniques, such as in situ hybridization, enzyme staining, and immunostaining, also may be used to detect the presence or expression of the recombinant construct in specific plant organs and tissues. The methods for doing all these assays are well known to those skilled in the art.

Effects of gene manipulation using the methods disclosed herein can be observed by, for example, northern blots of the RNA (e.g., mRNA) isolated from the tissues of interest. Typically, if the amount of mRNA has increased, it can be assumed that the corresponding endogenous gene is being expressed at a greater rate than before. Other methods of measuring gene and/or CYP74B activity can be used. Different types of enzymatic assays can be used, depending on the substrate used and the method of detecting the increase or decrease of a reaction product or by-product. In addition, the levels of and/or CYP74B protein expressed can be measured immunochemically, i.e., ELISA, RIA, EIA and other antibody based assays well known to those of skill in the art, such as by electrophoretic detection assays (either with staining or western blotting). The transgene may be selectively expressed in some tissues of the plant or at some developmental stages, or the transgene may be expressed in substantially all plant tissues, substantially along its entire life cycle. However, any combinatorial expression mode is also applicable.

The present disclosure also encompasses seeds of the transgenic plants described above wherein the seed has the transgene or gene construct. The present disclosure further encompasses the progeny, clones, cell lines or cells of the transgenic plants described above wherein said progeny, clone, cell line or cell has the transgene or gene construct.

ZFPs and expression vectors encoding ZFPs can be administered directly to the plant for gene regulation, targeted cleavage, and/or recombination. In certain embodiments, the plant contains multiple paralogous target genes. It is known that plants may contain multiple paralogous genes, for example, *B. napus* has 5 paralogous EPSPS genes (SEQ ID NOS:10-14), which can be targeted by one or more ZFPs (see Examples). Thus, one or more different ZFPs or expression vectors encoding ZFPs may be administered to a plant in order to target one or more EPSPS genes in the plant. For example, 1, 2, 3, 4, 5, or up to any number of paralogs (e.g., EPSPS paralogos) or all paralogs (e.g., EPSPS paralogs) present in a plant can be targeted.

In certain embodiments, the EPSPS gene targeted comprises a nucleotide sequence selected from the group consisting of SEQ ID NOS:10-14 or a sequence having at least about 80-100% sequence identity thereto, including any percent identity within these ranges, such as 81, 82, 83, 84, 85, 86, 87, 88, 89, 90, 91, 92, 93, 94, 95, 96, 97, 98, 99% sequence identity thereto.

Administration of effective amounts is by any of the routes normally used for introducing ZFPs into ultimate contact with the plant cell to be treated. The ZFPs are administered in any suitable manner, preferably with pharmaceutically acceptable carriers. Suitable methods of administering such modulators are available and well known to those of skill in the art, and, although more than one route can be used to administer a particular composition, a particular route can often provide a more immediate and more effective reaction than another route.

Carriers may also be used and are determined in part by the particular composition being administered, as well as by the particular method used to administer the composition. Accordingly, there is a wide variety of suitable formulations of pharmaceutical compositions that are available (see, e.g., *Remington's Pharmaceutical Sciences*, 17$^{th}$ ed. 1985).

Applications

One particular area of interest in agriculture is the genetic improvement of plants to confer herbicide resistance. Many herbicides act by inhibiting a key plant enzyme or protein necessary for growth. For example, the herbicide glyphosate destroys plants by inhibiting the activity of the enzyme 5-enolpyruvyl-3-phosphoshikimate synthase (EPSPS), which synthesizes aromatic amino acids. Glyphosate tolerant plants have been produced by inserting EPSPS transgenes into plant genomes, overexpression of EPSPS, and selective mutation of EPSPS to produce glyphosate-resistant mutants (see, e.g., U.S. Pat. Nos. 5,312,910 and 6,987,213; and Papanikou et al. (2004) Planta 218(4):589-598).

For example, the disclosed methods and compositions can be used for modulating expression and for targeted alteration of EPSPS genes. In one aspect, engineered ZFPs are used to up or down-regulate expression of EPSPS in a plant. ZFPs are optionally associated with regulatory domains for modulation of gene expression, which can be covalently or non-covalently associated, and activate or repress EPSPS gene transcription. Such ZFPs can be used to increase or decrease production of the EPSPS enzyme, control biosynthesis of aromatic amino acids in plants, or increase or decrease tolerance of a plant to the herbicide glyphosate, e.g., to make crops resistant to the herbicide glyphosate, increase crop yields, or reverse resistance to glyphosate in weeds or wild plants.

Compositions comprising one or more ZFPs, or polynucleotides encoding them, can be administered to a plant cell. In one embodiment, at least two ZFPs that recognize either the same target sequence of an EPSPS gene or a different target sequence, or polynucleotides encoding such ZFPs, are administered to a cell. The first ZFP optionally is associated with the second ZFP, either covalently or non-covalently. Recognition of adjacent target sites by either associated or individual ZFPs can be used to produce cooperative binding of the ZFPs, resulting in affinities that are greater than the affinities of the ZFPs when individually bound to their respective target sites.

For repression of gene expression, typically the expression of the gene is reduced by about 20% (i.e., 80% of non-ZFP modulated expression), more preferably by about 50% (i.e., 50% of non-ZFP modulated expression), more preferably by about 75-100% (i.e., 25% to 0% of non-ZFP modulated expression). For activation of gene expression, typically expression is activated by about 1.5-fold (i.e., 150% of non-ZFP modulated expression), preferably 2-fold (i.e., 200% of non-ZFP modulated expression), more preferably 5-10 fold (i.e., 500-1000% of non-ZFP modulated expression), up to at least 100-fold or more.

The expression of engineered ZFP activators and repressors can also be controlled by small molecule regulatory systems, such as tet-regulated systems and the RU-486 system (see, e.g., Gossen & Bujard, PNAS 89:5547 (1992); Oligino et al., Gene Ther. 5:491-496 (1998); Wang et al., Gene Ther. 4:432-441 (1997); Neering et al, Blood 88:1147-1155 (1996); and Rendahl et al., Nat. Biotechnol. 16:757-761 (1998)). These regulatory systems impart small molecule control on the expression of the ZFP activators and repressors and impose a further level of control on the target gene(s) of interest (e.g., EPSPS).

In another aspect, ZFNs are used to induce mutations in an EPSPS genomic sequence, e.g., by cleaving at two sites and deleting sequences in between, by cleavage at a single site followed by non-homologous end joining, cleaving at one or two sites with insertion of an exogenous sequence between the breaks and/or by cleaving at a site so as to remove one or two or a few nucleotides. Targeted cleavage can also be used to create gene knock-outs (e.g., for functional genomics or target validation) and to facilitate targeted insertion of a sequence into a genome (i.e., gene knock-in); e.g., for purposes of cell engineering or protein overexpression. Insertion can be by means of replacements of chromosomal sequences through homologous recombination or by targeted integration, in which a new sequence (i.e., a sequence not present in the region of interest), flanked by sequences homologous to the region of interest in the chromosome, is inserted at a predetermined target site. The same methods can also be used to replace a wild-type EPSPS gene sequence with a mutant EPSPS gene sequence, or to convert one allele to a different allele. The compositions and methods described herein can also be used to generate plant lines that have inducible ZFPs and/or ZFNs stably integrated into the genome. Accordingly, the stably integrated sequences encoding the zinc finger-containing proteins can be expressed upon appropriate induction to achieve the desired effect in the plant over multiple plant generations and at any stage of plant development.

In addition, targeted cleavage of infecting or integrated plant pathogens can be used to treat pathogenic infections in a plant host, for example, by cleaving the genome of the pathogen such that it's pathogenicity is reduced or eliminated. Additionally, targeted cleavage of genes encoding receptors for plant viruses can be used to block expression of such receptors, thereby preventing viral infection and/or viral spread in the plant.

Exemplary plant pathogens include, but are not limited to, plant viruses such as Alfamoviruses, Alphacryptoviruses, Badnaviruses, Betacryptoviruses, Bigeminiviruses, Bromoviruses, Bymoviruses, Capilloviruses, Carlaviruses, Carmoviruses, Caulimoviruses, Closteroviruses, Comoviruses, Cucumoviruses, Cytorhabdoviruses, Dianthoviruses, Enamoviruses, Fabaviruses, Fijiviruses, Furoviruses, Hordeiviruses, Hybrigeminiviruses, Idaeoviruses, Ilarviruses, Ipomoviruses, Luteoviruses, Machlomoviruses, Macluraviruses, Marafiviruses, Monogeminiviruses, Nanaviruses, Necroviruses, Nepoviruses, Nucleorhabdoviruses, Oryzaviruses, Ourmiaviruses, Phytoreoviruses, Potexviruses, Potyviruses, Rymoviruses, satellite RNAs, satelliviruses, Sequiviruses, Sobemoviruses, Tenuiviruses, Tobamoviruses, Tobraviruses, Tombusviruses, Tospoviruses, Trichoviruses, Tymoviruses, Umbraviruses, Varicosaviruses and Waikaviruses; fungal pathogens such as smuts (e.g. *Ustilaginales*), rusts (*Uredinales*), ergots (*Claviceps pupurea*) and mildew; molds (*Oomycetes*) such as *Phytophthora infestans* (potato blight); bacterial pathogens such as *Erwinia* (e.g., *E. herbicola*), *Pseudomonas* (e.g., *P. aeruginosa*, *P. syringae*, *P. fluorescense* and *P. putida*), *Ralstonia* (e.g., *R. solanacearum*), *Agrobacterium* and *Xanthomonas*; roundworms (*Nematoda*); and Phytomyxea (*Polymyxa* and *Plasmodiophora*).

The disclosed methods for targeted recombination can be used to replace one or more EPSPS genomic sequences with homologous, non-identical sequences. For example, a mutant genomic sequence can be replaced by a wild-type sequence, or alternatively, a wild-type genomic sequence can be replaced by a mutant sequence, in order to, e.g., make crops resistant to the herbicide glyphosate, increase crop yields, reverse resistance to glyphosate in weeds or wild plants, etc. In like fashion, one allele of a gene can be replaced by a different allele using the methods of targeted recombination disclosed herein.

In many of these cases, an EPSPS genomic region of interest comprises a mutation, and the donor polynucleotide comprises the corresponding wild-type sequence. Similarly, a wild-type genomic sequence can be replaced by a mutant sequence, if such is desirable. For example, glyphosate resistance can be reversed or reduced in a plant by replacing a mutated or exogenous EPSPS gene with a wild-type gene, removing an exogenous EPSPS gene, mutating an EPSPS gene to lower resistance to glyphosate, or replacing the control sequences of an EPSPS gene with sequences that support a lower level of expression of EPSPS. Alternatively, a mutation can be introduced into an EPSPS gene that confers resistance to glyphosate in a plant either by mutating the EPSPS gene to produce a glyphosate tolerant EPSPS enzyme or by replacing the control sequences of the EPSPS gene with sequences that increase the level of expression of EPSPS. EPSPS gene modifications and mutant EPSPS enzymes that increase tolerance to the herbicide glyphosate are known in the art (see, e.g., U.S. Pat. Nos. 7,238,508, 7,214,535, 7,141,722, 7,045,684, 6,803,501, 6,750,377, 6,248,876, 6,225,114, 6,040,497, 5,866,775, 5,804,425, 5,776,760, 5,633,435, 5,627,061, 5,554,798, 5,463,175, 5,312,910, 5,310,667, 5,188,642, 5,145,783, 4,971,908, and 4,940,835, and WO 00/66748; herein incorporated by reference).

Targeted cleavage and targeted recombination can also be used to alter non-coding sequences (e.g., regulatory sequences such as promoters, enhancers, initiators, terminators, splice sites) to alter the levels of expression of an EPSPS gene product. Such methods can be used, for example, to increase the expression of a glyphosate tolerant EPSPS variant in a crop.

Inactivation of an EPSPS gene can be achieved, for example, by a single cleavage event, by cleavage followed by non-homologous end joining, by cleavage at two sites followed by joining so as to delete the sequence between the two cleavage sites, by targeted recombination of a missense or nonsense codon into the coding region, or by targeted recombination of an irrelevant sequence (i.e., a "stuffer" sequence) into the gene or its regulatory region, so as to disrupt the gene or regulatory region.

Targeted modification of chromatin structure, as disclosed in co-owned WO 01/83793, can be used to facilitate the binding of fusion proteins to cellular chromatin.

In additional embodiments, one or more fusions between a zinc finger binding domain and a recombinase (or functional fragment thereof) can be used, in addition to or instead of the zinc finger-cleavage domain fusions disclosed herein, to facilitate targeted recombination. See, for example, co-owned U.S. Pat. No. 6,534,261 and Akopian et al. (2003) *Proc. Natl. Acad. Sci. USA* 100:8688-8691.

In additional embodiments, the disclosed methods and compositions are used to provide fusions of ZFP binding domains with transcriptional activation or repression domains that require dimerization (either homodimerization or heterodimerization) for their activity. In these cases, a fusion polypeptide comprises a zinc finger binding domain and a functional domain monomer (e.g., a monomer from a dimeric transcriptional activation or repression domain). Binding of two such fusion polypeptides to properly situated target sites allows dimerization so as to reconstitute a functional transcription activation or repression domain.

Furthermore, as disclosed above, the methods and compositions set forth herein can be used for targeted integration of exogenous sequences into a region of interest in the genome of a cell (e.g., a regulatory or coding sequence of an EPSPS gene), for example in which cleavage enhances insertion via homology-dependent mechanisms (e.g., insertion of a donor sequence comprising an exogenous sequence together with one or more sequences that are either identical, or homologous but non-identical, with a predetermined genomic sequence (i.e., a target site)).

As noted above, in certain embodiments, targeted integration by both homology-dependent and homology-independent mechanisms involves insertion of an exogenous sequence between the ends generated by cleavage. The exogenous sequence inserted can be any length, for example, a relatively short "patch" sequence of between 1 and 50 nucleotides in length (e.g., 2, 3, 4, 5, 6, 7, 8, 9, 10, 11, 12, 13, 14, 15, 16, 17, 18, 19, 20, 21, 22, 23, 24, 25, 26, 27, 28, 29, 30, 35, 40, 45 or 50 nucleotide sequence).

In cases in which targeted integration is homology-dependent, a donor nucleic acid or donor sequence comprises an exogenous sequence together with one or more sequences that are either identical, or homologous but non-identical, with a predetermined genomic sequence (i.e., a target site). In certain embodiments two of the identical sequences or two of the homologous but non-identical sequences (or one of each) are present, flanking the exogenous sequence. An exogenous sequence (or exogenous nucleic acid or exogenous polynucleotide) is one that contains a nucleotide sequence that is not normally present in the region of interest.

Exemplary exogenous sequences include, but are not limited to, cDNAs, promoter sequences, enhancer sequences, epitope tags, marker genes, cleavage enzyme recognition sites and various types of expression constructs. Marker genes include, but are not limited to, sequences encoding proteins that mediate chemical or antibiotic resistance (e.g., ampicillin resistance, kanamycin resistance, G418 resistance, hygromycin B resistance, puromycin resistance, herbiace resistance), sequences encoding colored or fluorescent or luminescent proteins (e.g., green fluorescent protein, enhanced green fluorescent protein, red fluorescent protein, luciferase), and proteins which mediate enhanced cell growth and/or gene amplification (e.g., dihydrofolate reductase). Epitope tags include, for example, one or more copies of FLAG, His, myc, Tap, HA or any detectable amino acid sequence.

Protein expression constructs include, but are not limited to, cDNAs and transcriptional control sequences in operative linkage with cDNA sequences. Transcriptional control sequences include promoters, enhancers and insulators. Additional transcriptional and translational regulatory sequences which can be included in expression constructs include, e.g., internal ribosome entry sites, sequences encoding 2A peptides and polyadenylation signals. An exemplary protein expression construct is an antibody expression construct comprising a sequence encoding an antibody heavy chain and a sequence encoding an antibody light chain, each sequence operatively linked to a promoter (the promoters being the same or different) and either or both sequences optionally operatively linked to an enhancer (and, in the case of both coding sequences being linked to enhancers, the enhancers being the same or different).

Cleavage enzyme recognition sites include, for example, sequences recognized by restriction endonucleases, homing endonucleases and/or meganucleases. Targeted integration of a cleavage enzyme recognition site (by either homology-dependent or homology-independent mechanisms) is useful for generating cells whose genome contains only a single site that can be cleaved by a particular enzyme. Contacting such cells with an enzyme that recognizes and cleaves at the single site facilitates subsequent targeted integration of exogenous sequences (by either homology-dependent or homology-independent mechanisms) and/or targeted mutagenesis at the site that is cleaved.

Exemplary homing endonucleases include I-CeuI, PI-PspI, PI-Sce, I-SceIV, I-CsmI, I-PanI, I-SceI, I-SceII, I-PpoI, I-SceIII, I-CreI, I-TevI, I-TevII and I-TevIII. Their recognition sequences are known. See also U.S. Pat. Nos. 6,833,252, 5,420,032; Belfort et al. (1997) Nucleic Acids Res. 25:3379-3388; Dujon et al. (1989) Gene 82:115-118; Perler et al. (1994) Nucleic Acids Res. 22, 1125-1127; Jasin (1996) Trends Genet. 12:224-228; Gimble et al. (1996) J. Mol. Biol. 263:163-180; Argast et al. (1998) J. Mol. Biol. 280:345-353 and the New England Biolabs catalogue.

Although the cleavage specificity of most homing endonucleases is not absolute with respect to their recognition sites, the sites are of sufficient length that a single cleavage event per mammalian-sized genome can be obtained by expressing a homing endonuclease in a cell containing a single copy of its recognition site. It has also been reported that cleavage enzymes can be engineered to bind non-natural target sites. See, for example, Chevalier et al. (2002) Molec. Cell 10:895-905; Epinat et al. (2003) Nucleic Acids Res. 31:2952-2962; Ashworth et al. (2006) Nature 441:656-659.

Previous methods for obtaining targeted recombination and integration using homing endonucleases suffered from the problem that targeted insertion of the recognition site is extremely inefficient, requiring laborious screening to identify cells that contained the recognition site inserted at the desired location. The present methods surmount these problems by allowing highly-efficient targeted integration (either homology-dependent or homology-independent) of a recognition site for a DNA-cleaving enzyme.

In certain embodiments, targeted integration is used to insert a RNA expression construct, e.g., sequences responsible for regulated expression of micro RNA, shRNA or siRNA. Promoters, enhancers and additional transcription regulatory sequences, as described above, can also be incorporated in a RNA expression construct.

In embodiments in which targeted integration occurs by a homology-dependent mechanism, the donor sequence contains sufficient homology, in the regions flanking the exogenous sequence, to support homology-directed repair of a double-strand break in a genomic sequence, thereby inserting the exogenous sequence at the genomic target site. Therefore, the donor nucleic acid can be of any size sufficient to support integration of the exogenous sequence by homology-dependent repair mechanisms (e.g., homologous recombination). Without wishing to be bound by any particular theory, the regions of homology flanking the exogenous sequence are thought to provide the broken chromosome ends with a template for re-synthesis of the genetic information at the site of the double-stranded break.

Targeted integration of exogenous sequences, as disclosed herein, can be used to generate cells and cell lines for protein expression. See, for example, co-owned U.S. Patent Application Publication No. 2006/0063231 (the disclosure of which is hereby incorporated by reference herein, in its entirety, for all purposes). For optimal expression of one or more proteins encoded by exogenous sequences integrated into a genome, the chromosomal integration site should be compatible with high-level transcription of the integrated sequences, preferably in a wide range of cell types and developmental states. However, it has been observed that transcription of integrated sequences varies depending on the integration site due to, among other things, the chromatin structure of the genome at the integration site. Accordingly, genomic target sites that support high-level transcription of integrated sequences are desirable. In certain embodiments, it will also be desirable that integration of exogenous sequences not result in ectopic activation of one or more cellular genes (e.g., oncogenes). On the other hand, in the case of integration of promoter and/or enhancer sequences, ectopic expression may be desired.

For certain embodiments, it is desirable that an integration site is not present in an essential gene (e.g., a gene essential for cell viability), so that inactivation of said essential gene does not result from integration of the exogenous sequences. On the other hand, if the intent is to disable gene function (i.e., create a gene "knock-out") targeted integration of an exogenous sequence to disrupt an endogenous gene is an effective method. In these cases, the exogenous sequence can be any sequence capable of blocking transcription of the endogenous gene or of generating a non-functional translation product, for example a short patch of amino acid sequence, which is optionally detectable (see above). In certain embodiments, the exogenous sequences can comprise a marker gene (described above), allowing selection of cells that have undergone targeted integration.

Additional genomic target sites supporting high-level transcription of integrated sequences can be identified as regions of open chromatin or 'accessible regions" as described, for example in co-owned U.S. Patent Application Publications 2002/0064802 (May 30, 2002) and 2002/0081603 (Jun. 27, 2002).

The presence of a double-stranded break in a genomic sequence facilitates not only homology-dependent integration of exogenous sequences (i.e., homologous recombination) but also homology-independent integration of exogenous sequences into the genome at the site of the double-strand break. Accordingly, the compositions and methods disclosed herein can be used for targeted cleavage of a genomic sequence, followed by non-homology-dependent integration of an exogenous sequence at or near the targeted cleavage site. For example, a cell can be contacted with one or more ZFP-cleavage domain (or cleavage half-domain) fusion proteins engineered to cleave in a region of interest in a genome as described herein (or one or more polynucleotides encoding such fusion proteins), and a polynucleotide comprising an exogenous sequence lacking homology to the region of interest, to obtain a cell in which all or a portion of the exogenous sequence is integrated in the region of interest.

The methods of targeted integration (i.e., insertion of an exogenous sequence into a genome), both homology-dependent and -independent, disclosed herein can be used for a number of purposes. These include, but are not limited to, insertion of a gene or cDNA sequence into the genome of a cell to enable expression of the transcription and/or translation products of the gene or cDNA by the cell. For situations in which a disease or pathology can result from one of a plurality of mutations (e.g., multiple point mutations spread across the sequence of the gene), targeted integration (either homology-dependent or homology-independent) of a cDNA copy of the wild-type gene is particularly effective. For example, such a wild-type cDNA is inserted into an untranslated leader sequence or into the first exon of a gene upstream of all known mutations. In certain integrants, in which translational reading frame is preserved, the result is that the wild-type cDNA is expressed and its expression is regulated by the appropriate endogenous transcriptional regulatory sequences. In additional embodiments, such integrated cDNA sequences can include transcriptional (and/or translational) termination signals disposed downstream of the wild-type cDNA and upstream of the mutant endogenous gene. In this way, a wild-type copy of the disease-causing gene is expressed, and the mutant endogenous gene is not expressed. In other embodiments, a portion of a wild-type cDNA is inserted into the appropriate region of a gene (for example, a gene in which disease-causing mutations are clustered).

EXAMPLES

Below are examples of specific embodiments for carrying out the present disclosure. The examples are offered for illustrative purposes only, and are not intended to limit the scope of the present disclosure in any way.

Efforts have been made to ensure accuracy with respect to numbers used (e.g., amounts, temperatures, etc.), but some experimental error and deviation should, of course, be allowed for.

Example 1: Target Sequence Identification in *B. napus*

A. Sequence Identification

DNA sequences for native canola genes of known function were selected as targets for genome editing using engineered zinc-finger nucleases. The sequences of these genes, referred to as 5-enolpyruvyl shikimate-3-phosphate synthase (EPSPS) genes, were derived from *Brassica napus* L, Nex710. The enzyme EPSPS is the sixth enzyme of the shikimate pathway, which is essential for the synthesis of aromatic amino acids and many aromatic metabolites in plants (Bentley (1990) Crit. Rev. Biochem. Mol. Biol. 25:307-384). It catalyzes the transfer of the enolpyruvyl moiety of phosphoenol pyruate (PEP) to the 5-hydroxyl of shikimate 3-phosphate (S3P). Since *B. napus* is an amphidiploid species resulting from combining the chromosome sets of *B. rapa* (2n=20, AA) and *B. oleracea* (2n=18, CC) (Morinaga, 1934; U, 1935), it is expected that there would be more than one gene of EPSPS in this species.

B. DNA Isolation

*B. napus* variety Nex710 seeds were planted in the greenhouse. Samples were harvested on the 13$^{th}$ day after planting, flash frozen in liquid nitrogen, and stored at −80° C. until use.

Genomic DNA was isolated by using either cetyl-trimethylammonium bromide (CTAB) precipitation or the PLANT DNEASY extraction kit for isolation of plant DNA (Qiagen, Valencia, Calif.). For the procedure using CTAB, 1 g of leaf tissue (pools of 6 plants) was ground in liquid nitrogen. DNA was isolated as described by Permingeat et al. (Plant Mol. Biol. Reptr. (1998) 16:1-6; herein incorporated by reference), except the extraction buffer was modified. The modified extraction buffer contained 100 mM Tris-HCl (pH 8.0), 2 M NaCl, 25 mM EDTA, 2.5% CTAB (Sigma Catalog #H-5882) and 1.5% polyvinyl pyrrolidone-40 (PVP-40). Total genomic DNA was isolated with the PLANT DNEASY extraction kit (Qiagen, Valencia, Calif.) according to the manufacturer's recommendations with one modification. PVP-40 was added to the AP1 buffer (Qiagen) at a final concentration of 1%. When DNA was to be digested with restriction enzymes, it was further purified by two polyethylene glycol (PEG, MW 8,000) precipitation steps as follows. An equal volume of 1.2 M NaCl/13% PEG was added to DNA and incubated on ice for 2 hours. Samples were then spun at 5,000×g for 10 minutes, supernatant was discarded and the pellet was washed with 70% ethanol. Ethanol was completely removed by lyophilization, and the DNA pellet was resuspended in EB buffer (Qiagen).

DNA was then measured using PICOGREEN fluorescent nucleic acid stain for quantitating double-stranded DNA according to the vendor's instructions (Molecular Probes, Eugene, Oreg.) and by absorbance readings at 260 and 280 nm. DNA quality was checked by running DNA samples on a 0.8% agarose gel using Tris-acetate-EDTA (TAE) buffer (Sambrook et al. (1989) Gel electrophoresis of DNA, Molecular Cloning. Cold Spring Harbor Laboratory Press, p. 6.7).

C. EPSPS Gene Copy Number Estimation by Southern Analysis

An estimation of the EPSPS gene copy number was performed by Southern analysis prior to gene amplification, cloning, and sequencing of the *B. napus* genomic DNA. Restriction enzymes for digesting the genomic DNA were selected that cut the DNA once in the gene (Gasser and Klee (1990) Nucleic Acid Research 18:2821) and a second time in flanking genomic sequences such that a genomic DNA fragment of a unique size was created for each of the EPSPS genes on hybridization with an EPSPS gene probe. The majority of the restriction enzymes that were selected (Pvu II, Nde I, Bsr BI, Bsa I, Bcl I, Bsm I, Afl II) cut either toward the 5' end or the middle of the gene except for Bcl I, which cut at the 3' end of the gene where the probe hybridized (see below).

DNA samples (5 μg each for Nex710, 4 μg each for *B. rapa*, and 3 μg each for *B. oleracea*) were digested overnight with 30 units of each restriction enzyme, Pvu II, Nde I, Bsr BI, Bsa I, Bcl I, Bsm I, and Afl II, separately in eppendorf tubes according to the manufacturer's instructions (New England BioLabs). The digested DNA samples were then subjected to an ethanol precipitation, and the pellets were lyophilized.

Dried pellets were resuspended in 2× loading buffer, loaded on an 0.85% agarose gel, and subjected to electrophoresis in 0.4× Tris-acetate buffer at pH 8.0 (Sambrook et al. (1989) Gel electrophoresis of DNA, Molecular Cloning, Cold Spring Harbor Laboratory Press, p. 6.7). The gel was then stained with ethidium bromide and DNA bands were visualized by UV. DNA was subsequently transferred onto a GENESCREEN PLUS hybridization transfer membrane (DuPont NEN, Boston, Mass., USA) in 25 mM Na pyrophosphate buffer (Murray et al. (1992) Plant Mol. Biol. Reptr. 10:173-177). Prehybridization was carried out for a minimum of 2 hours at 65° C. in SIGMA PERFECT HYB PLUS hybridization buffer (Sigma, St. Louis, Mo.). Hybridization was carried out in the buffer overnight after adding a radioactive probe (see below). A hybridization oven (Robbins Scientific Corp, Sunnyvale, Calif., USA) was used for both the prehybridization and hybridization steps. The membrane was washed in a 20-fold dilution of the washing buffer comprising 200 mM sodium phosphate pH 7.8, 50 mM sodium pyrophosphate, 10 mM EDTA, and 2% SDS (Murray et al., supra). An initial rinse of 5 minutes was used followed by two washes of 15 minutes each. The blot was then exposed to a phosphorimaging screen at room temperature for 12 hours before scanning in a BIORAD PERSONAL FX phosphorimager (Bio-Rad, Hercules, Calif.).

The EPSPS probe for Southern blot hybridization was generated by PCR using *B. napus* var. Nex710 as the genomic DNA template. Primers were designed from the exon-8 sequence based on the published *B. napus* genomic DNA sequence (Gasser and Klee, supra.) with VECTORNTI software (Invitrogen, Carlsbad, Calif.), and custom-synthesized by MWG BIOTECH, Inc. (High Pint, N.C., USA). The sequences of the forward and reverse orientation primers were TTGGAGCTACAGTGGAAGAAGGTT (SEQ ID NO:1) and CGATTGCATCTCACTCAGTTCATTA (SEQ ID NO:2), respectively. PCR reactions contained 5 µl 10×HOT START PCR buffer (Qiagen, Valencia, Calif., USA), 2 µl 25 mM $MgCl_2$, 4 µl 10 mM nucleotide mix, 1 µl of each primer (20 µM), 1.5 units of HOT START Taq DNA polymerase (Qiagen, Valencia, Calif.), 5 µl of Nex710 template DNA, and sterile water in a total volume of 50 µl. Amplification was executed in an ICYCLER IQ real time PCR instrument (Bio-Rad, Hercules, Calif.) using the following parameters: initial denaturation for 15 minutes at 95° C. followed by 35 cycles of 30 seconds at 95° C., annealing at 55.5° C. and 52.9° C. for 30 seconds, and 30 seconds at 72° C. A PCR product of 350 base pairs was purified with a QIAQUICK nucleotide removal kit (Qiagen, Valencia, Calif.). DNA size and integrity was verified by electrophoresis on a 2.0% E-GEL agarose gel (Invitrogen, Carlsbad, Calif.). Fragment quantity was determined using the PICOGREEN DNA quantification reagent (Invitrogen, Carlsbad, Calif.). DNA probes were labeled using READY-TO-GO DNA labeling beads (-dCTP) (Amersham Biosciences, Piscataway, N.J.).

Southern blot analysis showed multiple *B. napus* EPSPS-specific bands (four or more) were present and potentially as many genes (FIG. 1). The *B. rapa* and *B. oleracea* DNA hybridized to fewer bands, and their numbers and positions did not add up in the *B. napus* patterns, indicating that sequence diversity arose in the parental and *B. napus* genomes since amphidiploidy. Minor bands could be due to cross-hybridization with other *B. napus* genes with limited sequence homology.

D. Gene Amplification and Sequence Analysis

In the present study, the *B. rapa* EPSPS cDNA sequence (GenBank Accession No. AY512663, SEQ ID NO:3) was used to query the TIGR *Brassica napus* EST database (available on the internet at tigrblast.tigr.org/tgi/) using BLAST algorithms. Two sequences, TC1307 (partial and un-annotated) and TC1308 (full-length EPSPS) were identified. The TC1307 sequence was an EPSPS gene sequence. Sequences of the AY512663 and TC 1307 were used to design multiple short oligonucleotides for use as PCR primers, including the following forward orientation oligonucleotides:

```
                                           (SEQ ID NO: 4)
5'-ATGGCGCAAGCTAGCAGAATCTGCC-3'

(SEQ ID NO: 5)
5'-ATGGCGCAAGCTAGCAGAATC-3'

(SEQ ID NO: 6)
5'-CCAGCAGCAGCGTGGAGCTTATCAGATA-3',
``` and the following reverse orientation oligonucleotides:

```
                                           (SEQ ID NO: 7)
5'-GGCCCAAAACTGATTCAACGATTGC-3'
```

```
                                           (SEQ ID NO: 8)
5'-CGTTGCCACCAGCAGCAGTA-3'

(SEQ ID NO: 9)
5'-GATGGTCCAGTCACAGTCACACTGTTCTCTGT-3'.
```

All of the oligonucleotide primers were synthesized by and purchased from Integrated DNA Technologies (IDT, Coralville, Iowa).

For PCR-based analysis, DNA amplification was carried out in a PCR reaction mixture containing 2.5 µl of 10×LA PCR bufferII ($Mg^{2+}$ plus) (Takara Bio Inc., Otsu, Shiga, Japan), 0.7 µl of 25 mM $MgCl_2$, 4 µl of 10 mM nucleotide mix, 0.5 µl of each primer (20 µM), 1.25 units of TAKARA LA Taq polymerase (Takara Bio Inc.), 1 µl of template *B. napus* variety Nex710 DNA (3-10 ng DNA), and sterile water to a 25 µl total volume. Amplification was performed either in an MJ thermocycler (Bio-Rad, Hercules, Calif.) or a GENEAMP PCR system 9700 (Applied Biosystems, Foster City, Calif.) using the following parameters: initial denaturation for 1 minute at 94° C. followed by 30 cycles of 20 seconds at 94° C., 30 seconds at 59° C., and 2 minutes at 72° C. The size and integrity of PCR products were verified by electrophoresis.

When PCR was performed with SR130 and SR131 primers (SEQ ID NOS 4 and 7, respectively), 2.6 kb-3 kb size DNA fragments were amplified. These fragments were directly cloned into the vector pCR2.1 (Invitrogen, Carlsbad, Calif.) using the TA cloning kit from Invitrogen (Carlsbad, Calif.) as per the manufacturer's recommendations. The cloned fragments were sequenced at DAS with the CEQ dye terminator cycle sequencing kit (Beckman Coulter, Fullerton, Calif.) as per the manufacturer's recommendations or sequencing services were contracted to Cogenics (formerly Lark Technologies, Inc. Houston, Tex.). Sequence analysis of multiple clones revealed 3 distinct gene fragments. These gene fragments were called EPSPS paralogs C, D and E (SEQ ID NOS:12-14).

In order to identify other variants of the genes that may exist in the *B. napus* genome, PCR was run with a temperature gradient under the same PCR conditions as described above. The amplification was performed in the ICYCLER IQ real time PCR instrument (Bio-Rad, Hercules, Calif.) using the following parameters: initial denaturation for 1 minute at 94° C. followed by 30 cycles of 20 seconds at 94° C., 30 seconds at gradient temperatures between 40° C. to 60° C., and 4 minutes at 72° C. A final extension of 30 minutes at 72° C. was carried out followed by an indefinite hold at 4° C. Under these conditions, one specific band corresponding to about 2.5 kb amplified DNA was produced at 52.5° C. The amplified DNA was cloned into the vector pCR2.1 and sequenced as described previously. Sequence analysis of multiple clones clearly indicated this PCR product represented a different gene, which was identified as EPSPS paralog B (SEQ ID NO:11).

The primers 1307F (SEQ ID NO:5) and 1307R (SEQ ID NO:8), corresponding to the fragment TC1307, were used in PCR reactions of the following composition: 5 µl of 10× Hot Start PCR buffer (Qiagen, Valencia, Calif.), 3 µl of 25 mM $MgCl_2$, 4 µl of 10 mM nucleotide mix, 1 µl of each primer (20 µM), 1.5 units of HOT START Taq DNA polymerase (Qiagen, Valencia, Calif.), 5 µl (20 ng) of Nex710 template DNA, and sterile water in a total volume of 50 µl. Amplification was executed in an ICYCLER IQ PCR instrument (Bio-Rad, Hercules, Calif.) using the following parameters: initial denaturation for 15 minutes at 95° C. followed by 35 cycles of 30 seconds at 95° C., 30 seconds at a temperature gradient of 40° C. to 60° C., and 1 minute at 72° C. A final extension of 10 minutes at 72° C. was carried out followed by an indefinite hold at 4° C. Under these conditions, a 700 bp band of amplified DNA was produced at 41.4° C. This fragment was cloned in the TOPO PCR2.1 vector and sequenced as described previously. Multiple clone alignment resulted in a 669 bp sequence, which was identified as EPSPS paralog A (SEQ ID NO:10).

Additional PCR reactions were performed with the primers 4$^{th}$_Gene_F2 (SEQ ID NO:6) and EPSP_cDNA_R9 (SEQ ID NO:9) to amplify the longer sequence of paralog A. The PCR reaction mixture was of the following composition: 10.0 µl of ACCUPRIME SUPERMIX II reagents for PCR amplification (Invitrogen, Carlsbad, Calif.), 0.5 µl of each primer (20 µM), 3 µl of Nex710 template DNA, and sterile water in a total volume of 20 µl. Amplification was executed using the following parameters: 95° C. for 3 minutes, followed by 10 cycles of 95° C. for 30 seconds, 73° C. (−0.5° C./cycle) for 30 seconds and 68° C. for 3 minutes, followed by 30 cycles of 95° C. for 30 seconds, 68° C. for 30 seconds and 68° C. for 3 minutes. This was followed by a final extension of 68° C. for 30 minutes. An amplified fragment of about 2 kb was cloned into the TOPO PCR2.1 vector and then sequenced as previously described. Alignment of multiple clones resulted in the 1571 bp sequence of paralog A.

A comparison of *B. rapa* cDNA and *B. napus* genomic DNA (SEQ ID NO: 14) showed the presence of 8 exons and 7 introns in the EPSPS gene. Based on this comparison, alignment of all 5 gene paralogs isolated from *B. napus* var. Nex710 DNA indicated that small differences, such as single nucleotide polymorphisms (SNPs), existed between the genes in the predicted coding regions, whereas the intron sequences varied significantly more at the nucleotide level.

Overall, there was 84% or more sequence homology between the 5 EPSPS paralogs (see Table 2).

TABLE 2

Sequence homology (%) between EPSPS paralogs A-E (SEQ ID NOS: 10-14)

| EPSPS paralogs | Paralog E | Paralog A | Paralog B | Paralog C |
|---|---|---|---|---|
| Paralog D | 98 | 88 | 84 | 97 |
| Paralog E |  | 88 | 84 | 95 |
| Paralog A |  |  | 92 | 87 |
| Paralog B |  |  |  | 84 |

These differences among the 5 paralogs were noted because they highlight regions of the sequences that may be discriminated by a sequence-dependent DNA binding protein such as a zinc-finger protein. It is desirable to design a zinc-finger DNA binding domain that binds to one gene sequence and not another, even if the sequence is highly similar. Nearly full-length gene sequences for four of the paralogs, B, C, D and E (SEQ ID NOS:11-14) and a partial gene sequence for the paralog A of 1575 kb (SEQ ID NO:10) were selected as targets for the design of zinc-finger nucleases, as described below.

Example 2: Design of EPSPS Zinc-Finger DNA Binding Domains

Using target sites identified from within paralogs A-E of *B. napus* EPSPS (Example 1, FIGS. 9-13), recognition helices were selected for EPSPS zinc fingers. The recognition helices for representative EPSPS zinc finger designs are shown below in Table A.

TABLE A

EPSPS Zinc finger Designs

| ZFN Name | F1 | F2 | F3 | F4 | F5 | F6 |
|---|---|---|---|---|---|---|
| 10654 EPSPS | QSGDLTR (SEQ ID NO: 91) | RSDTLST (SEQ ID NO: 92) | RNDNRIT (SEQ ID NO: 93) | QSSDLSR (SEQ ID NO: 94) | QSSDLTR (SEQ ID NO: 95) | none |
| 10658* EPSPS | DRSNLSR (SEQ ID NO: 96) | RSDALAR (SEQ ID NO: 97) | QNAHRKT (SEQ ID NO: 98) | RSDHLSE (SEQ ID NO: 99) | NSRNRKT (SEQ ID NO: 100) | none |
| 9875 EPSPS | QSSDLSR (SEQ ID NO: 94) | RSDHLSR (SEQ ID NO: 101) | QSSDLRR (SEQ ID NO: 102) | QSGNLAR (SEQ ID NO: 103) | QSGNLAR (SEQ ID NO: 103) | none |
| 10275 EPSPS | RSDVLSQ (SEQ ID NO: 104) | RNANRKK (SEQ ID NO: 105) | RSDNLST (SEQ ID NO: 106) | RNDARIT (SEQ ID NO: 107) | RSDNLST (SEQ ID NO: 106) | DNSSRIT (SEQ ID NO: 108) |
| 10740 EPSPS | RSDVLSE (SEQ ID NO: 109) | TSGHLSR (SEQ ID NO: 110) | RSDDLSK (SEQ ID NO: 111) | DSSARKK (SEQ ID NO: 112) | none | none |
| 10741 EPSPS | TSGNLTR (SEQ ID NO: 113) | TSGSLTR (SEQ ID NO: 114) | RSDHLST (SEQ ID NO: 115) | QSANRTK (SEQ ID NO: 116) | none | none |
| 10742 EPSPS | TSGNLTR (SEQ ID NO: 113) | TSGSLTR (SEQ ID NO: 114) | RSDHLSQ (SEQ ID NO: 117) | TSSNRIT (SEQ ID NO: 118) | none | none |
| 9876 EPSPS | QSSDLRR (SEQ ID NO: 102) | RSDHLSR (SEQ ID NO: 101) | QSSDLRR (SEQ ID NO: 102) | DRSALSR (SEQ ID NO: 119) | QSGNLAR (SEQ ID NO: 103) | none |

TABLE A-continued

EPSPS Zinc finger Designs

| ZFN Name | F1 | F2 | F3 | F4 | F5 | F6 |
|---|---|---|---|---|---|---|
| 9882 EPSPS | QSSDLRR (SEQ ID NO: 102) | RSDHLST (SEQ ID NO: 115) | HSDTRKK (SEQ ID NO: 120) | QSGNLAR (SEQ ID NO: 103) | QSGNLAR (SEQ ID NO: 103) | none |
| 11038 EPSPS | QSGNLAR (SEQ ID NO: 103) | TSGSLTR (SEQ ID NO: 114) | RSDHLST (SEQ ID NO: 115) | QSANRTK (SEQ ID NO: 116) | none | none |
| 11039 EPSPS | QSGNLAR (SEQ ID NO: 103) | TSGSLTR (SEQ ID NO: 114) | RSDHLSQ (SEQ ID NO: 117) | TSSNRIT (SEQ ID NO: 118) | none | none |
| 10744 EPSPS | RSDDLSE (SEQ ID NO: 121) | TNSNRKR (SEQ ID NO: 122) | RSDSLSA (SEQ ID NO: 123) | TSANLSR (SEQ ID NO: 124) | none | none |
| 10743 EPSPS | RREDLIT (SEQ ID NO: 125) | TSSNLSR (SEQ ID NO: 126) | RSDTLSE (SEQ ID NO: 127) | QNANRKT (SEQ ID NO: 128) | none | none |
| 10745 EPSPS | RSDTLSE (SEQ ID NO: 127) | TSANLSR (SEQ ID NO: 124) | RSDSLSA (SEQ ID NO: 123) | TSANLSR (SEQ ID NO: 124) | none | none |
| 9892 EPSPS | RSDNLSA (SEQ ID NO: 129) | QNRDRKN (SEQ ID NO: 130) | QSGDLTR (SEQ ID NO: 91) | RSDALAR SEQ ID NO: 97) | RSDNLRE (SEQ ID NO: 131) | none |
| 9895 EPSPS | RSAALAR (SEQ ID NO: 132) | RSDDLTR (SEQ ID NO: 133) | QSGDLTR (SEQ ID NO: 91) | RSDTLSQ (SEQ ID NO: 134) | QSGSLTR (SEQ ID NO: 135) | none |
| 9896 EPSPS | RSDALAR (SEQ ID NO: 97) | RSDDLTR (SEQ ID NO: 133) | QSGDLTR (SEQ ID NO: 91) | RSDTLSQ (SEQ ID NO: 134) | QSGSLTR (SEQ ID NO: 135) | none |
| 10657* EPSPS | DRSNLSR (SEQ ID NO: 96) | RSDALAR (SEQ ID NO: 97) | QNAHRKT (SEQ ID NO: 98) | RSDHLSE (SEQ ID NO: 99) | NSRNRKT (SEQ IN NO: 100) | none |
| 12385 EPSPS | QSGDLTR SEQ ID NO: 91) | RSDTLST (SEQ ID NO: 92) | RNDNRIT (SEQ ID NO: 93) | QSSDLSR (SEQ ID NO: 94) | LLTTLKA (SEQ ID NO: 136) | none |
| 12202* EPSPS | DRSNLSR (SEQ ID NO: 96) | RSDALAR (SEQ ID NO: 97) | QNAHRKT (SEQ ID NO: 98) | RSDHLSE (SEQ ID NO: 99) | KNFNLHQ (SEQ ID NO: 137) | none |
| 14318* EPSPS | DRSNLSR (SEQ ID NO: 96) | RSDALAR (SEQ ID NO: 97) | QNAHRKT (SEQ ID NO: 98) | RSDHLSE (SEQ ID NO: 99) | KNFNLHQ (SEQ ID NO: 137) | none |
| 14320* EPSPS | DRSNLSR (SEQ ID NO: 96) | RSDALAR (SEQ ID NO: 97) | QNAHRKT (SEQ ID NO: 98) | RSDHLSE (SEQ ID NO: 99) | KNFNLHQ (SEQ ID NO: 137) | none |
| 13969 EPSPS | DRSNLSR (SEQ ID NO: 96) | RSDALAR (SEQ ID NO: 97) | TSTGLLI (SEQ ID NO: 138) | RSDHLSE (SEQ ID NO: 99) | KNFNLHQ (SEQ ID NO: 137) | none |
| 12540 EPSPS | DRSNLSR (SEQ ID NO: 96) | RSDALAR (SEQ ID NO: 97) | VSHTRLD (SEQ ID NO: 139) | RSDHLSE (SEQ ID NO: 99) | NSRNRKT (SEQ ID NO: 100) | none |
| 12352 EPSPS | QSGDLTR (SEQ ID NO: 91) | RSDTLST (SEQ ID NO: 92) | TRYKLMS (SEQ ID NO: 140) | QSSDLSR (SEQ ID NO: 94) | QSSDLTR (SEQ ID NO: 95) | none |
| 11034 EPSPS | RSDVLSE (SEQ ID NO: 109) | TSGHLSR (SEQ ID NO: 110) | RSDDLSK (SEQ ID NO: 111) | DSSARKK (SEQ ID NO: 112) | none | none |

TABLE A-continued

EPSPS Zinc finger Designs

| ZFN Name | F1 | F2 | F3 | F4 | F5 | F6 |
|---|---|---|---|---|---|---|
| 11036 EPSPS | TSGNLTR (SEQ ID NO: 113) | TSGSLTR (SEQ ID NO: 114) | RSDHLST (SEQ ID NO: 115) | QSANRTK (SEQ ID NO: 116) | none | none |
| 11037 EPSPS | TSGNLTR (SEQ ID NO: 113) | TSGSLTR (SEQ ID NO: 114) | RSDHLSQ (SEQ ID NO: 117) | TSSNRIT (SEQ ID NO: 118) | none | none |

(*Note-the 10657 and 10658, the 12202, 14318 and 14320, the 10740 and 11034, the 10741 and 11036, and the 10742 and 11037 ZFNs differ from each other by mutations that are not located in the recognition helices).

Target sites of the zinc finger designs are shown below in Table B. ZFPs 10654 and 10658 were designed for sites in paralogs C and D; ZFPs 9875 and 10275 were designed for target sites in paralog D; and ZFPs 10740, 10741 and 10742 were designed to bind to target sites in paralogs A and B.

TABLE B

Target Sites of EPSPS Zinc Fingers

| ZFN Name | Target Site (5' to 3') |
|---|---|
| 10654 EPSPS | ttACTGCTgCAGGTGGCAac (SEQ ID NO: 141) |
| 10658 EPSPS | ggCAGCGGTGAGTGGACgc (SEQ ID NO: 142) |
| 9875 EPSPS | ttGAAGAAGCTGGGGCTta (SEQ ID NO: 143) |
| 10275 EPSPS | gcATCAAGcATGTAGTTGATGtc (SEQ ID NO: 144) |
| 10740 EPSPS | aaATCTCGGGTCTGat (SEQ ID NO: 145) |
| 10741 EPSPS | tcTAATGGGTTGAAgc (SEQ ID NO: 146) |
| 10742 EPSPS | tcTAATGGGTTGAAgc (SEQ ID NO: 146) |
| 9876 EPSPS | ttGAAGAAGCTGGGGCTta (SEQ ID NO: 143) |
| 9882 EPSPS | ttGAAGAAGCTGGGGCTta (SEQ ID NO: 143) |
| 11038 EPSPS | tcTAATGGGTTGAAgc (SEQ ID NO: 146) |
| 11039 EPSPS | tcTAATGGGTTGAAgca (SEQ ID NO: 146) |
| 10744 EPSPS | gaGATTTGGATCCGgg (SEQ ID NO: 147) |
| 10743 EPSPS | tcCAACCGGATTCTtc (SEQ ID NO: 148) |
| 10745 EPSPS | gaGATTTGGATCCGgg (SEQ ID NO: 147) |
| 9892 EPSPS | tgCAGGTGGCAaCGCAAGgat (SEQ ID NO: 149) |
| 9895 EPSPS | caGTAACGGCAGCGGTGag (SEQ ID NO: 150) |
| 9896 EPSPS | caGTAACGGCAGCGGTGag (SEQ ID NO: 150) |
| 10657 EPSPS | ggCAGCGGTGAGTGGACgc (SEQ ID NO: 142) |
| 12385 EPSPS | ttACTGCTgCAGGTGGCAac (SEQ ID NO: 141) |
| 12202 EPSPS | ggCAGCGGTGAGTGGACgc (SEQ ID NO: 142) |
| 14318 EPSPS | ggCAGCGGTGAGTGGACgc (SEQ ID NO: 142) |
| 14320 EPSPS | ggCAGCGGTGAGTGGACgc (SEQ ID NO: 142) |
| 13969 EPSPS | GCAGCGGTGAGTGGACG (SEQ ID NO: 151) |
| 12540 EPSPS | tgCAGCTGTAAGTGGACgc (SEQ ID NO: 152) |
| 12352 EPSPS | ttACTGCTgCTGGTGGCAac (SEQ ID NO: 153) |
| 11034 EPSPS | aaATCTCGGGTCTGat (SEQ ID NO: 145) |
| 11036 EPSPS | tcTAATGGGTTGAAgc (SEQ ID NO: 146) |
| 11037 EPSPS | tcTAATGGGTTGAAgc (SEQ ID NO: 146) |

The EPSPS designs were incorporated into zinc finger expression vectors encoding a protein having at least one finger with a CCHC structure. See, U.S. Patent Publication No. 20080182332. In particular, the last finger in each protein had a CCHC backbone. The zinc finger-encoding sequences were then fused to the nuclease domain of the type IIS restriction enzyme FokI (amino acids 384-579 of the sequence of Wah et al. (1998) *Proc. Natl. Acad. Sci. USA* 95:10564-10569 via a four amino acid ZC linker) to form EPSPS ZFNs. Various ZFNs were assayed for biological activity and/or toxicity as described in U.S. Patent Publication No. 20090111119.

Example 3: Functional Validation of EPSPS-Specific ZFNs in HEK293 Cells

The ability of EPSPS ZFNs as described herein to facilitate homologous recombination was tested in the GFP system described in Urnov (2005) *Nature* 435(7042):646-51 and U.S. Patent Publication No. 20050064474 (e.g., Examples 6-11). Briefly, HEK 293 reporter cells lines harboring the EPSP gene region of interest were generated as follows. The EPSP gene region of interest was amplified by PCR and subsequently cloned into pcDNA4TO– GIF. HEK 293 cells were transfected with the above plasmid and subsequently selected 48 hours post-transfection, in the presence of 400 µg/ml of Zeocin.

Pools of stable clones obtained were then tested with the ZFNs directed towards the specific region of interest of the EPSP gene in the above generated reporter cell lines as follows. Reporter cell lines were seeded at 350,000 cells/well in 12 well-plate in 1 mL of DMEM, 10% FBS media (no PSG) and transfected with 50 or 100 ng of each ZFN and 500 ng of the promoter-less GFP donor (Umov (2005) Nature) were transfected into 500,000 reporter cells, using 2 uL of Lipofectamine 2000 (Invitrogen) per sample, as per the Invitrogen Lipofectamine 2000 protocol. Transfections for each ZFN pair was done in triplicates. One day after transfection 1 mL of DMEM media was added with 1.5 uL of Vinblastine at a final concentration of 0.2 µM to 1 mM to each well and was removed 72 hours post-transfection. The cells were assayed for GFP expression 5 days post-transfection by measuring 40,000 cells per transfection on the Guava benchtop FACS analyzer. Exemplary results are shown in FIG. 9A to 9E.

Example 4: One ZFN can Cleave Two or More EPSPS Paralogs in *B. napus* Var. Nex710

In order to assess the functionality of designed zinc-finger nuclease proteins in plant cells, methods for the expression of such proteins in living plant cells were utilized. DNA encoding zinc-finger nuclease proteins can be delivered into plant cells under conditions where the DNA is not incorporated into the plant cell genome. Thus, the DNA molecule is transiently maintained in plant cells and acts as a template for gene expression. Alternatively, DNA encoding zinc-finger nuclease proteins can be delivered into plant cells under conditions that allow the DNA to be incorporated into the plant cell genome, resulting in transgenesis of the zinc-finger nuclease encoding genes such that the DNA molecule is stably maintained in the plant cells and acts as a template for gene expression. One skilled in the art may utilize either transient or transgenic expression of zinc-finger nucleases encoding DNAs in order to assess the functionality of these proteins in living plant cells.

A. Vector Design

Plasmid vectors for the expression of ZFN proteins in *B. napus* cells were constructed. In order to optimize the expression and relative stoichiometry of the 2 distinct proteins required to form a functional zinc-finger nuclease heterodimer, an expression strategy was adopted that resulted in insertion of the open reading frames of both ZFNs monomers in a single vector, driven by a single promoter. This strategy exploited the functionality of a 2A sequence (Mattion, et al. (1996) J. Virol. 70, 8124-8127) derived from the *Thesoa assigna* virus, either a SMV virus nuclear localization (NLS) signal (PKKKRKV; SEQ ID NO:15); Kalderon et al. (1984a) Nature 311: 33-38; Kalderon et al. (1984b) Cell 39: 499-509) or a maize NLS from the opaque-2 gene (op-2; Maddaloni et al. (1989) Nucleic Acids Research 17:7532; Van Eenennaam et al. (2004) Metabolic Engineering 6:101-108) and a promoter derived from the cassava vein mosaic virus promoter or CsVMV (see Table 3).

TABLE 3

Description of ZFN pairs and expression elements present in various constructs that were used for *B. napus* transformation.

| S.N. | ZFN pair | Construct Number | Construct type | Gene cassettes |
|---|---|---|---|---|
| 1 | 10654-v2/ 10657-v2 | pDAB7147 | Binary | CsVMV/ZFNpair/ AtuORF23//AtUbi10/Pat/ AtuORF1 |
| 2 | 10654-v3/ 10658-v3 | pDAB7150 | Binary | CsVMV/ZFNpair/ AtuORF23//AtUbi10/Pat/ AtuORF1 |
| 3 | 10654-v2/ 10657-v2 | pDAB7151 | Non-binary | CsVMV/ZFNpair/ AtuORF23 |
| 4 | 10654-v3/ 10658-v3 | pDAB7154 | Non-binary | CsVMV/ZFNpair/ AtuORF23 |
| 5 | 10740-v2/ 10741-v2 | pDAB7185 | Binary | RB7 MAR//CsVMV// ZFN pair//AtuORF23// Interrupted ipt (onc 4) gene Orf//4OCS delta mas 2'//PAT//AtuORFl |
| 6 | 10740-v2/ 10742-v2 | pDAB7186 | Binary | RB7 MAR//CsVMV// ZFN pair//AtuORF23// Interrupted ipt (onc 4) gene Orf//4OCS delta mas 2'//PAT//AtuORFl |

CsVMV = Cassava vein mosaic virus promoter and leader sequence of 517 bp (Verdaguer et al. (1998) Plant Mol. Biol. 37: 1055-1067);
AtuORF23 = *Agrobacterium tumefacians* ORF23 3' UTR;
AtUbi10 = *Arabidopsis thaliana* ubiquitin gene 10 promoter;
Pat = Phosphinothricin acetyl transferase gene from *Streptomyces viridochromogenes*. It is a rebuilt gene of what is reported in the U.S. Pat. No. 5,633,434);
AtuORF1 = *Agrobacterium tumefacians* ORF1 3' UTR (Genebank accession number X00493, NC_002377);
RB7 MAR = Tobacco matrix attachment region;
4OCS delta mas 2' = a modified mannopine synthase promoter which contains 4X OCS elements to enhance expression;
Interrupted ipt (onc 4) gene Orf = *Agrobacterium tumefaciens* disrupted ipt gene (genebank sequence ID ATTMRPTI was used for design).

A stepwise modular cloning scheme was devised to develop these expression vectors for any given pair of ZFN-encoding genes selected from the library archive or synthesized de novo. First, a pVAX vector (see, for example U.S. Patent Publication 2005-0267061; the disclosure of which is incorporated by reference) was modified to encompass the N-terminal expression domain as shown in FIGS. 2A-2E. Features of this modified plasmid (pVAX-N2A-NLSop2-EGFP-FokMono) (FIG. 2A) include a redesigned and synthesized segment encoding a NLS, and a redesigned and synthesized segment encoding the FokI nuclease domain utilizing the dicot codon-bias. Additionally, a single nucleotide insertion (C) downstream of the unique Xho I site created an extra Sac I site for cloning convenience.

Second, a pVAX vector (see, for example U.S. Patent Publication 2005-0267061) was also modified to encompass the C-terminal expression domain. Features of this modified plasmid (pVAX-C2A-NLSop2-EGFP-FokMono) (FIG. 2B) included a redesigned and synthesized segment encoding a NLS and a redesigned and synthesized segment encoding the FokI nuclease domain utilizing the dicot codon-bias. Additionally, the 2A sequence from *Thosea asigna* virus (EGRGSLLTCGDVEENPGP, SEQ ID NO:16) was introduced at the N-terminus of the ZFN ORF for the purpose of subsequent linking of the two protein encoding domains.

Figures 2A, 2B:
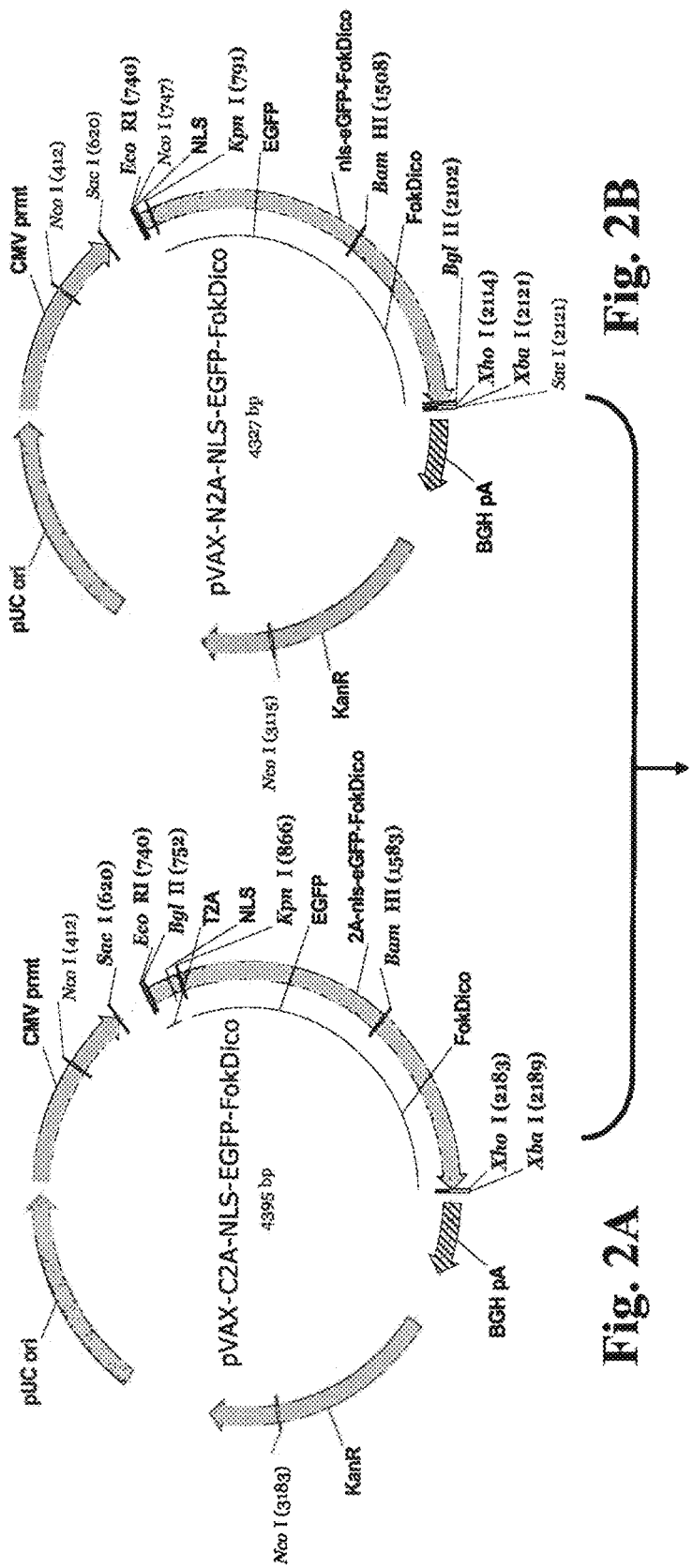
FIGS. 2A-2E show a schematic representation of the cloning strategy used to generate ZFN expression constructs. A stepwise cloning strategy was used: Individual ZFN-encoding genes were cloned into vectors and pVAX-C2A-NLSop2-EGFP-FokMono (FIG. 2A) and pVAX-N2A-NLSop2-EGFP-FokMono (FIG. 2B) to create a dual-protein cassette (FIG. 2C). This cassette was ligated into pDAB3731 to generate a final plasmid (FIG. 2D) for expression of the ZFN heterodimer. The ZFN cassette was then transferred into a binary vector with the Gateway technology to create a construct (FIG. 2E) for *Agrobacterium*-mediated *B. napus* transformation. ZFN d2=10654-CH3-v2; ZFN rb2=10657-CH3-v2.
Figure 2C:
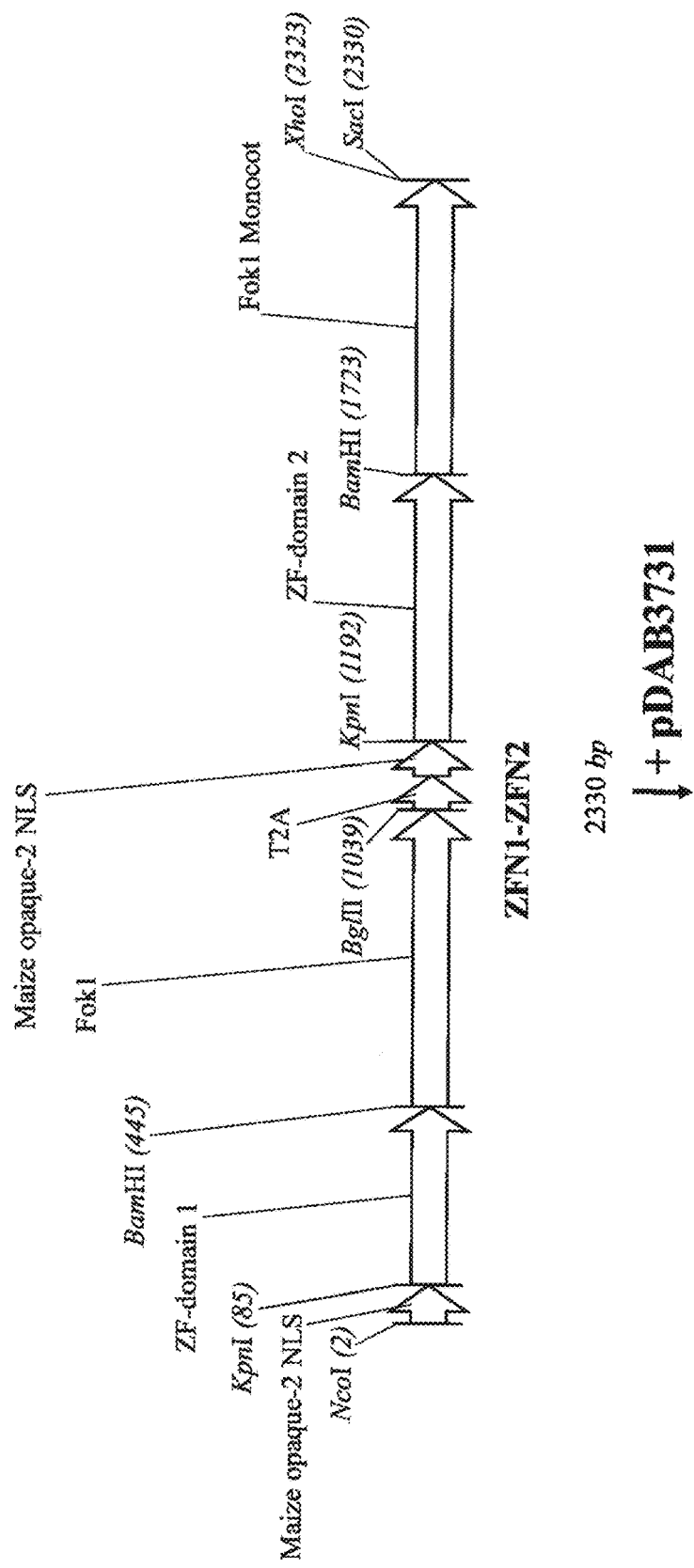
Figure 2D:
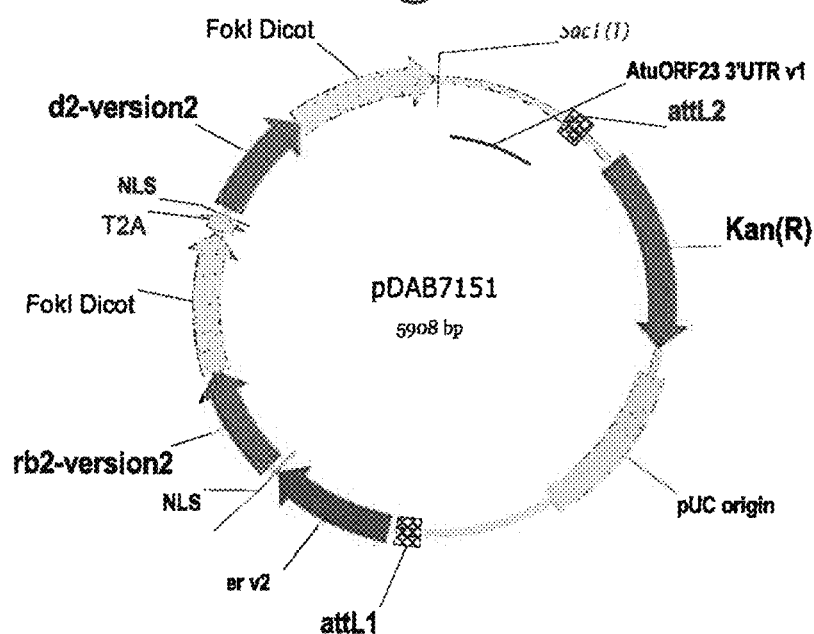
Figure 2E:
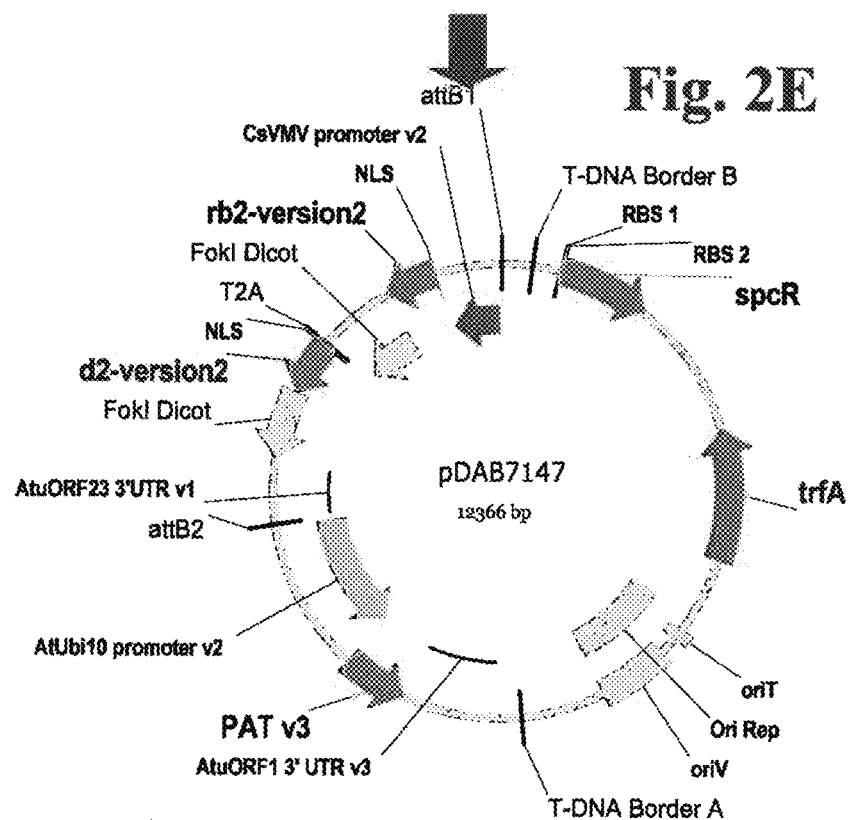
Figure 3A:
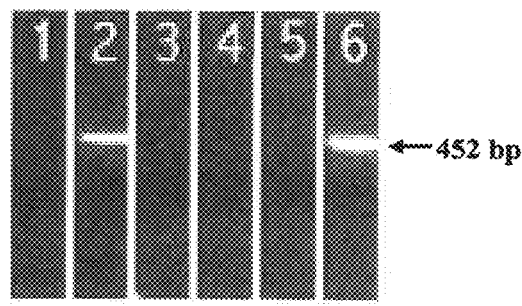
FIGS. 3A-3D show paralog-specific amplification of EPSPS genes.
Figure 3B:
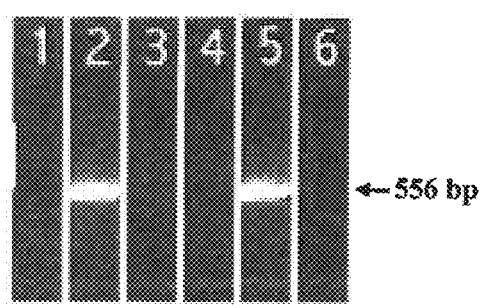
Figure 3C:
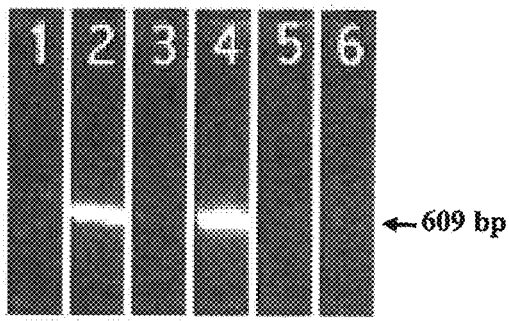
Figure 3D:
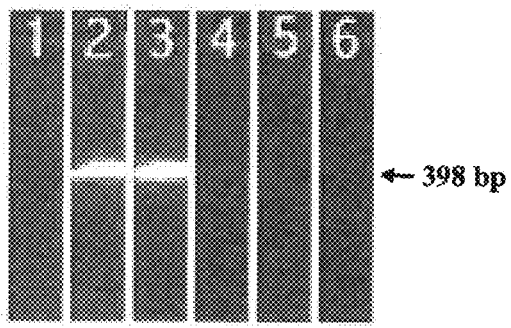

The gene cassettes encoding the ORFs of individual zinc-finger proteins were cloned into either the N2A or C2A vector by ligation using the restriction enzymes Kpn I and BamH I to create compatible ends. Next, the Bgl II/Xho I fragment from the C2A vector was inserted into the N2A vector using the same restriction sites, yielding an intermediate construct that contained a cassette including 2 ZFN-encoding domains flanked by Nco I and Sac I restriction sites (FIG. 2C).

Finally, the Nco I/Sac I cassette from this intermediate construction (FIG. 2C), containing both ZFN genes, was excised using those restriction enzymes and ligated into a plasmid backbone pDAB3731. The resulting plasmids, such as pDAB7151 (FIG. 2D), included the ZFN genes plus the relevant promoter and terminator sequences, plus selectable markers for plasmid maintenance (Table 2). The sequences were confirmed by restriction enzyme digestion and sequencing. In this construct, the ZFN expression cassette (including promoter and terminator elements) is flanked by attL sites for convenient manipulation using the GATEWAY system from Invitrogen (Carlsbad, Calif.). Each of the ZFN constructs generated using this cloning scheme were transformed into E. coli DH5α cells (Invitrogen, Carlsbad, Calif.) and subsequently maintained under the appropriate selection.

For Agrobacterium-mediated plant transformation, the ZFN cassettes were cloned into a binary construct using the GATEWAY LR CLONASE reaction (Invitrogen, cat #11791-019). The resulting binary construct (FIG. 2E) was confirmed via restriction enzyme digestion and then transformed into Agrobacterium tumefaciens strain Z707s. Colonies containing the clone were confirmed via restriction enzyme digestion and sequencing reaction.

B. Transient and Stable Expression Systems

Plasmid preparations of ZFN expression constructs, such as pDAB 7151, as depicted in FIG. 2, were generated from 2 L cultures of E. coli grown in LB media containing antibiotics using an endonuclease-free GIGAPREP kit (Qiagen, Valencia, Calif.) as per the manufacturer's recommendations. Plasmid DNA was delivered directly to B. napus hypocotyl cells using a variety of methods.

In one example of transient ZFN delivery, canola hypocotyl segments were subjected to DNA delivery by whiskers-mediated transient transformation of hypocotyl segments. Seeds of B. napus, var. Nex710 were surface-sterilized with 10% (v/v) CLOROX (5.25% sodium hypochlorite) for 10 minutes and rinsed 3 times with sterile distilled water. Subsequently, seeds were germinated on ½ concentration MS medium (½ MS basal salts with vitamins, 1% sucrose, 0.8% Agar, pH 5.8) contained in Phytatrays with 25 seeds per Phytatray. The seeds were placed in a culture room to germinate for 5 days at 23° C. with a photoperiod of 16 hours light, 8 hours dark. On day 5, hypocotyl segments, 3 mm in length, were aseptically excised and placed in sterile water to prevent drying while additional segments were cut. The shoot and root sections were discarded. The sections were placed horizontally on top of a piece of sterile filter paper, resting on the surface of MSK1D1 media (MS basal salts with vitamins, 1 mg/L kinetin, 1 mg/L 2,4, dichlorophenoxyacetic acid [2,4-D], 30 g/L sucrose, 7 g/L TC agar, pH 5.8). Segments were cultured for 3 days at 23° C. and 16 hours of light.

On the day of whiskers treatment, 300 partially callused hypocotyl segments were placed in a Sorvall bottle along with 30 ml of 'high osmotic media' (MS salts with B5 vitamins, 4.42 mg/L 2,4-D, and 12% sucrose) for a one hour pre-treatment at room temperature. This pre-treatment is a means of partially plasmolyzing the tissue in an attempt to ameliorate cellular damage when the cell wall is breached during subsequent whiskers treatment. Subsequently, 8.1 ml of 5% Silar SO-9 silicon carbide whisker (Advanced Composite Materials, LLC Greer, S.C.) solution and 170 µg of the non-binary ZFN plasmid DNA (Table 2) prepared as described above, were added to the Sorval bottle. The bottle was then agitated vigorously for 30 seconds on a paint mixer (Red Devil Equipment Co., Minneapolis, Minn.) in which the paint can clamp assembly was retrofitted to hold a Sorval bottle. After agitation, 100 ml of 'high osmotic media' was immediately added to the bottle which is then left to recover for 20 minutes at room temperature. Segments were then retrieved by pouring the contents of the bottle through a sterile, appropriately sized wire mesh to separate the segments from the whiskers and liquid contents of the bottle. Finally, segments were placed back on a fresh plate of MSK1D1 media with filter paper. Samples of about 100 mg were taken for transient expression analysis at days 1, 2, 3, and 7 after whiskers treatment.

In another example, the transient delivery system used polyethylene glycol (PEG)-mediated transformation of hypocotyl protoplasts. Protoplasts were prepared from the hypocotyl tissues of B. napus, var. Nex710, seedlings using the methods described by Sun et al. (Can. J. Bot. (1998) 76: 530-541) with modifications. Seeds were surface-sterilized and germinated for 7 days on ½ MS Canola medium as described above. One gram of hypocotyls was collected for each treatment. The hypocotyls were cut into thin sections of ≤1 mm in size and placed in MS9m medium (9% mannitol, 5 mM MES, 10 mM arginine, 0.3% polyvinylpyrolydon-40 (PVP-40)) contained in 100 mm petri plates. After all the hypocotyl sections were placed in the petridish, the liquid medium was removed with a pipette and replaced with 6 ml of enzyme solution (MS9m containing 0.1% Macerozyme-R10 (Yakult Honsha Co. Ltd, Tokyo, Japan), 1% Cellulase-R10 (Yakult Honsha Co. Ltd, Tokyo, Japan), 1% Pectinase (Sigma Chemical Co.).

The tissues were placed in the dark at 25° C. for 16 hours with gentle shaking on a rotary shaker at 40 rpm to digest the cell walls. After incubation, the enzyme—protoplast solution was filtered under aseptic conditions through a 100 µm cell strainer (Sigma Chemical Co.) placed on top of a 50 ml disposable centrifuge tube. The solution was centrifuged at 50×g for 5 minutes. After discarding the supernatant, the protoplast pellet was re-suspended in 4 ml of MS9m medium. The protoplast suspension was gently layered on top of 4.5 ml of MS with 0.5 M sucrose solution in a 15 ml centrifuge tube and centrifuged at 50×g. The protoplasts were withdrawn with a micropipette from a thick band located at the interphase and washed with 5 ml of MS9m medium by centrifuging at 50×g for 5 minutes.

For DNA treatment, the protoplast pellet was resuspended in 200 µl of Mg-mannitol solution to a final concentration of $1 \times 10^5$ protoplasts/ml. A 50 µl sample of a non-binary plasmid DNA, such as pDAB7151 (Table 2), was added to 200 µl protoplast solution contained in a 15 ml disposable sterile centrifuge tube and mixed. An equal volume of 40% PEG-3350 solution (Sigma Chemical Co) was added to the protoplast solution and incubated at room temperature for 20 minutes. Subsequently, 0.8 ml W5 medium (125 mM CaCl$_2$.H$_2$O, 154 mM NaCl, 5 mM KCl and 5 mM glucose) was added and incubated for an additional 10 minutes followed by centrifugation at 180×g for 3 minutes. The PEG solution was removed with a pipette and the protoplasts resuspended in 1 ml WI solution. The tubes were then incubated in the dark for about 18 hours followed by centrifugation at 180×g for 3 minutes. The supernatant was removed, and 100 µl of protoplast suspension was transferred to a 2 ml Eppendorf tube. Protoplasts ($10^5$/ml) were collected at 0, 1, 2, 3 days post-DNA treatment and stored at −80° C. until analysis. A 10 µl sample of the protoplast suspension was mixed with fluorescein diacetate stain, and viable protoplasts were counted in a haemocytometer.

In another example, the transient delivery system used Agrobacterium-mediated transformation of the hypocotyl segments. The segments were cultured on sterile filter paper on callus induction medium MSK1D1 and were given a 3-day pre-treatment as described above for the whiskers protocol. The day before Agrobacterium treatment, bacterial culture (1 loop) of a binary plasmid such as pDAB7147 (Table 2) was inoculated in a flask containing 35 ml of YEP medium containing the appropriate antibiotics. The bacterial culture was allowed to grow overnight for ~16 hrs in the dark at 28° C. with constant shaking at 200 rpm. The next day, Agrobacterium solution was prepared to a final concentration of Klett 50 in liquid M medium. Hypocotyl segments were transferred from the filter paper to 100×25 mm petri dish containing 40 ml of Agrobacterium suspension and incubated for 30 min at room temperature with periodically swirling every 10 minutes. At the end of the treatment period, the Agrobacterium solution was removed and the hypocotyl segments were transferred back to the original plates containing MSK1D1 medium with filter paper. The segments were co-cultivated for 3 days in Percival or culture room under reduced light intensity by covering the plates with aluminum foil.

After 3 days of co-cultivation, the segments were transferred onto a callus induction medium MSK1D1TC (MS, 1 mg/l Kinetin, 1 mg/l 2,4-D, 0.5 gm/l MES, 5 mg/l AgNO3, 300 mg/l Timentin, 200 mg/l Carbenicillin, 3% sucrose, 0.7% Phytagar). About 100 mg of hypocotyl tissues were taken 0, 2, 3, 4, and 7 days post Agrobacterium treatment and stored at −80° C. until analysis.

In one example of ZFN delivery using a stable transgenic expression system, seeds of Brassica napus var. Nex710 were surface-sterilized, germinated for 5 days, prepared ≤1 mm hypocotyl segments, and pre-treated for 3 days as described for the whiskers treatment. After 3 days, the hypocotyl segments were treated with any of the binary Agrobacterium strains (Table 2) and co-cultivated for 3 days as described for Agrobacterium-mediated transient expression system as described above.

After 3 days of co-cultivation, 300 hypocotyl segments were transferred onto callus induction medium MSK1D1H1 (MS, 1 mg/l Kinetin, 1 mg/l 2,4-D, 0.5 gm/l MES, 5 mg/l AgNO3, 300 mg/l Timentin, 200 mg/l Carbenicillin, 1 mg/l Herbiace, 3% sucrose, 0.7% Phytagar) with a low level of herbicide selection for 7 days. The hypocotyl segments were then transferred to MSK1D1H3 medium containing higher levels of selection (MS, 1 mg/l Kinetin, 1 mg/l 2,4-D, 0.5 gm/l MES, 5 mg/l AgNO3, 300 mg/l Timentin, 200 mg/l Carbenicillin, 3 mg/l Herbiace, 3% sucrose, 0.7% Phytagar) for 2 weeks and subsequently transferred to MSK1D1H5 medium (MS, 1 mg/l Kinetin, 1 mg/l 2,4-D, 0.5 gm/l MES, 5 mg/l AgNO3, 300 mg/l Timentin, 200 mg/l Carbenicillin, 5 mg/l Herbiace, 3% sucrose, 0.7% Phytagar) for another 2 weeks. A total of 203 and 227 callus lines were obtained for each of the binary constructs (Table 2), giving callus frequency of 67.6% and 75.5% respectively. Fifty random callus lines were then subject to DNA analysis following 5-7 weeks post Agrobacterium treatment.

C: EPSPS Paralog Analysis for Targeted ZFN-Mediated Double-Strand Cleavage

Functionality of a ZFN in this example is understood to include (but not be limited to) the ability of a ZFN to express in cells of a crop species, and for that ZFN to mediate a double-stranded (ds) break in the endogenous genome of that crop through recognition of, binding to and cleavage of its desired target. It is also understood that, in this example, the target of the ZFN is a gene in an endogenous locus and its conformation within the crop genome. In order to assess whether engineered ZFNs have functionality against the predicted target gene in a genomic context, DNA-sequence based assays were deployed. ZFN-induced ds-breaks in DNA are predicted to induce repair mechanisms such as non-homologous end joining (NHEJ) (reviewed by Cahill et al. (2006) Front Biosci. 1:1958-1976). One outcome of NHEJ is that a proportion of the broken DNA strands will be repaired in an imperfect manner, resulting in small deletions, insertions or substitutions at the cleavage site. One skilled in the art may detect these changes in DNA sequence through a variety of methods.

For identification of NHEJs in the EPSPS paralogs, gene-specific assays were developed with PCR-based approaches. Sufficient sequence differences in four of the five EPSPS paralogs, A, B, C and D, permitted development of paralog-specific assays. Sequences of paralogs D and E could not be sufficiently differentiated at the targeted locus, which resulted in developing only one assay representing both of the paralogs. PCR amplification was carried out using oligonucleotide primers specific for the target gene and flanking the predicted cleavage site of the ZFN. Paralog-specific PCR primers were as follows:

Paralog A:

Forward orientation primer:
(SEQ ID NO: 17)
5'-TCCCAGCTTCTTTAGATTCTAAGG-3'

Reverse orientation primer:
(SEQ ID NO: 18)
5'-CTGCAACTTTTCACATAGCAA-3'

Paralog B:

Forward orientation primer:
(SEQ ID NO: 19)
5'-CAAGAGTGATATCGAGTTGTACCTTGGGAATGCT-3')

Reverse orientation PCR primer:
(SEQ ID NO: 20)
5'-AGGCCATCATATCGAGCAAACGCAGT-3'

Paralog C:

Forward orientation primer:
(SEQ ID NO: 21)
5'-GGGTAAACAACCGTGCTGTA-3'

Reverse orientation primer:
(SEQ ID NO: 22)
5'-AAAGACTGCTGCAAACAAGATC-3'

Paralog D/E:

Forward orientation primer:
(SEQ ID NO: 23)
5'-GGTTGTTGAAGGATGCGGT-3'

Reverse orientation primer:
(SEQ ID NO: 24)
5'-GCAAACAATTCATAGAGTAAATGTG-3'

All forward and reverse orientation PCR primers were used in combinations for a given paralog to amplify either purified genomic DNA or positive control plasmid DNA containing each of the paralogs under the following conditions: 25 µl reaction volume containing 2.5 µl DNA template (10 ng/µl) or plasmid DNA positive control (1 ng/µl), 0.625 µl each primer (at 10 µM each), 2.5 µl of 10× ACCUPRIME PCR buffer II, and 0.15 µl (0.75 units) ACCUPRIME Taq DNA polymerase (Invitrogen, Carlsbad, Calif.) in the enzyme manufacturer's buffer. Amplification was executed in the ICYCLER IQ (Bio-Rad, Hercules, Calif.) using the following parameters: 94° C. for 2 minutes, 35 cycles of (94° C. for 30 seconds, annealing (see gradient below) for 30 seconds, 68° C. for 1 minute), 68° C. for 10 minues, 4° C. held indefinitely.

A gradient was run to determine the optimal reaction conditions. The gradient temperature was between 65.0° C. and 50.0° C. Paralog A, B, C and D/E showed the best amplification at 62.1° C., 65.0° C., 65.0° C., and 59.3° C. annealing temperatures respectively (FIGS. 3A-3D), and these temperatures were used in subsequent studies. The PCR products for all 4 paralogs were cloned into the TOPO pCR 2.1 vector (Invitrogen, Carlsbad, Calif.) and confirmed by sequencing for paralog-specific amplification.

The three transient methods and one stable method of ZFN delivery to hypocotyl cells, as described above, were compared to identify the most effective method for assessing ZFN efficacy (determined by the presence of the highest number of NHEJs). Paralog D-specific ZFNs that were proven efficacious in kidney 293 cells were used in this study. These ZFN proteins were predicted to bind to 2 short EPSPS gene-specific sequences of paralog D to create a heterodimeric nuclease that cleaves the double-stranded DNA (FIG. 4). These ZFN genes were present in four constructs; two binary constructs, pDAB7147 and pDAB7150, that were specific for *Agrobacterium*-mediated transformation and the remaining two constructs, pDAB7151 and pDAB7154, for transient transformation, (Table 2). The stably transformed callus tissue was further categorized into "green" and "brown" samples, with the possibility of higher ZFN expression in the "brown" tissue and hence, the chance of higher frequencies of NHEJs. The latter might have lead to cell toxicity causing the tissues to turn "brown." All samples were collected (see section 4B), including untreated controls, frozen, and lyophilized except for the protoplast samples, which were used directly for DNA isolation. Genomic DNA was isolated by the Qiagen method as described above. 3 µg of all genomic DNA was digested with 5 units of Mae III restriction endonuclease (Roche Applied Science, Indianapolis, Ind.) overnight per the manufacturer's recommendations.

The DNA was then purified by ethanol precipitation by adding 0.1 volume of 3 M sodium acetate, pH 5.2 and 2 volumes of 100% ethanol followed by centrifugation in a microfuge for 5 minutes at 10,000 g. The DNA was then washed with 70% ethanol, and the pellet was dried in a SPEEDVAC evaporator (Savant) and resuspended in water. The DNA was then subjected to a second Mae III digestion overnight and precipitated with ethanol as noted before. The restriction enzyme site is located between the two monomeric ZFN binding locations of a pair (FIG. 4), and close to where the Fok1 domains dimerize and induce double-stranded breaks in the genomic DNA. Hence, the restriction enzyme digestion enriches for fragments that have undergone NHEJs resulting in the loss of the restriction enzyme recognition sites.

PCR amplification was then carried out using oligonucleotide primers specific to paralog D and flanking the predicted cleavage site of the ZFN. The forward orientation PCR primer (5'-GGTTGTTGAAGGATGCGGT-3') (SEQ ID NO:23) and reverse orientation PCR primer (5'-GCAAACAATTCATAGAGTAAATGTG-3') (SEQ ID NO:24) specific for the targeted EPSPS paralog D were used in combination to amplify purified genomic DNA under the following conditions: 55 µl reaction volume containing 10 µl Mae III digested gDNA (26.4 ng) template, 1.25 µl of each primer (at 10 µM each), 5 µl of 10× ACCUPRIME PCR buffer II, 5 µl of 10% PVP-40 and 1 µl (5 units) ACCUPRIME TaqDNA polymerase (Invitrogen, Carlsbad, Calif.). Amplification products of the expected size resulted from amplification cycles consisting of 94° C. for 2 minutes, 40 cycles of (94° C. for 30 seconds, 59.3° C. for 30 seconds, 68° C. for 1 minute), 68° C. for 10 minutes, and 4° C. held indefinitely. The amplified fragments were directly cloned into the vector pCR2.1 using the TA cloning kit from Invitrogen (Carlsbad, Calif.).

Approximately 90 individual cloned fragments per time point per treatment were sequenced using the M13 Forward and M13 Reverse priming sites present on the pCR 2.1 vector. Untreated controls were included for a given treatment. Approximately 3000 clones were sequenced this way.

Figure 5:
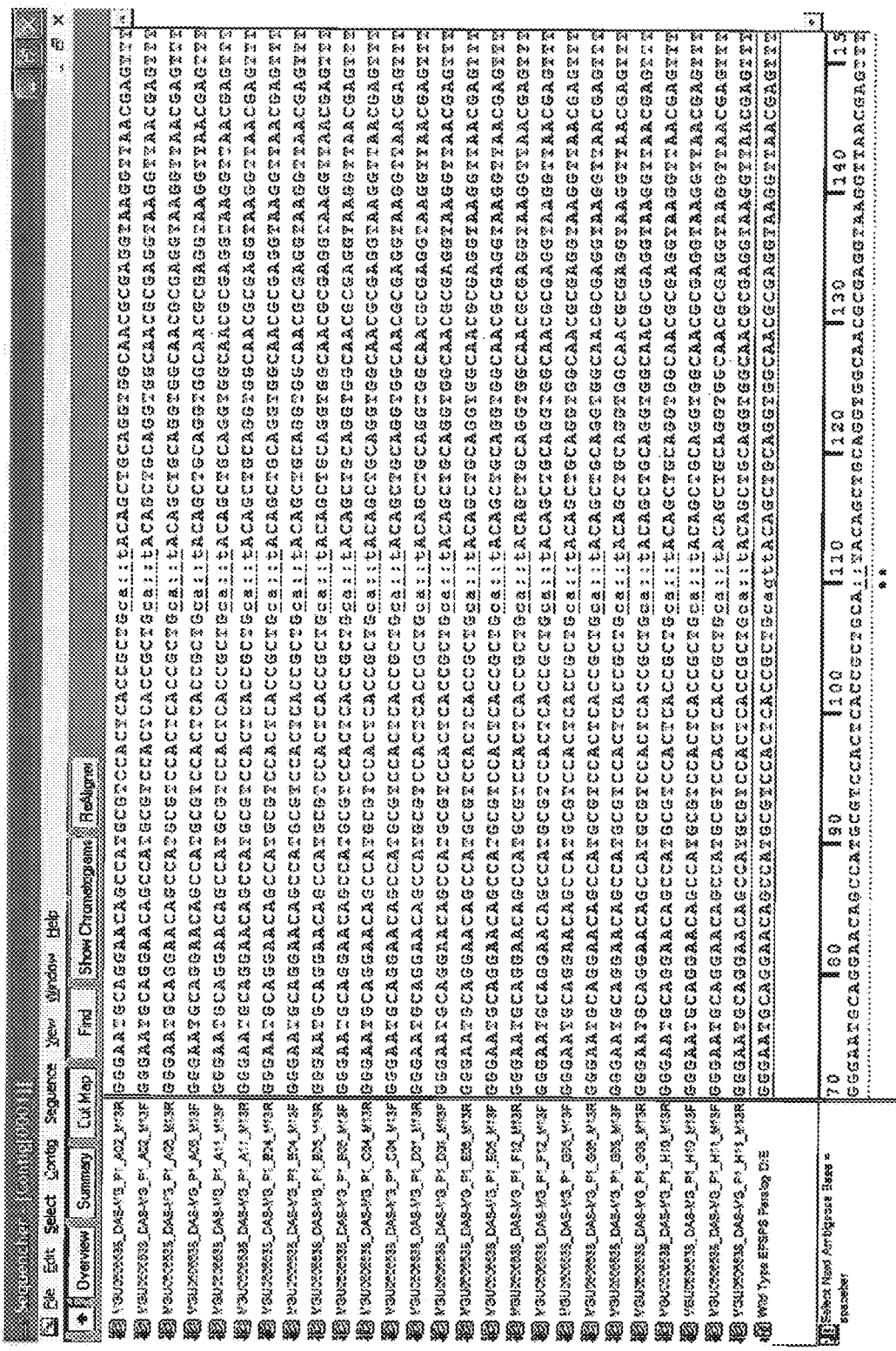
FIG. 5 shows a ZFN-mediated deletion in the EPSPS paralog D. A 2 bp deletion resulted from the non-homologous end joining (NHEJ) repair of a ZFN-mediated double-stranded DNA break present in the EPSPS paralog D *B. napus*. The cleavage target for the ZFN pDAB7151 was CAGTT, which corresponds to the 2 bp GT deletion. Bottom: predicted wild-type sequence (SEQ ID NO: 52). Top: alignment of 26 sequences of paralog D clones (SEQ ID NO: 53) with Sequencher software showing the 2 bp deletion. These sequences were obtained from both forward and reverse primer sequencing of 13 clones.
Figure 9A:
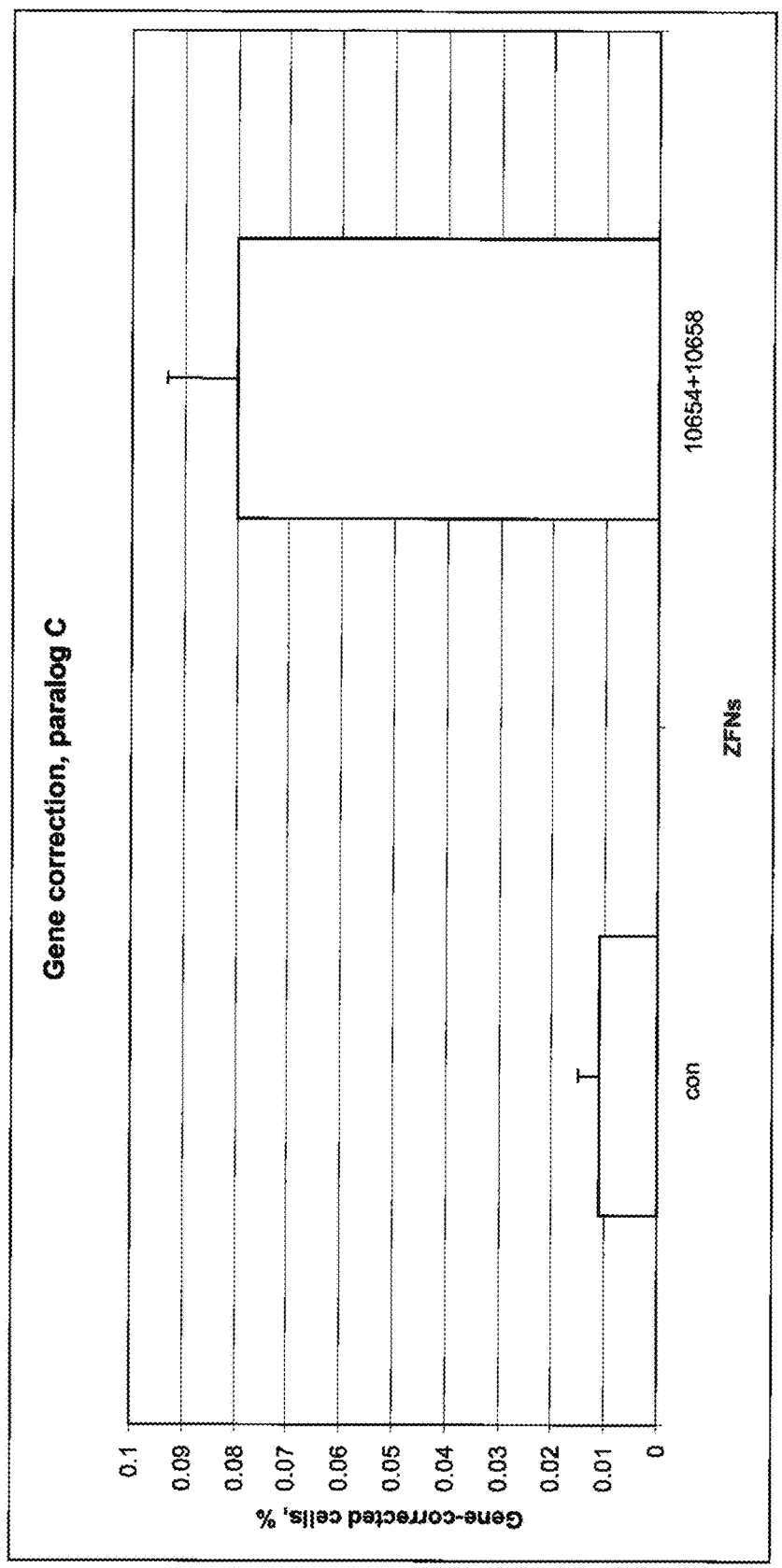
FIGS. 9A-9E are graphs depicting gene correction activity of exemplary EPSPS ZFNs (see also Example 3) in kidney 293 reporter cells.
Figure 9B:
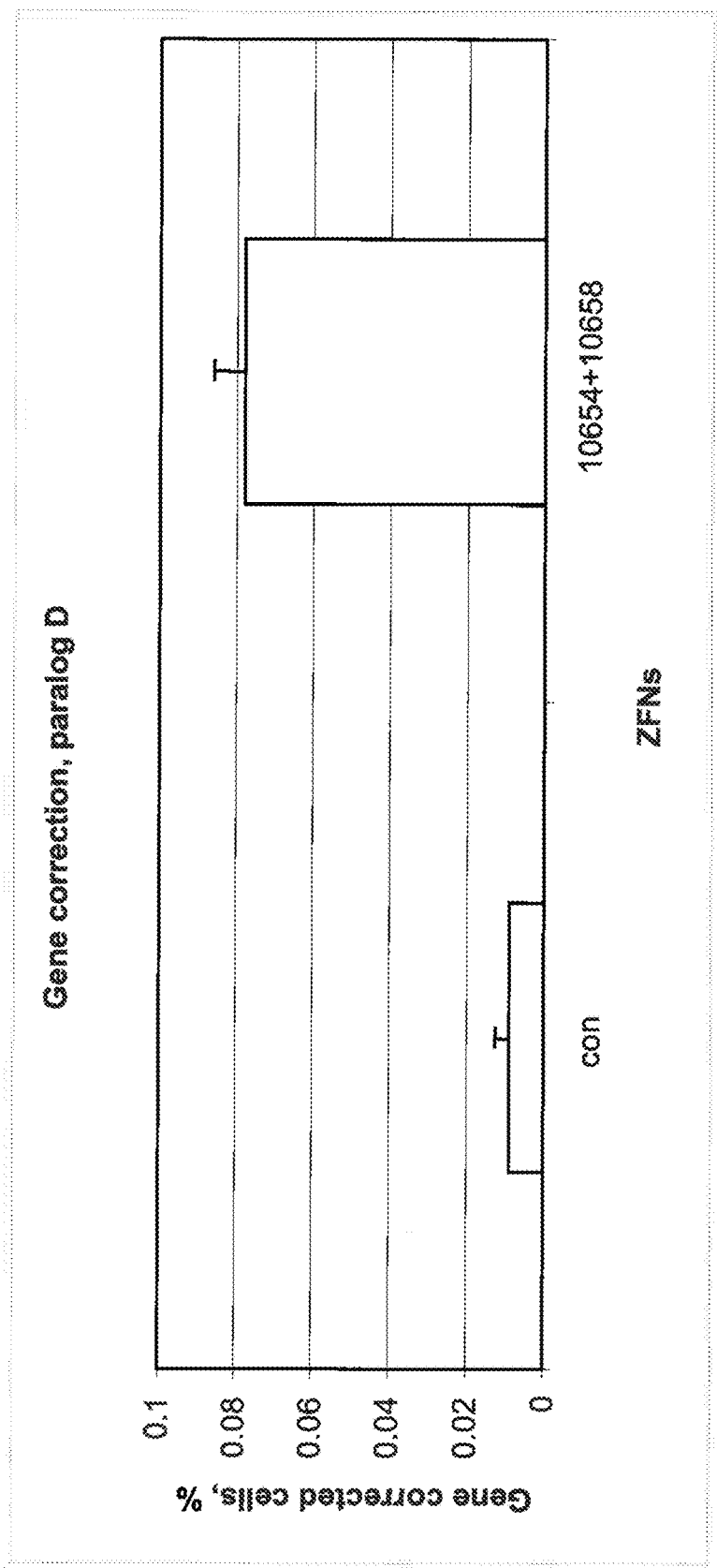
Figure 9C:
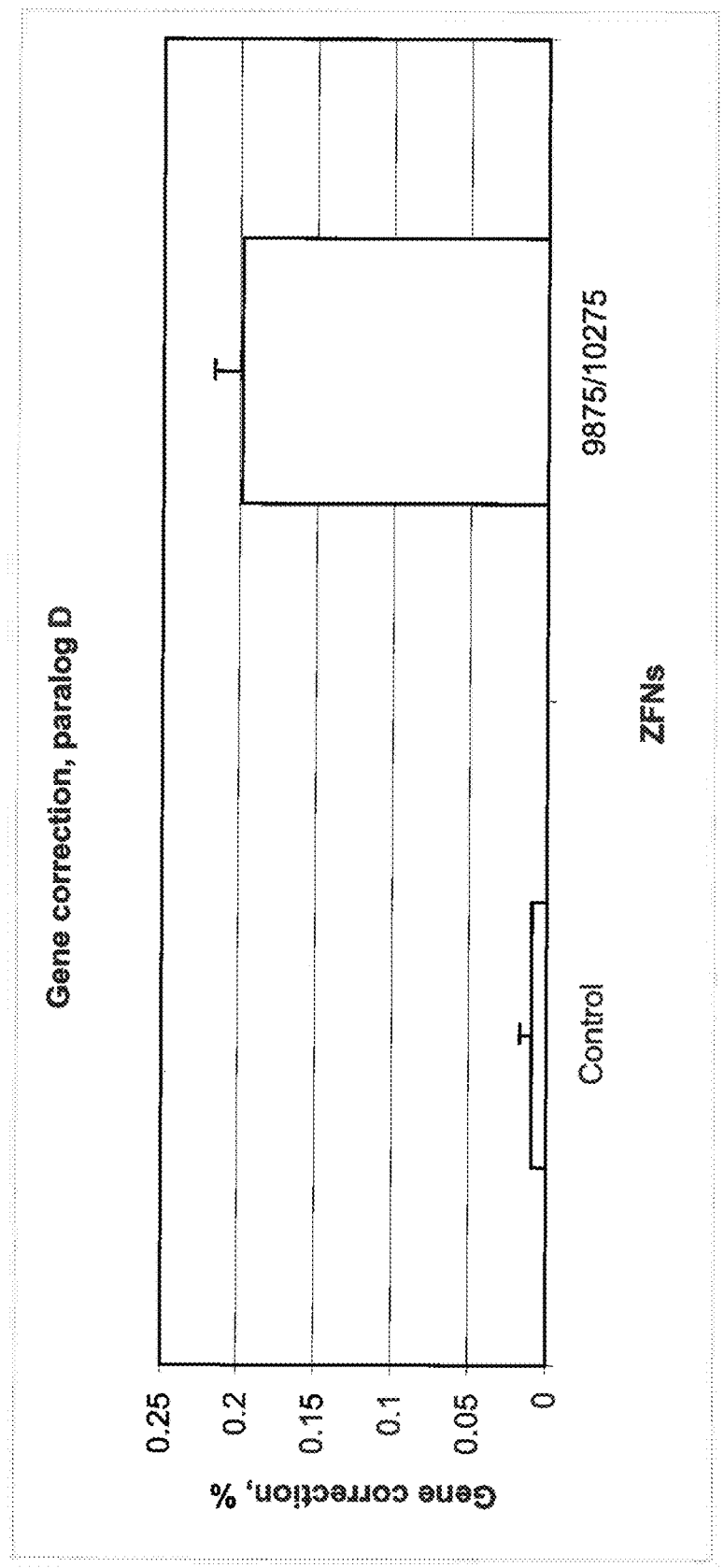
Figure 9D:
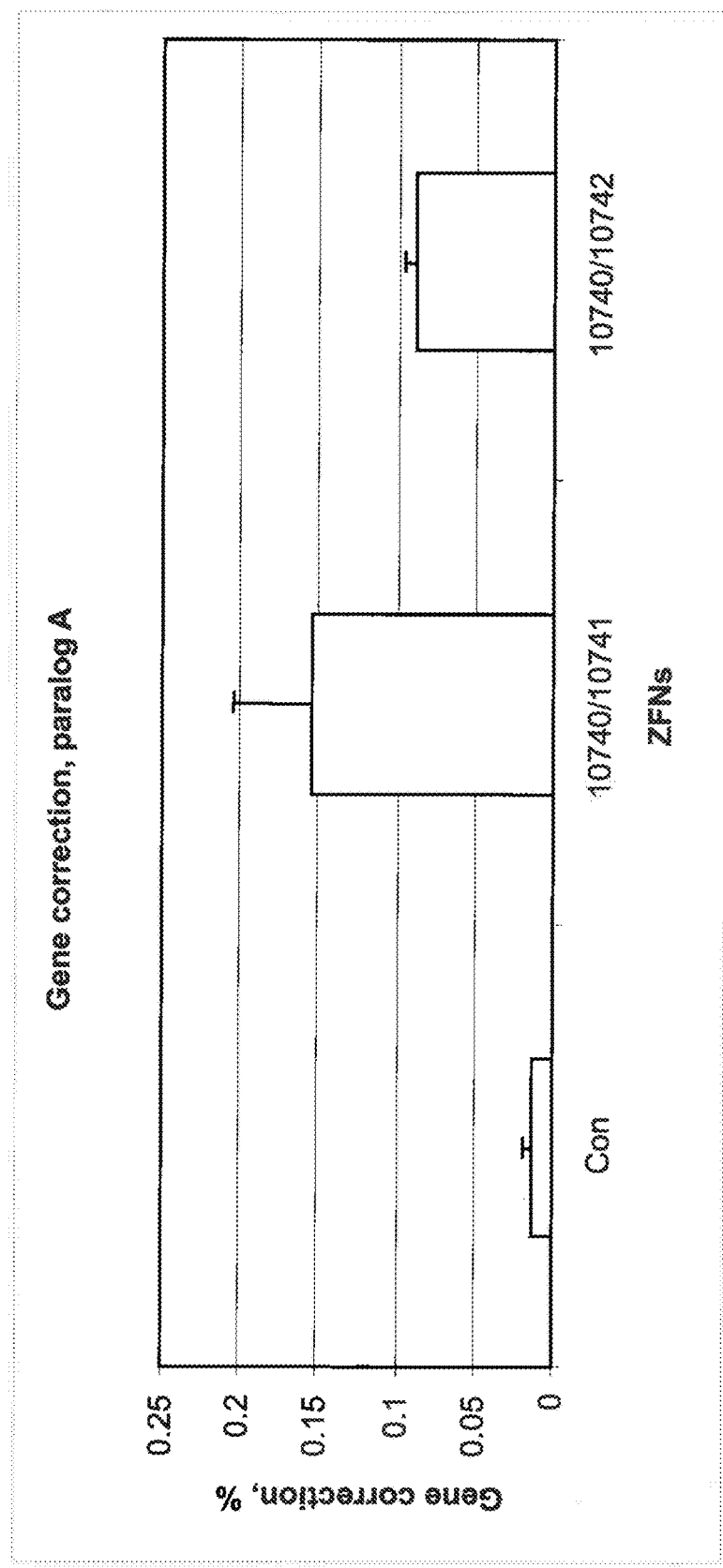
Figure 9E:
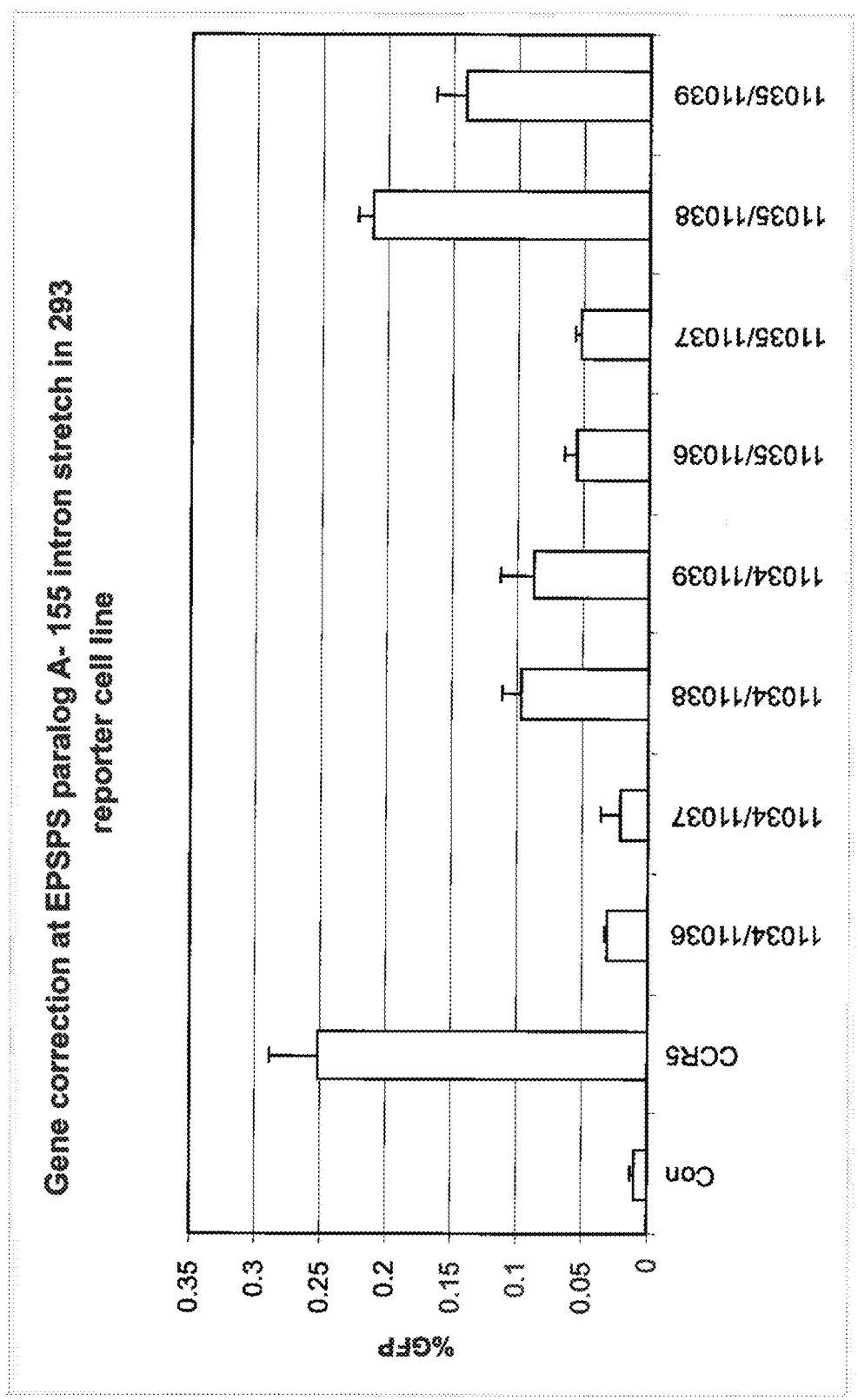
Figure 14A:
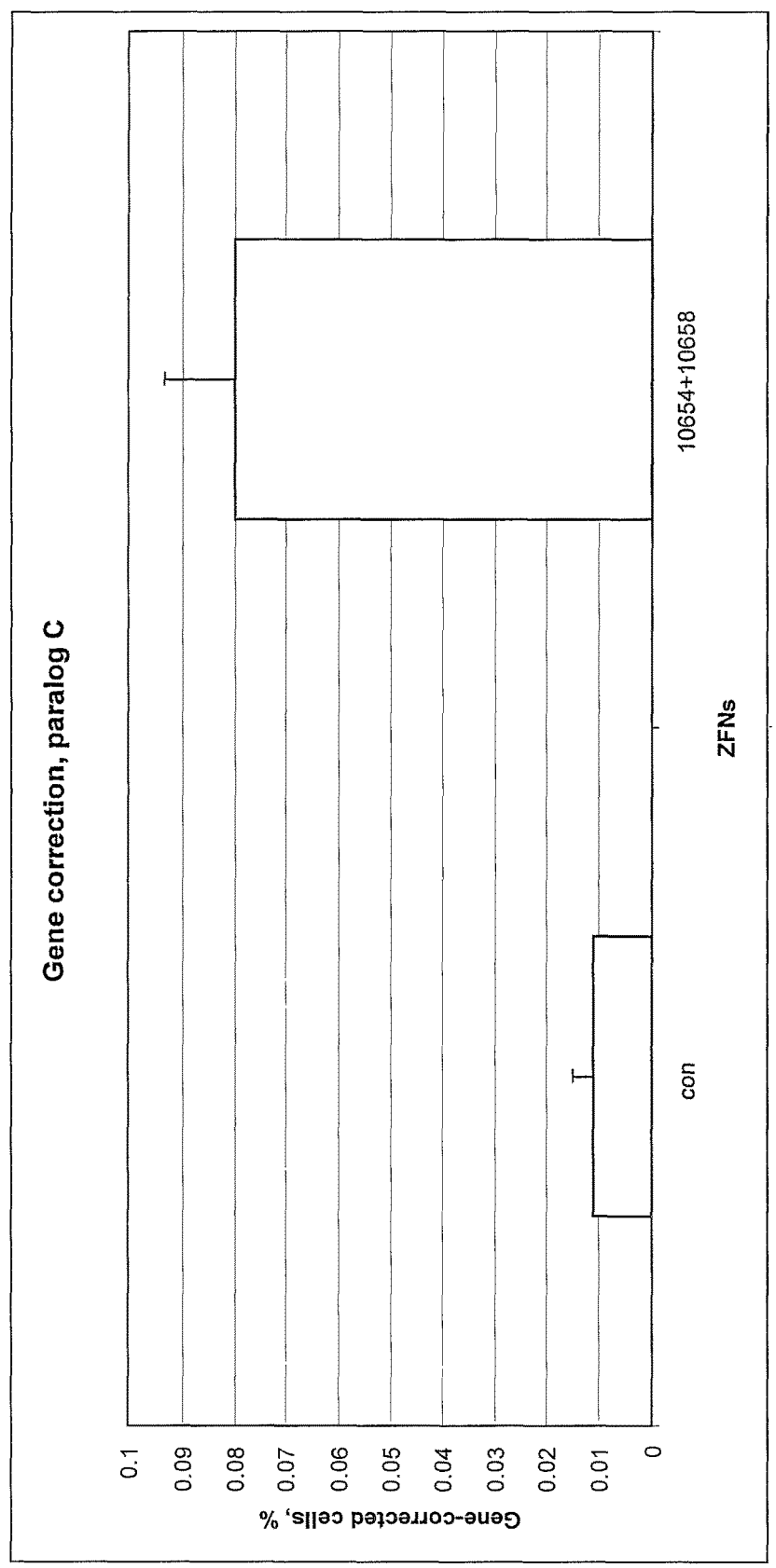
Figure 14B:
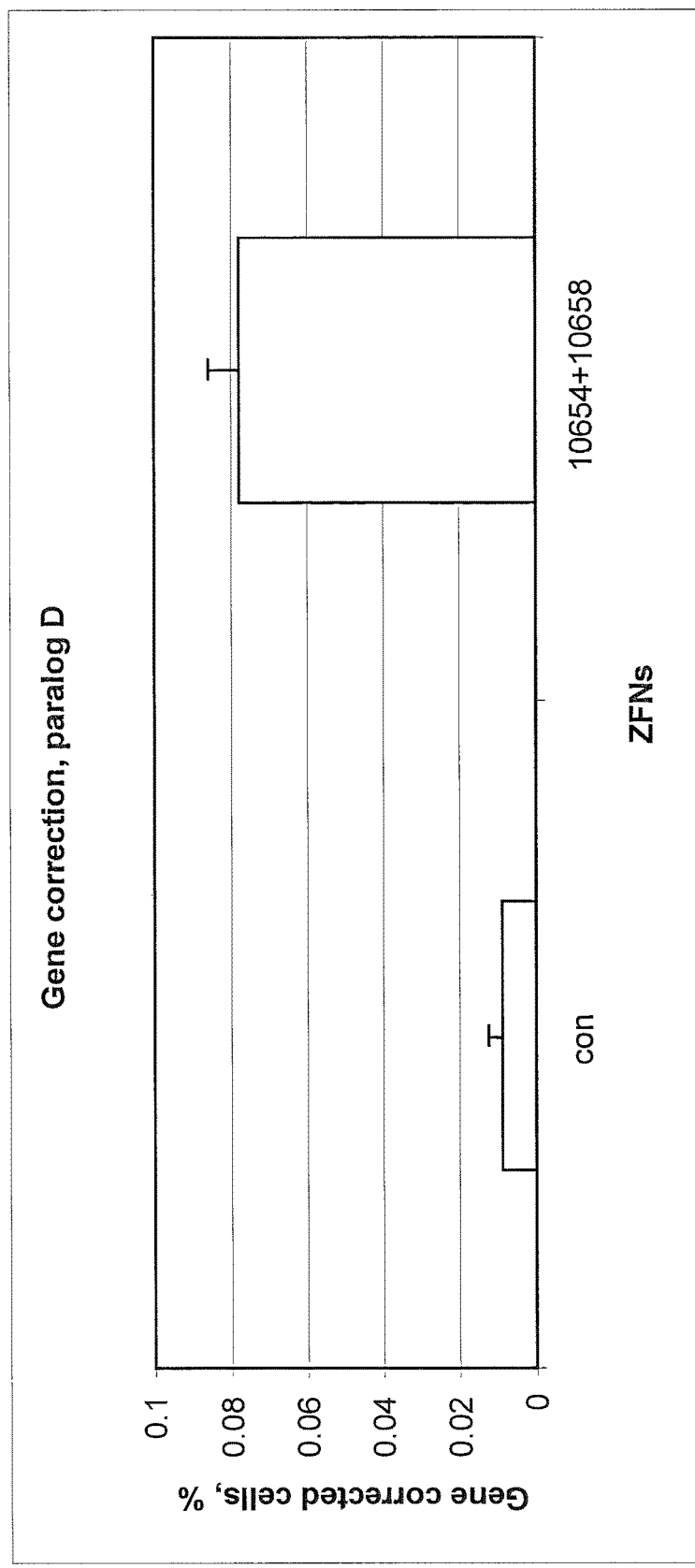
Figure 14C:
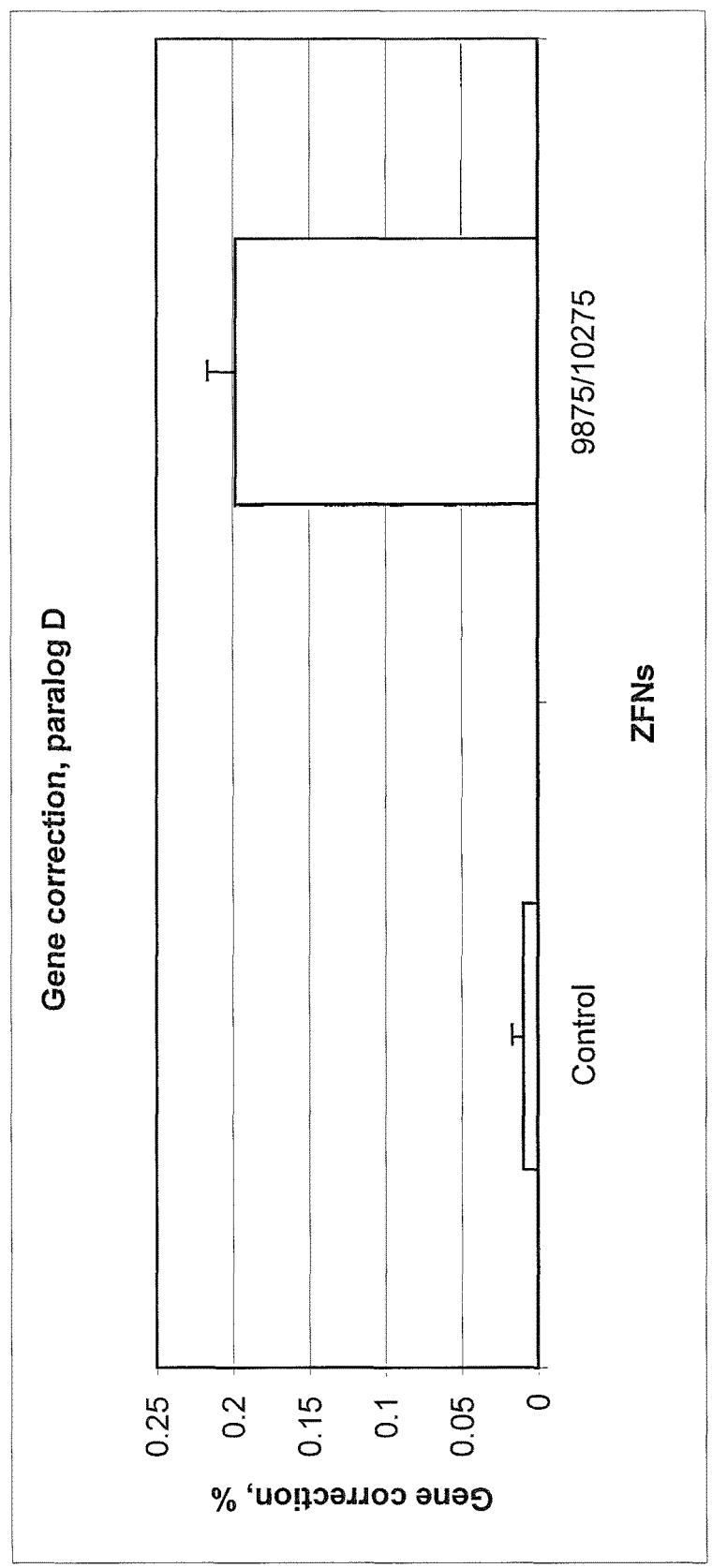
Figure 14D:
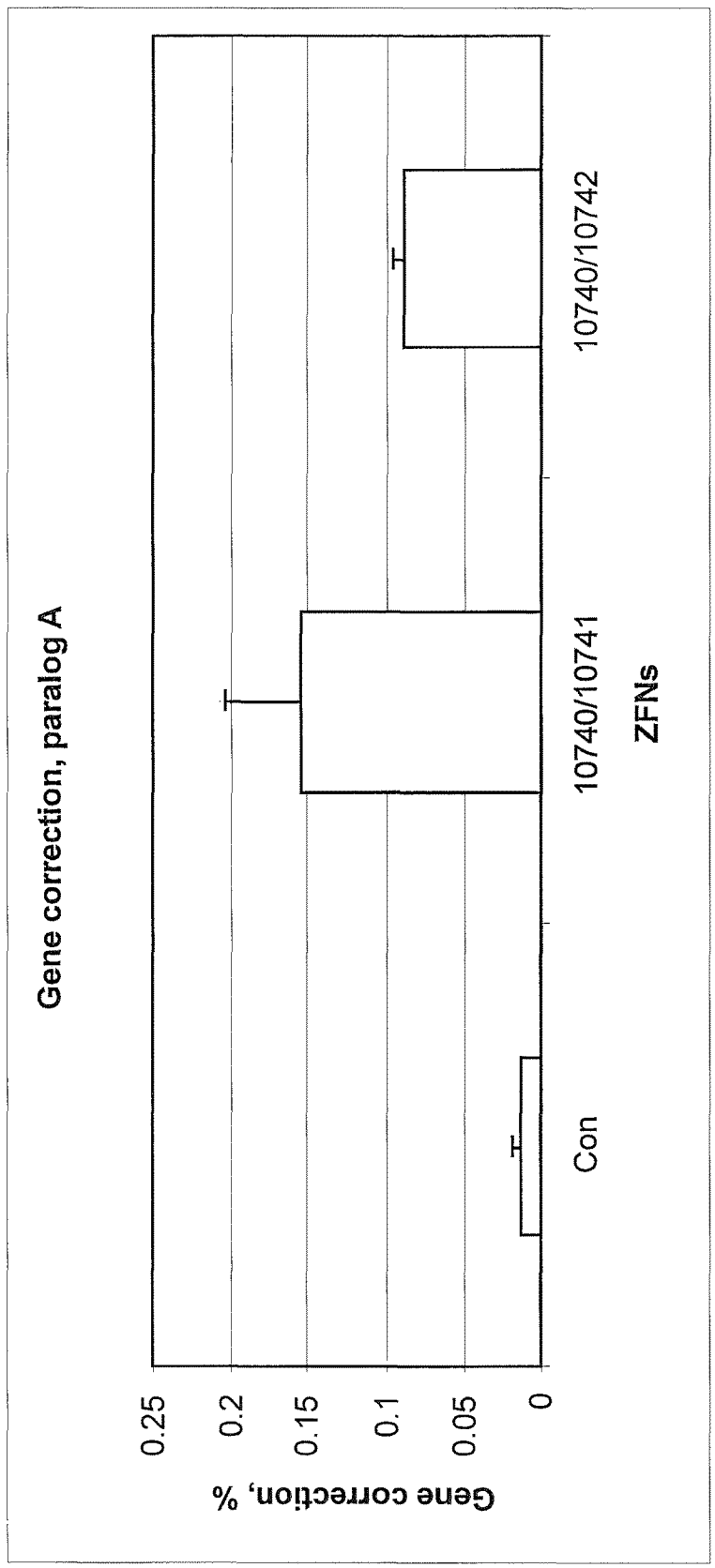
Figure 14E:
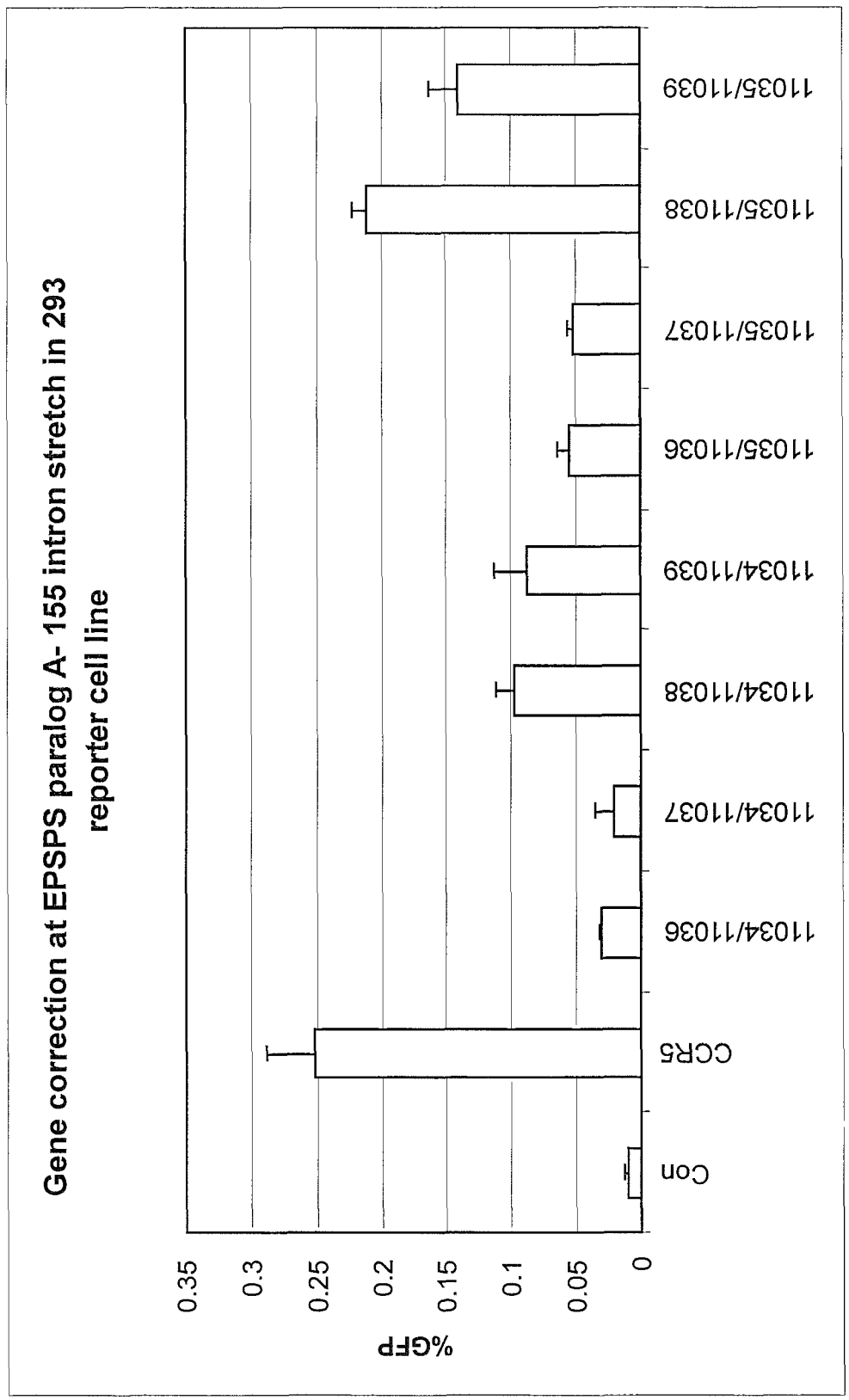

Analysis of all sequencing results across two different ZFN treatments revealed 13 clones (confirmed by both forward and reverse sequencing primers) containing a small deletion at precisely the predicted cleavage site of the ZFN present in pDAB7151, indicating that the NHEJ mechanism had mediated an imperfect repair of the DNA sequence at that site (FIG. 5). These particular clones were obtained from the protoplast DNA samples 3 days post-ZFN transformation. These results demonstrated the ability of the engineered ZFNs to induce targeted, double-stranded breaks in a specific manner at an endogenous gene locus within a crop species. No NHEJs were observed in any other method of ZFN treatment with this type of sequencing.

D. Massively Parallel Sequencing Analysis

In another example, a combination of PCR and massively-parallel pyrosequencing methods were applied to interrogate paralog D in the samples as obtained above. The same set of forward and reverse paralog D-specific primers (SEQ ID NO:23 and SEQ ID NO:24) were used to amplify the DNA of all samples representing the 3 transient and one stable method of ZFN transformation into canola hypocotyl cells. Amplification conditions were as described above.

This primary amplification product was then purified using the MINELUTE PCR purification kit (Qiagen, Valencia, Calif.), and eluted the DNA in 10 µl. A second set of nested primers were designed to amplify an approximately 100 bp fragment suited for massively parallel sequencing. Six variants of the forward orientation PCR primer (5'-XXX AGTTGTACCTTGGGAATG-3') (SEQ ID NO:25) in which XXX=GGC, CGC, GGC, CGG, CCG, or GCG, and six variants of the reverse orientation PCR primer (5'-XXX ATCAATTTCTTGACAATAACA-3') (SEQ ID NO:26) in which XXX=GGC, CGC, GGC, CGG, CCG, or GCG, were synthesized and HPLC purified (IDT, Coralville, Iowa). The 3-bp tags at the 5'-end of each primer served as an identifier key and indicated which cell sample the amplicon originated from. Primer pairs with matching identifier tags (keys) were used in combination to amplify purified primary PCR amplicon derived from samples described above under the following conditions: 50 µl reaction volume containing 10 µl of purified PCR amplicon diluted 1:10, 1.25 µl each primer (10 µM each), 5 µl 10× ACCUPRIME PCR buffer 1 and 0.3 µl (1.5 units) ACCUPRIME TaqDNA high fidelity polymerase (Invitrogen, Carlsbad, Calif.) in the enzyme manufacturer's buffer. Amplification products of the expected size resulted from amplification cycles consisting of 94° C. for 2 minutes, 30 cycles of (94° C. for 30 seconds, 62° C. for 30 seconds, of 68° C. for 30 seconds), 68° C. for 5 minutes, and 4° C. held indefinitely and were purified using the MINELUTE PCR purification kit (Qiagen, Valencia, Calif.) as per the manufacturer's recommendations.

Massively parallel pyrosequencing reactions (also known as 454 sequencing) were performed directly on PCR products as described in (Margulies et al. (2005) Nature 437: 376-380). Analysis of 454 sequencing results was carried out by identifying sequence reads containing deletions of the expected size and position within the DNA molecule. Results of these analyses indicated the presence of multiple small 9-12 bp deletions at the expected cleavage site for these ZFNs, as shown in FIG. 6. Forty-six of the forty-eight deletions were observed in the sequence reads obtained from the green calli stably transformed with the ZFN construct, pDAB7147 (Table 3). Two additional deletions with the same ZFN pair were obtained, one from the transiently treated protoplast DNA (pDAB7151) and another from the hypocotyl tissue transiently treated with Agrobacterium (pDAB7147). These deletions were precisely localized at the ZFN target site and indicated that ds-breaks induced by the ZFN were generated, which were subsequently repaired by the NHEJ mechanism.

Since paralogs D and E were indistinguishable by the PCR assay used in this example, it is possible that either one or both of the paralogs were cleaved by the ZFN. These results further demonstrate the ability of the engineered ZFNs to induce targeted, double-stranded breaks in a specific manner at an endogenous gene locus within a crop species. It further proved that the stable method of ZFN transformation was the most effective method for screening NHEJs under the current experimental conditions. The ZFNs present in constructs pDAB7150 and pDAB7154 did not show any deletions across multiple samples treated with the different transformation methods (see Table 4).

TABLE 4

The results of massively parallel sequencing showing NHEJs in the targeted sequences of the EPSPS paralog D obtained from transient and stable transformation of B. napus hypocotyl segments with ZFNs pDAB7147 and pDAB7151. The control sample was comprised of tissues not treated with the ZFNs.

| S.N. | Sample | ZFN construct # | Sample #-Primer | Sequences analyzed | # of NHEJ |
|---|---|---|---|---|---|
| 1 | Control | pDAB7147 + pDAB7151 | 1-Forward | 18,215 | 0 |
| 2 | Control | pDAB7147 + pDAB7151 | 1-Reverse | 18,922 | 0 |
| 3 | Protoplast | pDAB7151 | 2-Forward | 45,896 | 0 |
| 4 | Protoplast | pDAB7151 | 2-Reverse | 48,606 | 1 |
| 5 | Whiskers | pDAB7151 | 3-Forward | 19,601 | 0 |
| 6 | Whiskers | pDAB7151 | 3-Reverse | 19,628 | 0 |
| 7 | Transient Agro. | pDAB7147 | 4-Forward | 31,281 | 1 |
| 8 | Transient Agro | pDAB7147 | 4-Reverse | 31,595 | 0 |
| 9 | Stable Agro-G | pDAB7147 | 5-Forward | 13,795 | 29 |
| 10 | Stable Agro-G | pDAB7147 | 5-Reverse | 13,221 | 17 |
| 11 | Stable Agro-B | pDAB7147 | 6-Forward | 8,167 | 0 |
| 12 | Stable Agro-B | pDAB7147 | 6-Reverse | 7,549 | 0 |
|  | Total |  |  | 276,476 | 48 |

In an effort to analyze ZFN-induced double-stranded breaks in other EPSPS paralogs, a combination of PCR and massively parallel pyrosequencing were performed to interrogate the DNA of the remaining EPSPS paralogs for ZFN-induced double-stranded breaks. Genomic DNA digested with MaeIII from the same "Green" stable calli transformed with Agrobacterium strain containing pDAB7147 and pDAB7150, as described in sections 4D-E, were employed. PCR amplification was then carried out with oligonucleotide primers specific for the EPSPS paralogs, A, B, C and D that anchored on the genomic DNA flanking the predicted cleavage site of the ZFN. A forward orientation PCR primer for paralog A (5'-TCCCAGCT-TCTTTAGATTCTAAGG-3') (SEQ ID NO:17) and reverse orientation PCR primer (5'-CTGCAACTTTTCACATAG-CAA-3') (SEQ ID NO:18), a forward orientation PCR primer for paralog B (5'-CAAGAGTGATATCGAGTTG-TACCTTGGGAATGCT-3') (SEQ ID NO:19) and reverse orientation PCR primer (5'-AGGCCATCATATCGAG-CAAACGCAGT-3') (SEQ ID NO:20), a forward orientation PCR primer for paralog C (5'-GGGTAAACAACCGTGCT-GTA-3') (SEQ ID NO:21) and reverse orientation PCR primer (5'-AAAGACTGCTGCAAACAAGATC-3') (SEQ ID NO:22) and the same set of forward and reverse primers for paralog D (SEQ ID NO:23 and SEQ ID NO:24), as described in sections 4 D-E, were used in combination to amplify the genomic DNA for each of the paralogs separately under the following conditions: 50 µl reaction volume containing 200 ng Mae III digested gDNA template (10 µl), 1.25 µl each primer (at 10 µM each), 5 µl of 10× Accuprime PCR buffer II, 5 nl of 10% PVP-40 and 0.3 nl (1.5 units) ACCUPRIME TaqDNA high fidelity polymerase (Invitrogen, Carlsbad, Calif.) in the enzyme manufacturer's buffer. Amplification products were generated from amplification cycles consisting of 94° C. for 2 minutes, 25 cycles of (94° C. for 30 seconds, annealing for 30 seconds, 68° C. for 1 minute), 68° C. for 5 minutes, 4° C. held indefinitely. Annealing temperatures were as follow for the following paralogs A=62.1° C. B=65° C., C=65° C. and D=59.3° C.

This primary amplification product was then purified using the Qiagen MinElute PCR Purification Kit (Qiagen, Valencia, Calif.) and eluted in 10 µl of buffer EB. Three variants of a Paralog A forward orientation PCR primer (5'-XXX ATCGAGTTGTACCTTGGGAATG-3') (SEQ ID NO:27) in which XXX=GGC, CGG, or GCC and three variants of a Paralog A reverse orientation PCR primer (5'-XXX AATAAGTCCTTAACCTTACCTT-3') (SEQ ID NO:28) in which XXX=GGC, CGG, or GCC were synthesized and HPLC purified (IDT, Coralville, Iowa). Three variants of a Paralog B forward orientation PCR primer (5'-XXX AGAGTGATATCGAGTTGTACCTTG-3') (SEQ ID NO:29) in which XXX=CGG, CGC, or GCC and three variants of a Paralog B reverse orientation PCR primer (5'-XXX ACACTCCTTAACCTTACCTT-3') (SEQ ID NO:30) in which XXX=CGG, CGC, or GCC were synthesized and HPLC purified (IDT, Coralville, Iowa). Three variants of a Paralog C forward orientation PCR primer (5'-XXX AGAGTGATATTGAGTTGTACCTTG-3') (SEQ ID NO:31) in which XXX=CGG, GGC, or GCC and three variants of a Paralog C reverse orientation PCR primer (5'-XXX AAAGCTCCTTAACCTTTACCT-3') (SEQ ID NO:32) in which XXX=CGG, GGC, or GCC were synthesized and HPLC purified (IDT, Coralville, Iowa). The primers for the secondary PCR amplification (SEQ ID NO:25 and SEQ ID NO:26) for paralog D are described in section 4D. The 3 bp tags at the 5'-end of each primer served as an identifier key and indicated which B. napus sample the amplicon originated from. Primer pairs with matching identifier tags (keys) were used in combination to amplify purified primary PCR amplicon derived from samples describe above under the following conditions: 50 µl reaction volume containing 10 µl of purified PCR amplicon diluted 1:10, 1.25 µl each primer (10 µM each), 5 µl 10×

ACCUPRIME PCR buffer 1 and 0.3 µl (1.5 units) ACCUPRIME TaqDNA high fidelity polymerase (Invitrogen, Carlsbad, Calif.) in the enzyme manufacturer's buffer. Amplification products of the expected size resulted from amplification cycles consisting of 94° C. for 2 minutes, 33 cycles of (94° C. for 30 seconds, 62° C. for 30 seconds, 68° C. for 30 seconds), 68° C. for 5 minutes, and 4° C. held indefinitely, and were purified using Qiagen's (Valencia, Calif.) MINELUTE PCR purification kit as per the manufacturer's recommendations.

Massively parallel pyrosequencing reactions were performed directly on PCR products as described in section 4D. Analysis of the sequencing results was carried out by identifying sequence reads containing deletions of the expected size and position within the DNA molecule.

Results of these analyses indicated the presence of multiple small deletions at the expected ZFN cleavage sites in paralogs C and D (FIG. 7). pDAB7147 ZFN was again efficacious in cleaving two paralogs, C and D (and E). These deletions of 5-32 bp were precisely localized at the ZFN target site and demonstrated the cleavage of 2 or more EPSPS paralogs by the pDAB7147 ZFN. These results further demonstrate the ability of these engineered ZFNs to induce targeted, double-stranded breaks in a specific manner at an endogenous gene locus within a crop species.

One NHEJ each was also observed in paralogs A and B of samples 5, 6 and 9 treated with pDAB7147 and pDAB7150 (Table 5). These NHEJs were observed at the expected locations. However, since some of the control samples also contained one NHEJ (samples 2, 7 and 13 in Table 5), the ZFNs were not considered efficacious in cleaving these paralogs.

TABLE 5

The results of massively parallel sequencing showing DNA molecules that have undergone ZFN-mediated double-stranded-breaks followed by NHEJ repair in the targeted sequences of the four EPSPS paralaogs in *B. napus*. The control samples represent transgenic callus untreated with ZFNs.

| Sample number | Targeted paralog | ZFN construct | Primer | Sequences aligned | Total NHEJ |
|---|---|---|---|---|---|
| 1 | A | Control | Forward | 18,451 | 0 |
| 2 | A | Control | Reverse | 19,005 | 1 |
| 3 | A | pDAB7150 | Forward | 14,711 | 0 |
| 4 | A | pDAB7150 | Reverse | 15,616 | 0 |
| 5 | A | pDAB7147 | Forward | 21,478 | 1 |
| 6 | A | pDAB7147 | Reverse | 22,459 | 1 |
| 7 | B | Control | Forward | 12,682 | 1 |
| 8 | B | Control | Reverse | 18,033 | 0 |
| 9 | B | pDAB7150 | Forward | 11,361 | 1 |
| 10 | B | pDAB7150 | Reverse | 13,017 | 0 |
| 11 | B | pDAB7147 | Forward | 16,565 | 0 |
| 12 | B | pDAB7147 | Reverse | 17,499 | 0 |
| 13 | C | Control | Forward | 20,516 | 1 |
| 14 | C | Control | Reverse | 14,790 | 0 |
| 15 | C | pDAB7150 | Forward | 9,073 | 0 |
| 16 | C | pDAB7150 | Reverse | 9,096 | 1 |
| 17 | C | pDAB7147 | Forward | 12,696 | 3 |
| 18 | C | pDAB7147 | Reverse | 14,719 | 19 |
| 23 | D | pDAB7147 | Forward | 7,028 | 5 |
| 24 | D | pDAB7147 | Reverse | 6,832 | 9 |

Example 5: A Second ZFN Cleaves the Remaining Two Paralogs of the Five in *B. napus*

Next, ZFN-mediated double-stranded cleavage, focused on inducing double-stranded breaks in the remaining two paralogs A and B, was attempted. Two new engineered ZFNs that targeted different sequences, located about 350 bp 5' from the first ZFN binding location, were used (FIG. 4). These particular ZFN constructs, pDAB7185 and pDAB7186 (Table 3), were used in stable transformation of *B. napus* hypocotyl segments, as described in Example 4, section B. The stably transformed calli with ZFNs were frozen, lyophilized and DNA extracted as described previously in Example 4, section C. DNA was then digested with either BsoB1 (New England Biolabs, Ipswich, Mass.) or Lwe I (Fermentas, Inc., Hanover, Md.) to enrich for the fragments that had undergone NHEJs (FIG. 4). The digestions were carried out as per the manufacturer's instructions overnight and purified by ethanol precipitation as described previously. PCR amplification was then carried out using oligonucleotide primers specific for the target genes and flanking the predicted cleavage site of the ZFN. A forward orientation PCR primer for paralog A (5'-CAGCGTG-GAGCTTATCAGA-3') (SEQ ID NO:33) and reverse orientation PCR primer (5'-AAACGCAACACTAAGCAAAC-3') (SEQ ID NO:35), a forward orientation PCR primer for paralog B (5'-GAAGAGTAACAACGGCTCTGTG-3') (SEQ ID NO:34) and a reverse orientation PCR primer (5'-GAAAGAAAGAAGCAAACCGAC-3') (SEQ ID NO:90), specific for the targeted EPSPS gene paralogs were used in combination to amplify purified genomic DNA under the following conditions.

For Paralog A, 50 µl reaction volume containing 420-700 ng BsoBI digested genomic DNA template (10 µl), 1.25 ul each primer (at 10 µM each), 5 µl of 10× ACCUPRIME PCR buffer II, 5 µl of 10% PVP-40 and 0.3 µl (1.5 units) ACCUPRIME TaqDNA high fidelity polymerase (Invitrogen, Carlsbad, Calif.) in the enzyme manufacturer's buffer. Amplification products were generated from amplification cycles consisting of 94° C. for 2 minutes, 28 cycles of (94° C. for 30 seconds, 60° C. for 30 seconds, 68° C. for 1 minute), 68° C. for 5 minutes, 4° C. held indefinitely.

For Paralog B, 50 µl reaction volume containing 420-700 ng BsoBI digested gDNA template (10 µl), 1.25 µl each primer (at 10 µM each), 5 µl of 10× Accuprime PCR buffer II, 5 µl of 10% PVP-40 and 0.3 µl (1.5 units) ACCUPRIME TaqDNA high fidelity polymerase (Invitrogen, Carlsbad, Calif.) in the enzyme manufacturer's buffer. Amplification products were generated from amplification cycles consisting of 94° C. for 2 minutes, 28 cycles of (94° C. for 30 seconds, 58° C. for 30 seconds, 68° C. for 1 minute), 68° C. for 5 minutes, 4° C. held indefinitely. This primary amplification product was then isolated using the MINELUTE PCR purification kit (Qiagen, Valencia, Calif.) eluting in 10 µl of buffer EB. Three variants of a Paralog A forward orientation PCR primer (5'-XXX TCTGTTTCCACGGCG-GAG-3') (SEQ ID NO:36) in which XXX=CCG, GCG, or CGC and three variants of a Paralog A reverse orientation PCR primer (5'-XXX AAGCGGCAAGAAGAAGAATC-3') (SEQ ID NO:37) in which XXX=CCG, GCG, or CGC were synthesized and HPLC purified (IDT, Coralville, Iowa). Three variants of a Paralog B forward orientation PCR primer (5'-XXX TCTGTTTCCACGGCTGAG-3') (SEQ ID NO:38) in which XXX=GGC, GCC, or CGG and three variants of a Paralog B reverse orientation PCR primer (5'-XXX ATTGGACAGAGATTTGGGTC-3') (SEQ ID NO:39) in which XXX=GGC, GCC, or CGG were synthesized and HPLC purified (IDT, Coralville, Iowa). The 3-bp tags at the 5'-end of each primer serve as an identifier key and indicated which sample the amplified fragments originated from. Primer pairs with matching identifier tags (keys) were used in combination to amplify purified primary PCR amplicon derived from samples describe above under the following conditions: 50 μl reaction volume containing 10 μl of purified PCR amplicon diluted 1:10, 1.25 μl each primer (10 μM each), 5 μl 10× ACCUPRIME PCR buffer 1 and 0.3 μl (1.5 units) ACCUPRIME TaqDNA high fidelity polymerase (Invitrogen, Carlsbad, Calif.) in the enzyme manufacturer's buffer.

Amplification products of the expected size resulted from amplification cycles consisting of 94° C. for 2 minutes, 25 cycles of (94° C. for 30 seconds, annealing for 30 seconds, 68° C. for 30 seconds), 68° C. for 5 minutes, 4° C. held indefinitely and were purified using Qiagen's (Valencia, Calif.) MINELUTE PCR purification kit as per the manufacturer's recommendations Annealing temperatures for secondary PCR reaction listed above were as follows: Paralog A at 66° C. and Paralog B at 64° C.

Massively parallel pyrosequencing reactions were performed directly on the PCR products. Analysis of the sequencing results was carried out by identifying sequence reads containing deletions of the expected size and position within the DNA molecule.

Results of these analyses indicated the presence of multiple small deletions at the expected cleavage site (FIG. 8, Table 6). Again, these deletions were precisely localized at the ZFN target site and indicated that double-stranded breaks, induced by the ZFN, were generated in the genome and subsequently repaired by NHEJ. ZFN cloned in pDAB7185 was overall more effective in causing double-stranded breaks than ZFN pDAB7186.

These results further demonstrated the ability of these engineered ZFNs to induce targeted, double stranded breaks in a specific manner at an endogenous gene locus within a crop species. The results also demonstrated the ability of the same ZFN to cleave two EPSPS paralogs, A and B.

TABLE 6

The results of massively parallel sequencing showing DNA molecules that have undergone ZFN-mediated double-stranded-breaks followed by NHEJ repair in the targeted sequences of the EPSPS paralaogs, A and B, in *B. napus*. The control samples represent transgenic callus untreated with ZFNs.

| S.N. | Targeted paralog | ZFN construct | Primer | Sequences aligned | Total NHEJ |
|---|---|---|---|---|---|
| 1 | A | Control | Forward | 12903 | 0 |
| 2 | A | Control | Reverse | 12027 | 0 |
| 3 | A | pDAB7185 | Forward | 10432 | 9 |
| 4 | A | pDAB7185 | Reverse | 9883 | 3 |
| 5 | A | pDAB7186 | Forward | 20,496 | 2 |
| 6 | A | pDAB7186 | Reverse | 18697 | 3 |
| 7 | B | Control | Forward | 20655 | 0 |
| 8 | B | Control | Reverse | 22733 | 0 |

TABLE 6-continued

The results of massively parallel sequencing showing DNA molecules that have undergone ZFN-mediated double-stranded-breaks followed by NHEJ repair in the targeted sequences of the EPSPS paralogs, A and B, in *B. napus*. The control samples represent transgenic callus untreated with ZFNs.

| S.N. | Targeted paralog | ZFN construct | Primer | Sequences aligned | Total NHEJ |
|---|---|---|---|---|---|
| 9 | B | pDAB7185 | Forward | 15663 | 32 |
| 10 | B | pDAB7185 | Reverse | 15864 | 26 |
| 11 | B | pDAB7186 | Forward | 21333 | 4 |
| 12 | B | pDAB7186 | Reverse | 24003 | 12 |

Example 6: Two ZFNs can Cleave all EPSPS Paralogs

In another example, *B. napus* hypocotyl segments were co-transformed with two ZFNs and stable transgenic events were created containing both the ZFNs, which demonstrated NHEJs in all EPSPS paralogs. The specific ZFN constructs used for co-transformation in this experiment were pDAB7147 and pDAB7185 (Table 3). Stable transgenic callus events were generated, DNA isolated and analyzed as described in Examples 4 and 5. NHEJs in all four EPSPS paralogs, A, B, C and D, similar to those described in sections 4 and 5, were identified. Again, NHEJs in paralogs D and E could not be differentiated due to sequence similarity. All of the NHEJs were located in the predicted targeted sequences of the various paralogs.

These results validate two points: 1. ZFNs can be designed against differentiated sequences of a multi-gene family to specifically cleave 1-2 gene/paralog. 2. Multiple ZFNs can be used, if needed, to cleave all gene paralogs simultaneously.

Additional information related to targeted cleavage, targeted recombination and targeted integration can be found in United States Patent Application publications US-2003-0232410; US-2005-0026157; US-2005-0064474; US-2005-0208489 and US-2007-0134796, the disclosures of which are incorporated by reference in their entireties for all purposes.

All patents, patent applications and publications mentioned herein are hereby incorporated by reference, in their entireties, for all purposes.

Although disclosure has been provided in some detail by way of illustration and example for the purposes of clarity of understanding, it will be apparent to those skilled in the art that various changes and modifications can be practiced without departing from the spirit or scope of the disclosure. Accordingly, the foregoing descriptions and examples should not be construed as limiting.

What is claimed is:

1. A method for stimulating homologous recombination in the genome of a plant cell, the method comprising the step of:
   introducing a zinc finger nuclease (ZFN) into the plant cell in the presence of a DNA segment in the plant cell, wherein the DNA segment comprises at least one target site in an 5-enolpyruvyl shikimate-3-phosphate synthase (EPSPS) gene, wherein said target site comprises any one of SEQ ID NO: 141-153, wherein the ZFN cleaves the DNA segment and stimulates homologous recombination, wherein the ZFN comprises a non-naturally occurring zinc finger protein (ZFP) that binds to said target site in the EPSPS gene, wherein the ZFP comprises the recognition helix regions designated and ordered as set forth in any single row of Table A.

2. The method of claim 1, wherein the homologous recombination results in a deletion within the DNA segment.

3. The method of claim 2, wherein the deleted DNA sequence is replaced by an exogenous sequence, the method further comprising:
   introducing a polynucleotide comprising the exogenous sequence into the cell, wherein the polynucleotide comprises at least a first and a second region of homology to the EPSPS gene, said regions of homology flanking the exogenous sequence.

4. The method of claim 3, wherein the exogenous sequence encodes a selectable marker.

5. The method of claim 4, wherein the selectable marker is selected from the group consisting of green fluorescent protein, β-glucuronidase, phosphinothricin N-acetyl transferase, neomycin phosphotransferase, hygromycin phosphotransferase, β-lactamase, catechol dioxygenase, α-amylase, tyrosinase, β-galactosidase, luciferase, aequorin, nitrilase, acetolactate synthase, dihydrofolate reductase, dalapon dehalogenase, and anthranilate synthase.

6. The method of claim 3, wherein the exogenous sequence is an EPSPS gene sequence.

7. The method of claim 6 wherein the EPSPS gene sequence comprises a mutation relative to the wild-type EPSPS sequence.

8. The method of claim 7, wherein the mutation increases tolerance of a plant to herbicide glyphosate relative to a control plant.

* * * * *